United States Patent
Herrlein et al.

(10) Patent No.: US 11,324,688 B2
(45) Date of Patent: May 10, 2022

(54) BICOMPONENT COMPOSITION

(71) Applicant: HFC Prestige International Holding Switzerland S.a.r.l, Petit-Lancy (CH)

(72) Inventors: Mathias Kurt Herrlein, Kronberg (DE); Graham Neil McKelvey, Schwalbach (DE); Matija Crne, Wiesbaden (DE); Corinne Mohr, Lorsch (DE); Simon Paul Godfrey, Oberursel (DE); Axel Meyer, Frankfurt am Main (DE)

(73) Assignee: WELLA INTERNATIONAL OPERATIONS SWI, Petit-Lancy (CH)

( * ) Notice: Subject to any disclaimer, the term of this patent is extended or adjusted under 35 U.S.C. 154(b) by 0 days.

(21) Appl. No.: 17/044,749

(22) PCT Filed: Mar. 27, 2019

(86) PCT No.: PCT/EP2019/057812
§ 371 (c)(1),
(2) Date: Oct. 1, 2020

(87) PCT Pub. No.: WO2019/192916
PCT Pub. Date: Oct. 10, 2019

(65) Prior Publication Data
US 2021/0145726 A1 May 20, 2021

Related U.S. Application Data

(60) Provisional application No. 62/652,231, filed on Apr. 3, 2018, provisional application No. 62/652,256, filed on (Continued)

(30) Foreign Application Priority Data

May 3, 2018 (EP) .................................... 18170717

(51) Int. Cl.
*A61Q 5/00* (2006.01)
*A61K 8/81* (2006.01)
(Continued)

(52) U.S. Cl.
CPC ............ *A61K 8/8147* (2013.01); *A61K 8/817* (2013.01); *A61K 8/898* (2013.01); *A61Q 5/065* (2013.01);
(Continued)

(58) Field of Classification Search
CPC .. A61Q 5/065; A61K 2800/43; A61K 8/8152; A61K 2800/432; A61K 2800/884;
(Continued)

(56) References Cited

U.S. PATENT DOCUMENTS

2011/0083284 A1* 4/2011 Suddaby ................. A61Q 5/10
8/405
2015/0174051 A1* 6/2015 Teboul ..................... A61K 8/26
424/70.6
(Continued)

FOREIGN PATENT DOCUMENTS

EP  3015134 A1  5/2016
EP  3015135 A1  5/2016
(Continued)

OTHER PUBLICATIONS

"International Application Serial No. PCT/EP2019/057812, International Search Report dated Jul. 1, 2019", 5 pgs.
(Continued)

*Primary Examiner* — Eisa B Elhilo
(74) *Attorney, Agent, or Firm* — Victoria Friedman; Dennemeyer & Associates LLC

(57) ABSTRACT

The instant disclosure generally relates to a bicomponent composition for coloring mammalian or synthetic keratin fibers, the bicomponent composition comprising first, sec-
(Continued)

ond, components. The first component includes an organic polymer, the second component includes a pretreatment base compound. One or more of the components includes pigment microparticles. The bicomponent composition combines upon application to treated material such as hair, forms a solid coating thereon and has a substantially long color fastness following development (setting). Methods of using such compositions are also described herein.

20 Claims, 3 Drawing Sheets

Related U.S. Application Data on Apr. 3, 2018, provisional application No. 62/654,993, filed on Apr. 9, 2018, provisional application No. 62/694,781, filed on Jul. 6, 2018, provisional application No. 62/694,799, filed on Jul. 6, 2018, provisional application No. 62/694,734, filed on Jul. 6, 2018, provisional application No. 62/694,808, filed on Jul. 6, 2018, provisional application No. 62/696,301, filed on Jul. 10, 2018.

(51) Int. Cl.
*A61K 8/898* (2006.01)
*A61Q 5/06* (2006.01)

(52) U.S. Cl.
CPC .... *A61K 2800/43* (2013.01); *A61K 2800/594* (2013.01); *A61K 2800/884* (2013.01)

(58) Field of Classification Search
CPC ........ A61K 8/898; A61K 8/8147; A61K 8/37; A61K 8/817; A61K 2800/594
USPC .............................................................. 8/405
See application file for complete search history.

(56) References Cited

U.S. PATENT DOCUMENTS

| | | | |
|---|---|---|---|
| 2016/0120284 A1* | 5/2016 | Crne | A61K 8/8117 |
| | | | 132/208 |
| 2016/0120285 A1* | 5/2016 | Crne | A61K 8/81 |
| | | | 132/208 |
| 2016/0235655 A1* | 8/2016 | Herrlein | A61K 8/731 |
| 2018/0263353 A1* | 9/2018 | Crne | A61K 8/731 |
| 2018/0263354 A1* | 9/2018 | Crne | A45D 19/00 |

FOREIGN PATENT DOCUMENTS

| | | |
|---|---|---|
| EP | 3058934 A1 | 8/2016 |
| FR | 2992559 A1 | 1/2014 |
| WO | WO-2009073759 A1 | 6/2009 |
| WO | WO-2018185345 A1 | 10/2018 |
| WO | WO-2019192916 A1 | 10/2019 |

OTHER PUBLICATIONS

"International Application Serial No. PCT/EP2019/057812, Written Opinion dated Jul. 1, 2019", 8 pgs.

* cited by examiner

BICOMPONENT COMPOSITION

CROSS-REFERENCE TO RELATED APPLICATION

This application is a U.S. National Stage Filing under 35 U.S.C. 371 from International Application No. PCT/EP2019/057812, filed on Mar. 27, 2019, and published as WO 2019192916 on Oct. 10, 2019, which application claims priority to U.S. Provisional Application No. 62/652,231, filed Apr. 3, 2018, U.S. Provisional Application No. 62/652,256, filed Apr. 3, 2018, U.S. Provisional Application No. 62/654,993, filed Apr. 9, 2018, U.S. Provisional Application No. 62/694,781, filed Jul. 6, 2018, U.S. Provisional Application No. 62/694,799, filed Jul. 6, 2018, U.S. Provisional Application No. 62/694,734, filed Jul. 6, 2018, U.S. Provisional Application No. 62/694,808, filed Jul. 6, 2018, U.S. Provisional Application No. 62/696,301, filed Jul. 10, 2018, and European Application No. 18170717.5, filed May 3, 2018, all of which applications are incorporated herein by reference in their entirety.

BACKGROUND

Treatments to mammalian or synthetic keratin fibers, and their surfaces (integument/nonwoven/textile), are well known in the art. Of particular note are treatments that alter the color appearance of the hair or provide other colored or reflective properties through surface treatment of the hair; dissolution (absorption) of dye molecules into the keratin fiber or attachment to the fiber surface (so called direct dyes); and/or dissolution of dye precursors into the keratin fiber, followed by reaction of these dye precursors within the hair to form dye species (so called oxidative dyeing). Surface coloration treatments and many soluble dyes can be later washed out. Alternatively, pigments can be adhered to the hair surface to alter the perceived color.

One drawback of the known oxidation based technologies in this area is that the methods for applying dye based coloring materials involves compositions that may in some cases cause temporary irritation to the scalp. This prevents the hair coloration experience from being pleasant or a so called wellness experience. Such coloring compositions also alter the hair structure itself, leading to oxidation of the hair surface, and partial degradation to the keratinous proteins from which the hair structure is constructed. With repeated coloring, these changes in hair structure become more pronounced. The color obtained when coloring with such composition is hard to predict, and even highly experienced users can still be surprised with the results that are obtained. Yet another drawback to known technologies is that, once the color is on the hair, the dye based coloring material is difficult to remove and/or cannot be completely removed.

Another drawback for the dye based approach is that the application of hair coloration materials can yields uneven results as adherence to the surface and/or penetration of hair coloration materials into the hair can vary with hair type for example for a consumer differing color results may be visible between hair roots and hair tips. This can lead to an unnatural looking result. Some desired differences may still be visible due to the non-uniformity in coloration of the underlying hair, for example subtle difference in strand to strand levels of pheomelanin and eumelanin in a consumer may yield slightly different color results, even when the same color pigments or dyes are applied to a consumer. While some strand to strand variation is needed to provide natural looking hair, too much or too little can again lead to an unnatural looking color result. Due to the number of factors that determine the final hair color result for example, the length of application time, the underlying hair color, the hair changes from root to tip, it is difficult even for experienced users to accurately predict the final color result and look.

A drawback of pigment based coloring approaches is the low adherent fastness of the pigment or colored material to the keratin fibers. While the low adherent fastness or remanence has been attributed to the use of film formers that are water soluble, substituting film formers that are classed as water insoluble does not deliver much better remanence. Irrespective of the film former applied, the result is effective removal of the color on the hair after only a few washings with shampoo. Especially for persons who shampoo daily, the rapid color loss creates an undesirable situation.

Another drawback for both dye and pigment based approaches is that the application of hair coloration materials often yields uneven results as (1) adherence and or penetration of hair coloration materials to the hair surface or within the hair can vary with hair type for example due to changes in porosity, changes in surface composition due to proximity to scalp and/or age of the user; and (2) even when material is adhered or penetrated into the hair, differences in coloration of the underlying hair, including presence of pheomelanin and eumelanin, may yield different color results, even when the same color pigments or dyes are applied across hair types/colors having different native characteristics.

There is therefore a need for an improved composition and method that not only make the hair coloring experience more pleasant, but also is user friendly, provides appropriate color and luster, and leaves the hair manageable, free flowing and capable of moving naturally and does not result in harm to hair protein.

SUMMARY

According to aspects of the invention, embodiments of the bicomponent composition for coloring treated material, methods for its production and application, coated treated material resulting from the bicomponent composition and methods for removal of the coating provide a surface coloration of keratin material and textiles, especially hair, that may be substantially uniform to significantly varied, may give such material an appearance of a lower or higher chroma, shiny or reflective nature. [Hereinafter the combination of keratin materials and textiles will be designated as treated material.] These aspects provide color fastness during a series of washes with shampoo or soap yet with appropriate formulations can be readily removed to leave the natural state of the treated material and especially the natural state and/or shade of the hair when hair is the kind of treated material used. These aspects significantly lessen and/or avoid treatment of treated material that may cause breakage of keratin protein intermolecular bonds and interruption of mechanical and/or chemical linkages of textiles.

It has been discovered that application of embodiments of the bicomponent composition comprising first and second components to treated material delivers significantly increased remanence. The first and second components with constituents including respectively an organic polymer and a pretreatment base compound combine to provide remanence, flexibility, softness and similar properties to the resulting coating. The combination of the pretreatment followed by application of the first component achieves a coating on the treated material with remarkable remanence.

One aspect of the invention concerns a bicomponent composition. Embodiments of the bicomponent composition comprise a first component comprising an organic polymer, a second component comprising a pretreatment base compound. The first and second components are capable of forming dipolar and/or electrostatic interaction with each other as well as with the treated material The bicomponent composition also comprises a medium with one or more of the first and second components and pigment microparticles incorporated into one or more of the first and second components.

The first and second components are typically maintained separately. If multiple, different functional groups are present in either, or both, of the first and second components, the multiple different functional groups are selected to be appropriately compatible. For example, the presence of multiple different functional groups of the organic polymer are selected or adapted or otherwise controlled so that they do not interact together while standing alone and separate from the pretreatment base compound.

The first and second components of the bicomponent composition may be applied separately and sequentially to the treated material. Upon the combination of the first and second components, the organic polymer and the pretreatment base compound interact to form a wash resistant coating with pigment microparticles on the treated material. While it is not a limitation of the invention, it is believed that the base compound enables interaction among the organic polymer, the pretreatment base compound and the treated material. This interaction is believed to adhere substances together to make them resistant to removal by ordinary means.

The embodiments of the first component include an organic polymer respectively of the pretreatment base compound and the base compound in a manner as described above. The organic polymer may be any carbon based polymer based on olefinic monomers, polyol monomers, ester monomers, amide monomers, carbonate monomers, natural occurring monomers and polymers having repeating monomeric residues based on carbon or carbon in combination with other atoms such as oxygen and/or nitrogen, and any combination thereof.

The embodiments of the second component include a base compound. The base compound is composed of a small molecule or an oligomeric or polymeric organic or silicone core to which is covalently bonded pendant or terminal or pendant and terminal amine, carboxylate, sulfonate, carbamate and mercapto groups, preferably amine groups. The is typically and usually adapted to be combined with the treated material as a pretreatment followed by application of the first component. The first and second components are typically maintained in a separate container prior to use.

The molar ratio of pretreatment base compound to organic polymer will depend upon the kinds and numbers of pendant functional groups of the organic polymer, the pretreatment base compound to achieve the desired properties of the coating of the composition. The interaction will improve resistance of the coating toward removal with dilute soap or shampoo aqueous solutions while preserving free hair flow properties and avoid stickiness and clumping.

Embodiments of the pigment microparticles used on the bicomponent composition described herein may comprise organic pigment microparticles, which imparts color to the hair, and colored reflective microparticles, for providing light scattering properties to the colored hair, Embodiments may also include microparticle metal flakes for light reflection to add shine to the desired color or to make the hair appear to be lighter than the starting hair color.

An aspect of the invention concerning the method for coating the bicomponent composition with treated material comprises applying the pretreatment base compound to the treated material and preferably at least partially drying to form pretreated treated material. Next, the first component may be applied to the pretreated treated material. The pretreated treated material coated with the first component may be dried with optional heat to cause formation of a colored coating on the treated material. The embedded pigment microparticles are somewhat to substantially uniformly distributed in and throughout the coating.

In addition to the organic polymer, pretreatment base compound and pigment microparticles of the first and second components, the bicomponent composition may optionally contain additional ingredients helpful and beneficial to the treated material and/or its coloration. These additional ingredients include but not limited to one or more of dispersants, surface treatment agents for the pigment microparticles, plasticizers, conditioners, suspending agents, thickening agents, adjuvants, moisturizers, surfactants, fatty substances, hair feel modification agents, waxes, fatty amides and soluble organic dyes of colors different from those of the pigment microparticles.

An aspect of the invention concerning the fastness or remanence of the coating on the treated material, and especially on hair strands, comprises the ability of the coating to somewhat to substantially resist dissolution by ordinary cleaning of the treated material such as hair. Ordinary cleaning may involve washing with soap and water, washing with an aqueous dilution of shampoo and washing with water.

An aspect of the invention concerning removal of the coating on the treated material, such as on hair strands, comprises application of a trigger formulation designed to remove the coating. The trigger formulation embodiments of the invention may comprise a medium with a base. Embodiments of the base include organic and inorganic compounds that provide a stronger basic medium than does a dilute aqueous mixture of soap or a shampoo containing an anionic surfactant.

An additional aspect of the invention concerns the application of the bicomponent composition to treated material such as brows, lashes, nails and skin as well as to hair on the scalp. Additionally, the bicomponent composition may be applied to textiles made of plant material, animal hair or fur or synthetic material. The bicomponent composition may be applied to these kinds of treated materials and to textiles with appropriate adjustments of the composition parameters within the parameters described for hair on the scalp. Typically, the eyebrow hair may be treated with the bicomponent composition using parameters similar to or the same as those of the bicomponent composition for hair on the scalp. The hair of eyelashes typically can be similarly treated with the bicomponent composition for eyebrows and the viscosity adjusted to provide a somewhat more viscous composition for application to the eye lashes. For nails and skin, the parameters of the bicomponent composition may have a higher solids content and higher number of first and second components third functional groups for combining than the parameters for the hair and viscosity may be adjusted to provide embodiments that will not readily drip or otherwise flow off the nail or skin surface to which the bicomponent composition is applied. The bicomponent composition for nails and textiles will preferably have higher interaction to provide a durable coating or covering on the keratin nail and textiles.

DEFINITIONS

Figure 1:
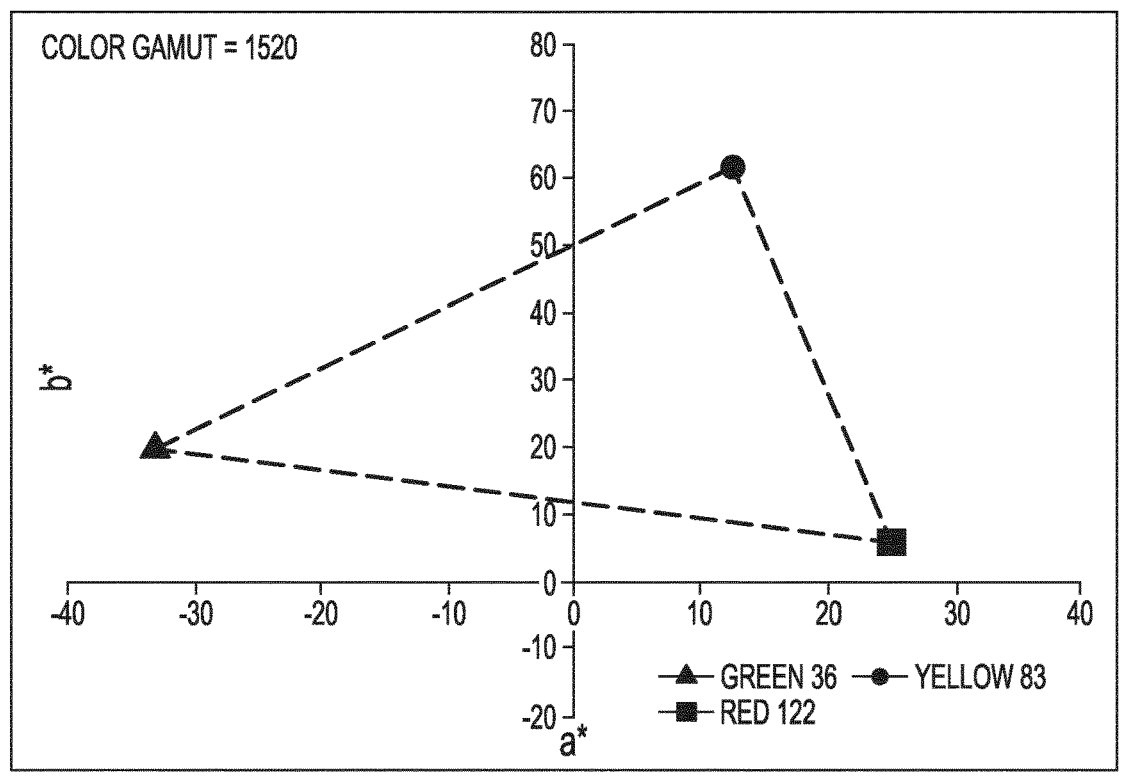
FIG. 1 depicts a Gamut plot of green, yellow and red pigments.

Unless defined otherwise, all technical and scientific terms used herein have the same meaning as commonly understood by a person of ordinary skill in the art.

As used in the specification and the appended claims, the singular forms "a," "an" and "the" include plural referents unless the context clearly dictates otherwise.

The term "may" in the context of this application means "is permitted to" or "is able to" and is a synonym for the term "can." The term "may" as used herein does not mean possibility or chance.

The term and/or in the context of this application means one or the other or both. For example, an aqueous solution of A and/or B means an aqueous solution of A alone, an aqueous solution of B alone and an aqueous solution of a combination of A and B.

The terms (meth)acrylic acid and (meth)acrylate mean herein both of the acrylic acid and methacrylic acid and both of the acrylate methacrylate esters. The parenthesis surrounding the prefix "meth" means that the term (meth) acrylic encompasses both of the methacrylic acid and acrylic acid monomers. This term has the same meaning when used with polymers. Without a parenthesis, the term "methacryl" means only the methacrylic acid and esters and does not include acrylic acid and esters. The suffix "ate" means that the term (meth)acrylate is an ester formed by combination of a monoalcohol or diol with methacrylic acid or acrylic acid.

Acid value is determined by the usual and customary method described in chemical literature.

The molecular weight of a polymer or oligomer used according to the invention may be measured by a weight average molecular weight, and the distribution of molecules of different molecular weights of a polymer or oligomer used according to the invention is determined by its polydispersity index. Molecular weight is expressed as Daltons (Da), kilo Daltons (KDa) and mega Daltons, which is million Daltons or (MDa). The acronym $M_w$ stands for weight average molecular weight and $M_n$ is the number average molecular weight of a given polymer. Polydispersity is a unit-less number and indicates the breadth of the distribution of the polymer molecular weights and is defined as the $W_m/M_n$.

The term "about" is understood to mean ±10 percent of the recited number, numbers or range of numbers.

The term "about 0 wt. %" is understood to mean that no substance, compound or material to which zero (0) refers is present, up to a negligible but detectable amount is present, assuming that the detectability can be determined on a parts per million basis.

The term "hydrogen bonding" is understood to mean a compound or group that contain a hydroxyl group or a hydrogen that is part of a polar group, such as but not limited to an amine, a carboxylic acid, a urethane group, a urea group and other similar groups and that can form molecule to molecule interaction through electrostatic or ionic interaction between positive and negative dipolar or ionic groups.

As used herein, the terms "covalent, coordinate, electrostatic, ionic, dipolar and entanglement or entwining interactions" mean a chemical relationship between two atoms or two groups of atoms. The interaction includes a covalent bond between the atoms such as the covalent bond between the two carbons of ethane. The interaction includes a coordinate bond between two or more atoms such as the coordinate bond between oxygen and sulfur of the sulfate anion ($SO_4^{-2}$) or a complex of zinc and EDTA. The interaction includes an electrostatic or ionic interaction between two charged atoms or particles such as the interaction between sodium and chloride of salt or between ammonium and acetate of ammonium acetate. Dipolar interaction includes hydrogen bonding such as the interaction between water and the hydroxyl of methyl alcohol. The interaction includes entanglement or entwining which is lipophilic interaction or mechanical/physical twisting together such as is present in the molecules of polyethylene.

Where features or aspects of the invention are described in terms of Markush groups, those skilled in the art will recognize that the invention is also thereby described in terms of any individual member or subgroup of members of the Markush group. For example, if X is described as selected from the group consisting of methyl, ethyl or propyl, claims for X being methyl and claims for X being ethyl and propyl are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

If a value of a variable that is necessarily an integer, e.g., the number of carbon atoms in an alkyl group or the number of substituents on a ring, is described as a range, e.g., 0-4, what is meant is that the value can be any integer between 0 and 4 inclusive, i.e., 0, 1, 2, 3, or 4. Similarly, values expressed in a range format should be interpreted in a flexible manner to include not only the numerical values explicitly recited as the limits of the range, but also to include all the individual numerical values or sub-ranges encompassed within that range as if each numerical value and sub-range were explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range.

Hair and hair strands mean natural or synthetic keratin fibers. Hair, hair strands and keratin fibers are used interchangeably in this document. Natural keratin fibers include those from mammals and/or on mammals including human, primate, ruminant, camelid, equine, rodent and neovison including but not limited to cow, sheep, deer, goat, buffalo, lama, alpaca, camel, guanaco, vicuna, horse, antelope, moose, elk, rat, mouse, beaver, rabbit, mink, monkey, ape and similar species. Natural keratin fibers may include hair, fur or nails. Synthetic fibers include polyamides, polyacrylic and polyester fibers, especially polyamide fibers which are used for artificial hair implantation.

Oligomer and polymeric compounds mean repeating units of carbon-carbon backbones with side chains of various classes of groups. The oligomeric and polymer compounds may have side chains of aliphatic groups such as alkyl and/or alkenyl groups, aromatic groups such as phenyl and/or naphthyl groups, heteroaromatic groups such as pyridinyl, quinolinyl, quinazolinyl groups, carboxylic acid groups, hydroxyl groups, amine groups, mercapto groups, sulfo acid groups, sulfinyl acid groups, carboxyl ester groups, carbamide groups, sulfamide groups, alkoxy groups, monomeric, oligomeric and/or polymeric ether groups, monomeric, oligomeric and/or polymeric imino groups, and optionally may have some reactive derivative groups such as an acyl group bound to a leaving group. The oligomeric and polymeric compounds may be composed of a single monomeric unit structure such as polystyrene or polyacrylic acid or may have several different monomeric unit structures such as poly (styrene-acrylic acid-methyl acrylate). The multiple monomeric unit structures may include side chains of esters, amides and side chains such as alkyl groups or aromatic groups or similar groups which not derived from carboxylic acid groups.

As used herein, the term "transfer resistance" generally refers to the quality exhibited by compositions that are not readily removed by contact with another material, such as, for example, an item of clothing or the skin. Transfer resistance can be evaluated by any method known in the art for evaluating such. For example, transfer resistance of a composition can be evaluated by the amount of product transferred from a wearer to any other substrate after the expiration of a certain amount of time following application of the composition to the hair. The amount of composition transferred to the substrate can then be evaluated and compared. For example, a composition can be transfer resistant if a majority of the product is left on the wearer's hair. Preferably little or no composition is transferred to the substrate from the hair.

A transfer test method means the ability or lack of ability to transfer color from treated material to clothing or other material. The transfer of the composition from the hair can be assessed using the following method. Hair tresses are colored according to the test method described. A white cotton cloth is used to test the composition transfer. The cloth measuring 15 mm by 75 mm is folded in half so as to create two sides with a size of 15 mm by 37.5 mm. Between the two sides the colored hair tress is inserted and laid flat onto a surface such that the top portion of the tress where it is glued together just protrudes from the folded two sides of cotton. A weight of 0.1 Kg is applied evenly over the top surface of the cotton and the hair which is wrapped below it. The hair tress is then pulled through the cotton cloth over a time until it is removed altogether from the cloth in 1 to 3 seconds. The weight is removed, and the cloth opened to reveal the inner surface. A visual assessment can then be performed on the sample to give it a rating from 0 to 5 for color transfer, with 0 being no transfer and 5 being extremely high transfer. The method can also be used to compare between different prototypes and provide a comparative assessment of better or worse performance.

As used herein, the term "minimally alters the keratin material or fibers, upon application" generally means that after removal of the composition coating on the keratin fibers such as hair, the keratin fibers are returned to a substantially unaltered state. The state of the keratin fibers such as hair can be assessed for example using ATR FT-IR for oxidative damage as described later or through tensile testing methods known to those skilled in the art for assessing fiber strength for example using equipment such as those designed and sold by Dia-Stron™.

As used herein, the term "setting" means converting the bicomponent composition to a solid coating through the application of means designed to remove or otherwise separate the medium from the other constituents of the bicomponent composition so as to leave a solid coating of the organic polymer, pretreatment base compound and base compound and other optional ingredients of the composition.

"in situ" is a Latin phase meaning in its original place. In the context of this invention, it means an activity such an interaction arrangement by hydrogen bonding, polar coupling or electrostatic activity between two or more molecules that occurs in place on the treated material such as hair.

"Aliphatic substituent, group or component" refers to any organic group that is non-aromatic. Included are acyclic and cyclic organic compounds composed of carbon, hydrogen and optionally of oxygen, nitrogen, sulfur and other heteroatoms. This term encompasses all of the following organic groups except the following defined aromatic and heteroaromatic groups. Examples of such groups include but are not limited to alkyl, alkenyl, alkynyl, corresponding groups with heteroatoms, cyclic analogs, heterocyclic analogs, branched and linear versions and such groups optionally substituted with functional groups, as these groups and others meeting this definition of "aliphatic" are defined below.

"Aromatic substituent, group or component" refers to any and all aromatic groups including but not limited to aryl, aralkyl, heteroalkylaryl, heteroalkylheteroaryl and heteroaryl groups. The term "aromatic" is general in that it encompasses all compounds containing aryl groups optionally substituted with functional groups (all carbon aromatic groups) and all compounds containing heteroaryl groups optionally substituted with functional groups (carbon-heteroatom aromatic groups), as these groups and others meeting this definition of "aromatic" are defined below.

As used herein, the term "optionally" means that the corresponding substituent or thing may or may not be present. It includes both possibilities.

"Alkyl" refers to a straight or branched hydrocarbon chain radical consisting solely of carbon and hydrogen atoms, unless otherwise specifically described as having additional heteroatoms or heterogroups. The alkyl group contains no unsaturation, having from one to twenty-two carbon atoms (e.g., $C_1$-$C_{24}$ alkyl). Whenever it appears herein, a numerical range such as "1 to 24 refers to each integer in the given range; e.g., "1 to 24 carbon atoms" means that the alkyl group may consist of 1 carbon atom, 2 carbon atoms, 3 carbon atoms, etc., up to and including 24 carbon atoms, although the present definition also covers the occurrence of the term "alkyl" where no numerical range is designated. In some embodiments, it is a $C_1$-$C_4$ alkyl group. Typical alkyl groups include, but are in no way limited to, methyl, ethyl, propyl, isopropyl, n-butyl, iso-butyl, sec-butyl isobutyl, tertiary butyl, pentyl, isopentyl, neopentyl, hexyl, septyl, octyl, nonyl, decyl, and the like. The alkyl is attached to the rest of the molecule by a single bond, for example, methyl (Me), ethyl (Et), n-propyl, 1-methylethyl (iso-propyl), n-butyl, n-pentyl, 1,1-dimethylethyl (t-butyl), 3-methylhexyl, 2-methylhexyl, and the like.

"Alkylenyl" refers to a straight or branched divalent hydrocarbon chain consisting solely of carbon and hydrogen atoms, unless otherwise specifically described as having additional heteroatoms or heterogroups. The alkylenyl group contains no unsaturation has a valence bond at either end of the chain and has a numerical range of carbon atoms of 1 to 24, which numerical range includes each integer in the range. An example of a divalent hydrocarbon chain designated as an alkylenyl group is —$CH_2$—$CH_2$—$CH_2$—$CH_2$— which is butylenyl.

"Cycloalkyl" refers to a monocyclic or polycyclic radical that contains only carbon and hydrogen, and may be saturated, or partially unsaturated. Cycloalkyl groups include groups having from 3 to 24 ring atoms (i.e., $C_2$-$C_{10}$ cycloalkyl). Whenever it appears herein, a numerical range such as "3 to 24" refers to each integer in the given range; e.g., "3 to 24 carbon atoms" means that the cycloalkyl group may consist of 3 carbon atoms, etc., up to and including 10 carbon atoms. In some embodiments, it is a $C_3$-$C_8$ cycloalkyl radical. In some embodiments, it is a $C_3$-$C_5$ cycloalkyl radical. Illustrative examples of cycloalkyl groups include, but are not limited to the following moieties: cyclopropyl, cyclobutyl, cyclopentyl, cyclopentenyl, cyclohexyl, cyclohexenyl, cycloseptyl, cyclooctyl, cyclononyl, cyclodecyl, norbornyl, and the like.

"Alkoxy" refers to the group —O-alkyl, including from 1 to 24 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. "Lower alkoxy" refers to alkoxy groups containing one to six carbons. In some embodiments, $C_1$-$C_4$ alkyl is an alkyl group which encompasses both straight and branched chain alkyls of from 1 to 4 carbon atoms.

"Amino" or "amine" refers to an —$N(R^a)_2$ radical group, where each $R^a$ is independently hydrogen or linear, branched or cyclic alkyl of 1 to 6 carbons. When an —$N(R^a)_2$ group has two Ra other than hydrogen they can be combined with the nitrogen atom to form a 4-, 5-, 6-, or 7-membered ring.

"Aryl" refers to a conjugated pi radical with six or ten ring atoms which has at least one ring having a conjugated pi electron system which is carbocyclic (e.g., phenyl, fluorenyl, and naphthyl). Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. The term includes monocyclic or monocyclic-ring polycyclic (i.e., rings which share adjacent pairs of ring atoms) groups.

"Heteroalkyl" "heteroalkenyl" and "heteroalkynyl" include optionally substituted alkyl, alkenyl and alkynyl radicals and which have one or more skeletal chain atoms selected from an atom other than carbon, e.g., oxygen, nitrogen, sulfur, phosphorus or combinations thereof. A numerical range may be given, e.g. $C_1$-$C_4$ heteroalkyl which refers to the chain length in total, which in this example is 24 atoms long. For example, a —$CH_2OCH_2CH_3$ radical is referred to as a "$C_4$" heteroalkyl, which includes the heteroatom center in the atom chain length description. Connection to the rest of the molecule may be through either a heteroatom or a carbon in the heteroalkyl chain.

"Heteroaryl" or heteroaromatic refers to a 5, 6 or 10-membered aromatic radical (e.g., $C_5$-$C_{13}$ heteroaryl) that includes one or more ring heteroatoms selected from nitrogen, oxygen and sulfur, and which may be a monocyclic, bicyclic, tricyclic or tetracyclic ring system. Whenever it appears herein, a numerical range refers to each integer in the given range. An N-containing "heteroaromatic" or "heteroaryl" moiety refers to an aromatic group in which at least one of the skeletal atoms of the ring is a nitrogen atom. The polycyclic heteroaryl group may be monocyclic or non-monocyclic. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to adeninyl, azabenzimidazolyl, azaindolyl, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzofuranonyl, benzofurazanyl, benzothiazolyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, imidazopyridinyl, isoxazolopyridinyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thianaphthalenyl, thiapyranyl, triazolyl, tetrazolyl, triazinyl, thieno[2,3-d]pyrimidinyl, thieno[3,2-d]pyrimidinyl, thieno[2,3-c]pyridinyl, and thiophenyl (i.e., thienyl), xanthinyl, guaninyl, quinoxalinyl, and quinazolinyl groups.

"Heterocyclic" refers to any monocyclic or polycyclic moiety comprising at least one heteroatom selected from nitrogen, oxygen and sulfur. As used herein, heterocyclyl moieties can be aromatic or nonaromatic. The moieties heteroaryl and heterocyclyl alkyl are members of the heterocyclic group.

Zeta potential relating to pigment microparticles means the electrokinetic potential of extremely small particles suspended in colloidal dispersions. It is caused by the net electrical charge at the particle interface with the suspending fluid. It is an indicator of the stability of a colloidal dispersion. The magnitude indicates the degree of electrostatic repulsion between adjacent similar charged particles in a dispersion. At zero or minimal+ or − potential, rapid coagulation can occur. At a + or − zeta potential above about 40, good colloidal stability is maintained. Zeta potential can be measured using approaches known to those skilled in the art. For example, a Zetasizer Nano Z from Malvern Panalytical may be used to assess the zeta potential of the components.

The term "textile" as used herein has its ordinary and customary meaning and includes cloth, fabric or other material made out of natural plant fibers, synthetic fibers, metal fibers, carbon fibers, animal fibers such as may be derived from feathers, sinew, ligament, muscle and/or bone. The fibers are combined by weaving, felting, gluing, tacking, spinning, extruding, blow melting or other-wise formed into at least a somewhat coherent mass typically considered to be cloth, fabric, sponge rubber, foam, woven or nonwoven material. Rugs, bedsheets, clothing, coats, hats, underwear, socks, seat covers, seat cushions, pillows, and similar materials are textiles. Included also is paper made of plant or synthetic material such as typing paper, writing paper, foil, parchment papers, wax paper, aluminum foil and similar flat, thin materials.

DETAILED DESCRIPTION

Aspects of the present invention generally relate to disadvantages of known technologies for coloration of treated material, especially keratin material such as but not limited to hair by limiting damage to keratin proteins within the material, particularly after repeated dying events; facilitating the quantitative or substantially quantitative on demand removal of the color; limiting quick or inconsistent wash-out of the coloring means; limiting the potential for temporary irritation of the scalp upon applying known compositions (e.g., containing hydrogen peroxide at and an elevated pH); and shortening at least one of the treatment process and post-treatment processes, including drying time. In sum, the present invention is directed to compositions for coloration of treated material in such a way that the color can be applied and remain on the treated material until it is desired to remove the color. This makes the treatment process more pleasurable for the user and or stylist. It is also desired that the results are predictable, enabling the user to achieve their target hair color result.

The composition, method and coating aspects of the invention are directed to embodiments of a bicomponent composition that are adapted to provide colored coating embodiments on the surfaces of treated material such as but not limited to hair strands. The colored coating embodiments have "color fastness" or remanence that enables them to remain in somewhat to substantial original composition on the treated material through at least a series of washings with aqueous media containing soap and/or shampoo. Yet by manipulation of the triggering formulation according to the invention, the coating embodiments can be removed from the treated material to leave it in its substantially to essentially natural state before application of the bicomponent composition to the treated material. The bicomponent composition embodiments minimally alter treated material upon their application thereon and the embodiments of the method of application may be accomplished in short times.

The embodiments of the bicomponent composition according to the invention comprise first and second components formulated to provide the desired coloration of treated material, to provide the desired remanence and to provide the ability for removal without damage to the treated material. Sequential application of the first and second components will provide the desired benefits. Pretreatment of the treated material with the second component followed by application of the first component delivers the results for remanence and appropriate quality parameters especially for the treated material. The combination of the two components of the bicomponent composition in the aspect of use and application to treated material provides an unexpected synergy in delivering outstanding properties of remanence and tactile quality for the colored coating on treated material.

A. The Bicomponent Composition

First Component: Organic Polymer

The organic polymer of the first component of the bicomponent composition includes homopolymer, copolymer or terpolymer embodiments. These embodiments comprise oligomers and polymers of appropriate monomeric units such as but not limited to one or more olefin monomers, ester units of diacids/diol monomers, ester units of hydroxy acid monomers, ether monomeric units, thioether monomeric units, polyol monomeric units, alkylene oxide monomeric units, alkylene imine monomeric units, urethane monomeric units urea monomeric units, amide units of diacid/diamine monomers, amide units of amino acid monomeric units, amino acid units providing peptides, gelatin or biopolymers; carbohydrate monomeric units providing alginates, cellulosic derivatives, polysaccharides; as well as other repeating residues based on carbon or carbon in combination with other atoms such as oxygen and/or nitrogen, and any combination thereof. Preferably the oligomers and polymers are polyolefins, polyesters, polyethers, polyurethanes or polyamides or any combination thereof. More preferably, the oligomers and polymers are polyolefins, polyesters or polyurethanes or any combination thereof. Especially more preferably, the oligomers and polymers are polyolefins or polyesters.

The organic polymer may have any kind of pendant moiety including non-polar, aprotic, polar or protic groups (hereinafter functional groups) joined to the polymer backbone through connecting moieties such as but not limited to linear, branched or cyclic aliphatic moieties. The functional groups include oxygen, nitrogen, ester, oxycarbonyl, amide, carboxyl, hydroxyl, mercapto, thioether, ether, amino, imino, sulfonyl, sulfinyl and similar groups within or along the connecting moieties. These connecting moieties also include aromatic groups, heteroaromatic groups, small to oligomeric repeating carbon units, all with the same optional heteroatoms and heteroatom groups described for the alkyl chains and/or moieties. These connecting moieties may also be oligomeric or polymeric silicone moieties constructed of organosiloxane units.

Organic Polymers

Embodiments of the organic polymers for the first component can be conceptualized as classes, subclasses and categories of organic polymers with functional groups. These organic polymers include but are not limited to oligomers and polymers of appropriate monomeric units such as but not limited to one or more olefin monomers, ester units of diacids/diol monomers or of hydroxy acid monomers, ether monomeric units, thioether monomeric units, polyol monomeric units, alkylene oxide monomeric units, alkylene imine monomeric units, urethane monomeric units urea monomeric units, amide units of diacid/diamine monomers or of amino acid monomeric units, amino acid units providing peptides, gelatin or biopolymers; carbohydrate monomeric units providing alginates, cellulosic derivatives, cellulose esters, polysaccharides; hydroxylated polyester, acrylate functionalized polyester, polyester polyurethane acrylic copolymer, polyurethane-polyglycol copolymer, polycarbonate diols, styrene-allyl alcohol copolymer, ketone resins; as well as other repeating residues based on carbon or carbon in combination with other atoms such as oxygen and/or nitrogen, and any combination thereof. Additional organic polymers include but are not limited to non-polar olefinic polymers, polar, non-protonic olefinic polymers, vinyl polymers, polyethers, polycondensates, block polymers and any compound with repeating carbon unit residues. Preferably the organic polymers are polyolefins including polyvinyl compounds, polyesters, polyethers, polyurethanes or polyamides or any combination thereof. More preferably, the organic polymers are polyolefins including polyvinyl compounds, polyesters or polyurethanes or any combination thereof. Especially more preferably, the organic polymers are polyolefins, polyvinyl compounds or polyesters.

Organic polymers containing acid groups may be developed from any monomeric unit containing acid groups such as carboxylic acid, sulfonic acid, sufinic acid, phosphoric acid. The acidic units may be combined with non acidic units which are hydrophilic or hydrophobic to provide appropriate precursor organic polymers. Such polymers are described in the following passages.

Polymers may include copolymers of (meth)acrylic acid and of at least one linear, branched or cyclic (cycloaliphatic or aromatic) (meth)acrylic acid ester monomer and/or of at least one linear, branched or cyclic (cycloaliphatic or aromatic) mono- or disubstituted (meth)acrylic acid amide monomer.

Included are copolymers such as acrylic acid/ethyl acrylate/N-tert-butylacrylamide terpolymers such as the product sold under the name Ultrahold 8 and that sold under the name Ultrahold Strong by the company BASF; (meth) acrylic acid/tert-butyl (meth)acrylate and/or isobutyl (meth) acrylate/C1-C4 alkyl (meth)acrylate copolymers such as the acrylic acid/tert-butyl acrylate/ethyl acrylate terpolymer sold by the company BASF under the name Luvimer 100P; (meth)acrylic acid/ethyl acrylate/methyl methacrylate terpolymers and tetrapolymers such as the ethyl acrylate/methyl methacrylate/acrylic acid/methacrylic acid copolymer such as the product sold under the name Amerhold DR-25 by the company Amerchol; methyl methacrylate/butyl or ethyl acrylate/hydroxyethyl or 2-hydroxypropyl acrylate or methacrylate/(meth)acrylic acid tetrapolymers such as the methyl methacrylate/butyl acrylate/hydroxyethyl methacrylate/methacrylic acid tetrapolymers sold by the company Rohm & Haas under the name Acudyne 255.

Additional examples of organic polymers include copolymers of acrylic acid and of C1-C4 alkyl methacrylate and terpolymers of vinylpyrrolidone, of acrylic acid and of C1-C20 alkyl, for example lauryl, methacrylate, such as that sold by the company ISP under the name Acrylidone M and the copolymer of methacrylic acid and of ethyl acrylate sold under the name Luvimer MAEX by the company BASF.

Yet other examples of organic polymers include ampho-teric copolymers such as N-octylacrylamide/methyl methacrylate/hydroxypropyl methacrylate/acrylic acid/tert-butylaminoethyl methacrylate copolymers, in particular that sold under the name Amphomer by the company National Starch, or the copolymer Lovocryl L47 sold by the same company.

Additional examples of organic polymers include copolymers of (meth)acrylic acid and of (meth)acrylic acid esters or amides furthermore containing linear, branched or cyclic (cycloaliphatic or aromatic, which may or may not be substituted) vinyl esters, such as vinyl acetate; vinyl propionate; vinyl esters of branched acid such as vinyl versatate; vinyl esters of substituted or unsubstituted benzoic acid; these copolymers may furthermore also contain groups resulting from the copolymerization with styrene, alpha-methylstyrene or a substituted styrene. Other examples include copolymers of (meth)acrylic acid and of at least one olefinic monomer chosen from vinyl esters such as those mentioned above and containing no (meth)acrylic acid acrylamide or ester monomer. These copolymers may also contain olefinic groups resulting from the copolymerization with styrene, .alpha.-methylstyrene, a substituted styrene and optionally monoethylenic monomers such as ethylene.

Still other examples include copolymers of vinyl monoacid such as crotonic acid and vinylbenzoic acid and/or of allylic monoacid such as allyloxyacetic acid.

Organic polymers include copolymers of crotonic acid containing vinyl acetate or propionate units in their chain and optionally of other monomers such as allylic or methallylic esters, vinyl ethers or vinyl esters of a saturated, linear or branched carboxylic acid containing a long hydrocarbon chain, such as those containing at least 5 carbon atoms, it being possible for these polymers optionally to be grafted and crosslinked, or alternatively a vinyl, allylic or methallylic ester of an alpha- or beta-cyclic carboxylic acid. These copolymers may also contain olefinic groups resulting from the copolymerization with styrene, .alpha.-methylstyrene, a substituted styrene and optionally monoethylenic monomers such as ethylene.

Organic polymers include vinyl polymers such as vinyl acetate/crotonic acid/polyethylene glycol copolymers such as that sold by the company Hoechst under the name "Aristoflex A"; vinyl acetate/crotonic acid copolymers such as that sold by the company BASF Additional examples of precursor organic polymers include the polyolefins, polyvinyls, polyesters, polyurethanes, polyethers, polycondensates and natural polymers.

Additional examples of organic polymers include the polyolefins, polyvinyls, polyesters, polyurethanes, polyethers, polycondensates and natural polymers of the following passages.

Additional embodiments of the organic polymers include but are not limited to homopolymers and copolymers of olefins; cycloolefins; butadiene; isoprene; styrene; vinyl ethers, esters, or amides; (meth)acrylic acid esters or amides containing a linear, branched, or cyclic C1-C24 alkyl group, a C6-C24 aryl group or a C2-C24 hydroxyalkyl group. These polymers may be obtained from monomers such as isooctyl(meth)acrylate, isononyl(meth)acrylate, 2-ethylhexyl(meth)acrylate, lauryl(meth)acrylate, isopentyl(meth) acrylate, n-butyl(meth)acrylate, isobutyl(meth)acrylate, ethyl(meth)acrylate, methyl(meth)acrylate, tert-butyl(meth) acrylate, tridecyl(meth)acrylate, stearyl(meth)acrylate, hydroxyethyl(meth)acrylate, 2-hydroxypropyl(meth)acrylate, benzyl acrylate, phenyl acrylate, and mixtures thereof. Amides monomers include but are not limited to (meth) acrylamides, such as N-alkyl(meth)acrylamides, for example of a C2-C12 alkyl, such as N-ethylacrylamide, N-t-butylacrylamide, and N-octylacrylamide; N-di(C1-C4) alkyl (meth)acrylamides and perfluoroalkyl(meth)acrylates.

Embodiments of the organic polymers may also include incorporation of or attachment of a vinyl group to a diverse number of compounds. Polymerization delivers the polyvinyl compound (e.g., a version of polyolefins) with a large variation of substituent identity. Examples of vinyl monomers for such polymerization include but are not limited to vinyl alkanoate such as vinyl acetate, N-vinylpyrrolidone, vinylcaprolactam, vinyl N—(C1-C6)alkylpyrroles, vinyloxazoles, vinylthiazoles, vinylpyrimidines, vinyl pyridine, vinyl thiophene, and vinylimidazoles, olefins such as ethylene, propylene, butenes, isoprene, and butadienes.

Embodiments of organic polymers also include but are not limited to, for example, of the alkyl acrylate/cycloalkyl acrylate copolymer, the acrylates/C12-22 alkyl methacrylate copolymer and vinylpyrrolidone copolymers, such as copolymers of a C2-C30 alkene, such as a C3-C22 alkene, and combinations thereof. VP copolymers include but are not limited to VP/vinyl laurate copolymer, the VP/vinyl stearate copolymer, the butylated polyvinylpyrrolidone (PVP) copolymer, the VP/hexadecene copolymer, the VP/eicosene copolymer, the VP/triacontene copolymer or the VP/acrylic acid/lauryl methacrylate copolymer, octylacrylamide/acrylates/butylaminoethyl methacrylate copolymer, acrylates/octylacrylamide copolymer, polymers bearing fluoro groups belonging to one of the classes described in the above text, and the copolymers of alkyl(meth)acrylate/perfluoroalkyl (meth)acrylate. Additional organic polymers include those resulting from the polymerization or copolymerization of an ethylenic monomer, comprising at least one ethylenic bond, which can be, for example, conjugated (or dienes). organic polymer resulting from the polymerization or copolymerization of an ethylenic monomer, vinyl, acrylic, or methacrylic copolymers are also included without limitation.

organic polymers as block copolymers are also included, examples of which include but are not limited to a block copolymer comprising at least one block comprising styrene units or styrene derivatives (for example methylstyrene, chlorostyrene, or chloromethylstyrene). The copolymer comprising at least one styrene block may also comprise, for example, an alkylstyrene (AS) block, an ethylene/butylene (EB) block, an ethylene/propylene (EP) block, a butadiene (B) block, an isoprene (I) block, an acrylate (A) block, or a methacrylate (MA) block, or a combination of these blocks. The copolymer comprising at least one block of styrene units or styrene derivatives may be a diblock or triblock copolymer, for example of the polystyrene/polyisoprene or polystyrene/polybutadiene type, those of the polystyrene/copoly(ethylene-propylene) type or alternatively of the polystyrene/copoly(ethylene/butylene) type as well as styrene-methacrylate copolymers.

Further embodiments of organic polymers include but are not limited to those chosen from copolymers of vinyl ester (the vinyl group being directly connected to the oxygen atom of the ester group and the vinyl ester having a saturated, linear or branched hydrocarbon-based radical of 1 to 19 carbon atoms bonded to the carbonyl of the ester group) and of at least one other monomer chosen from vinyl esters (other than the vinyl ester already present), α-olefins (containing from 8 to 28 carbon atoms), alkyl vinyl ethers (in which the alkyl group contains from 2 to 18 carbon atoms), or allylic or methallylic esters (containing a linear or branched saturated hydrocarbon-based radical of 1 to 19 carbon atoms, bonded to the carbonyl of the ester group).

Further non-limiting examples of the organic polymers include the following copolymers: vinyl acetate/allyl stearate, vinyl acetate/vinyl laurate, vinyl acetate/vinyl stearate, vinyl acetate/octadecene, vinyl acetate/octadecyl vinyl ether, vinyl propionate/allyl laurate, vinyl propionate/vinyl laurate, vinyl stearate/1-octadecene, vinyl acetate/1-dodecene, vinyl stearate/ethyl vinyl ether, vinyl propionate/cetyl vinyl ether, vinyl stearate/allyl acetate, vinyl 2,2-dimethyloctanoate/vinyl laurate, allyl 2,2-dimethylpentanoate/vinyl laurate, vinyl dimethylpropionate/vinyl stearate, allyl dimethylpropionate/vinyl stearate, vinyl propionate/vinyl stearate, vinyl dimethylpropionate/vinyl laurate, vinyl acetate/octadecyl vinyl ether, vinyl acetate/allyl stearate, vinyl acetate/1-octadecene and allyl propionate/allyl stearate.

Additional embodiments of the organic polymers include polyalkenes and copolymers of C2-C20 alkenes, for example polybutene, polymers of natural origin, which are optionally modified, chosen from shellac resin, sandarac gum, dammar resins, elemi gums, copal resins, and polysaccharides comprising alkyl (ether or ester) side chains, for example alkylcelluloses containing a linear or branched, saturated, or unsaturated C1-C8 alkyl radical, such as ethylcellulose and propylcellulose.

Embodiments of the organic polymers may be of natural origin and may be chosen, for example, from cellulose-based polymers such as nitrocellulose, cellulose acetate, cellulose acetobutyrate, or cellulose acetopropionate. Non-limiting examples include the ethylcellulose the cellulose acetobutyrate, and the cellulose acetopropionates.

Embodiments of the organic polymers also include but are not limited to polycondensates which include but are not limited to polyurethanes, polyurethane-acrylics, polyurethane-polyvinylpyrrolidones, polyester-polyurethanes, polyether-polyurethanes, polyureas, polyurea-polyurethanes, and mixtures thereof. The polyurethanes may be, for example, a copolymer of aliphatic, cycloaliphatic, or aromatic polyurethane, or of polyurea-polyurethane.

The polyurethanes may also be obtained from branched or unbranched polyesters or from alkyds comprising mobile hydrogens that are modified via a polyaddition with a diisocyanate and an organic difunctional (for example dihydro, diamino or hydroxy-amino) coreagent.

Non-limiting examples of organic polymer may also include polyesters, polyester amides, fatty-chain polyesters, polyamides, and epoxyester resins. The polyesters may be obtained in a known manner via the polycondensation of aliphatic or aromatic diacids with aliphatic or aromatic diols or with polyols. Succinic acid, glutaric acid, adipic acid, pimelic acid, suberic acid, or sebacic acid may be used as aliphatic diacids. Terephthalic acid or isophthalic acid, or even a derivative such as phthalic anhydride, may be used as aromatic diacids. Ethylene glycol, propylene glycol, diethylene glycol, neopentyl glycol, cyclohexanedimethanol, and 4,4-N-(1-methylpropylidene)bisphenol may be used as aliphatic diols.

The polyesteramides may be obtained in a manner similar to that for the polyesters, via the polycondensation of diacids with amino alcohols. The polyamides may be obtained in a manner similar to that for the polyesters, via the polycondensation of diacids with diamines. Exemplary polyesters that may be mentioned include aliphatic polyesters containing C4-50 alkyl side chains or polyesters resulting from the condensation of fatty acid dimers, or alternatively polyesters comprising a silicone segment in the form of a terminal block, graft, or group.

Embodiments of Classes of the Organic Polymer

Embodiments of the organic polymer of the first component comprise one or more of the above described organic polymers with functional groups, especially polyolefins, polyvinyls, polyesters, polyethers, polyamides, polyurethanes and combinations thereof. Especially preferred are polyolefins, polyvinyls, polyesters, polyurethanes and polyethers. More especially preferred are polyolefins, polyvinyls and polyesters. The resulting organic polymer may comprise very low to very slight to moderate to substantial water solubility or dispersibility because of the presence of the functional groups. In some instances, the water solubility or dispersibility may be negligible. Although it is not a limitation of the invention, it is believed that when the organic polymer has negligible water solubility or dispersibility, its combination with the base compound to form a remanent coating may not be as efficient as can occur with better water solubility or dispersibility of the organic polymer.

Embodiments of the organic polymer may be selected from oligomers and polymers produced from monomers or monomeric units of one or more olefin monomers, ester units of diacids/diol monomers or of hydroxy acid monomers, ether monomeric units, thioether monomeric units, polyol monomeric units, alkylene oxide monomeric units, alkylene imine monomeric units, urethane monomeric units, urea monomeric units, amide units of diacid/diamine monomers or of amino acid monomeric units, amino acid units providing peptides, gelatin or biopolymers; carbohydrate monomeric units providing alginates, cellulosic derivatives or polysaccharides; as well as other repeating residues based on carbon or carbon in combination with other atoms such as oxygen and/or nitrogen, and any combination thereof. The organic polymer may comprise a polyolefin, a polyester, a hydroxylated polyester, an acrylate functionalized polyester, a polycarbonate, a polyallyl alcohol, a ketone resin, a polyether, a polyimine, a polyurethane, a polyurea, a polyglycol, a polyamide, a polypeptide, a carbohydrate compound, a cellulose, a cellulose derivative such as a cellulose ester or a hydroxylated cellulose or a carboxyl cellulose or a hydroxyl cellulose ester or carboxylic acid, an alginate, a gum, a polysaccharide, an amino acid polymer, a gelatin, an oligopeptide, a polypeptide or a protein, a carbohydrate-amino acid such as a glycosylated peptide or a carbohydrate-purine/pyrimidine base such as a polynucleoside, a biopolymer, a (meth)acrylic copolymer, a crotonic copolymer, a polyurethane-polyglycol copolymer, a polycarbonate diol, a styrene-allyl alcohol copolymer, a polyol, a natural gum, polyvinyl acetate, polyvinylpyrrolidone, polynipam, a polymer based on one or more olefin monomers, a polymer based on ester units of diacids/diol monomers, a polymer based on ester units of hydroxy acid monomers, a polymer based on ether monomeric units, a polymer based on thioether monomeric units, a polymer based on polyol monomeric units, a polymer based on alkylene oxide monomeric units, a polymer based on of alkylene imine monomeric units, a polymer based on urethane monomeric units, a polymer based on urea monomeric units, a polymer based on amide units of diacid/diamine monomers, a polymer based on amide units of amino acid monomeric units or other polymer having repeating residues based on carbon or carbon in combination with other atoms such as oxygen and/or nitrogen, and any combination thereof. Preferred organic polymers include polyolefins, polyvinyls, polyesters, polyethers, polyamides, polyurethanes and combinations thereof. Especially preferred organic polymers include polyolefins, polyvinyls, polyesters, polyurethanes and polyethers and combinations thereof. More especially preferred organic polymers include polyolefins, polyvinyls and polyesters and combinations thereof.

The organic polymer may have pendant moieties appended to the polymer backbone such as esters, ethers, oxycarbonyls, amides, aliphatic groups, aromatic groups, linear, branched or cyclic alkyl groups or similar groups that are other than polar and protic. Examples of pendant moieties include but are not limited to such moieties as an alkyl carboxyl ester resulting from polymerization of an alkyl (meth)acrylate, or phenyl resulting from polymerization of styrene.

The functional groups of the organic polymer may be arranged as pendant groups, arranged as terminal groups or may be a combination thereof. The functional groups may include oxygen, nitrogen, ester, oxycarbonyl, amide, thioamide, thioester, carboxyl, hydroxyl, mercapto, thioether, ether, amino, imino, sulfonyl, sulfinyl and similar groups within or along the connecting moieties. The preferred functional groups may be polar and/or protic groups including but not limited to carboxylic acid groups, hydroxyl groups, amine groups, mercapto groups (i.e., thiol, —SH), sulfo acid groups ($HO_3S$—), sulfino acid groups ($HO_2S$—), or any combination thereof. Not all organic polymer molecules may bear the same number of functional groups.

The functional groups may be covalently linked to the polymer backbone through any manner of carbon-carbon or carbon-silicon connection arrangements or units. These carbon and/or silicon connection arrangements may be but are not limited to a carbon connection unit comprising a linear, branched or cyclic C1-C24 alkylenyl, oxyalkyenyl, alkylenyloxy or oxyalkylenyloxy unit, a C2-C24 alkanoyl or oxyalkanoyl unit, a C6-C24 aromatic or oxyaromatic unit, a C5-C24 heteroaromatic or oxyheteroaromatic unit having one or two heteroatoms selected from nitrogen, oxygen and sulfur, a $(C_z$—$O$—$C_z)_n$ polyether unit wherein z is an integer of 1 to 6 and n is an integer of 2 to 6, a $(C_y$—$NH$—$C_y)_m$ polyimino unit wherein y is an integer of 1 to 6 and m is an integer of 2 to 6. The recitation of "oxy" before or after an organic group means that the organic group such as alkylenyl is connected to the polymer chain through an oxygen. For example, an alkylenyl group is connected to the polymer chain by a carbon-carbon bond while an oxyalkylenyl group is connected to the polymer chain by a carbon-oxygen bond.

Alternatively the functional groups may be covalently linked to the organic polymer through a linear or branched silicon connection unit comprising a Si1-Si24 organosiloxane moiety (as $R_2SiO_2$ monomeric residues) having methyl as the organo group with silicon of the connection unit bonded to the functional group through an alkylenyl group of one to three carbons or through an oxyalkylenyl group of one to three carbons or through an oxyalkylenyloxy group of one to three carbons and combinations thereof. The carbon and/or silicon connection arrangements are covalently bound to the organic polymer backbone and to the functional groups.

These embodiments of the organic polymer have functional groups that are compatible with each other and other substituents of the organic polymer.

The Organic Polymer of Hydrophobic and Hydrophilic Monomers

Representative embodiments of some classes of the organic polymer comprise repeating units of a hydrophobic monomer or a hydrophilic monomer or a combination thereof, preferably a combination of the hydrophobic monomer and the hydrophilic monomer.

The hydrophobic monomer of this organic polymer embodiment may be selected from one or more of an olefinic carboxylate ester monomer or an olefinic carboxamide monomer, an olefinic sulfonamide monomer or any combination thereof. The olefinic carboxylate ester comprises an ester of an olefinic carboxylic acid and at least one saturated linear or branched C1 to C24 primary or secondary alcohol or a C4 to C24 cyclic or alkylcyclic alcohol. The olefinic carboxamide monomer comprises an amide of an olefinic carboxylic acid and ammonia or at least one linear or branched C1 to C24 primary amine. The olefinic sulfonamide monomer comprises an amide of an olefinic sulfonic acid and ammonia or at least one linear or branched C1 to C24 primary amine or a cyclic or alkylcyclic C4 to C24 alcohol.

The olefin monomer of this organic polymer embodiment has the formula: $H_2C=CHR$ wherein R is selected from hydrogen, linear or branched alkyl of one to twenty four carbons, unsubstituted phenyl or phenyl substituted by one or more linear or branched alkyl of 1 to twenty four carbons, carboxylic ester of an linear or branched C1 to C214 alkanol, carboxamide of ammonia or a linear or branched C1 to C24 primary amine, sulfonamide, sulfinamide, or R is selected from $-CR^2=CHR^1$ wherein $R^1$ is hydrogen, methyl, ethyl or phenyl and $R^2$ is hydrogen or methyl.

The hydrophilic olefinic monomer of this embodiment of the organic polymer may be selected from:

(i) a hydroxyl ester of an olefinic carboxylic acid and a linear or branched alkyl diol of 2 to 24 carbons or a cyclic alkyl diol of 5 to 24 carbons;

(ii) an aminoalkyl ester of an olefinic carboxylic acid and a linear or branched C2-C24 aminoalkyl alcohol or a cyclic C5-C24 aminoalkyl alcohol; (ii) a mercaptoalkyl ester of an olefinic carboxylic acid, and a linear or branched C2-C23 mercaptoalkyl alcohol or a cyclic C5-C24 mercaptoalkyl alcohol;

(iii) an olefinic acid;

(iv) vinyl alcohol;

(v) a polar olefinic compound of the formula $H_2C=CHC_6H_4R$ wherein R is selected from selected from hydroxy, sulfonic acid, sulfinic acid, carboxylic acid, or a polyester polyol group having terminal and/or pendant hydroxyl groups; or, (viii) any combination of multiples of the hydroxyl ester, the aminoalkyl ester, the mercaptoalkyl ester, the olefinic acid, the vinyl alcohol, or the polar olefinic compound.

The olefinic carboxylic acid of this embodiment of the organic polymer is an alkenoic acid of 3 to 24 carbons or alkendioic acid of 4 to 24 carbons or partially hydrolyzed polyacrylonitile or any combination thereof.

This embodiment of the organic polymer comprises at least two pendant or terminal or pendant and terminal and preferably multiple functional groups which are selected from a hydroxyl group, a carboxylic acid group, a sulfonic acid group, a sulfinic acid group, an amine group, a mercapto group, or a combination thereof.

Additional embodiments of the organic polymer may include polymers of olefinic carboxylic acids such as (meth) acrylic acid, crotonic acid, pentadienoic acid (butadienyl carboxylic acid) optionally combined with olefinic acid esters and amides and neutral olefinic monomers. The organic polymer may include units of olefinic carboxylic acid monomers including (meth)acrylic acid, maleic acid, fumaric acid, itaconic acid, crotonic acid, pentenoic acid pentadienoic acid, isoprenoic acid, partially hydrolyzed polyacrylonitile and optional olefinic acid monomer derivatives that are homologs of these olefinic carboxylic acid monomers. The organic polymer may include units of the foregoing olefinic carboxylic acid monomers and in addition may include one or more monomeric units of esters of olefinic carboxylic acid monomers wherein the esterifying alcohol is a linear, branched or cyclic alkyl monoalcohol or diol of 1 to 12 carbons for the linear alkyl group (2 to 12 carbons for the diol), 3 to 12 carbons for the branched alkyl group and 3 to 12 carbons for the cyclic alkyl group, amides of said olefinic carboxylic acid monomers. N-alkyl amides of the olefinic carboxylic acid monomers wherein the alkyl group is a linear, branched or cyclic alkyl group as described for the monoalcohol, N-aminoalkyl amides of the olefinic carboxylic acid monomers wherein the amidating amine is a linear, branched or cyclic alkyl diamine with 2 to 12 carbons in the linear alkyl group, 3 to 12 carbons in the branched alkyl group and 3 to 12 carbons in the cyclic alkyl group. Neutral olefinic monomers including those of the formula: $HR'C=CHR^2$ or $HR'C=CH-CR^3=CHR^4$ wherein $R^1$, $R^2$, R3 and $R^4$ are each independently selected from hydrogen, linear alkyl of 1 to 6 carbons, branched alkyl of 3 to 6 carbons, cyclic alkyl of 3 to 10 carbons, phenyl, phenyl substituted by methyl, ethyl, OH, $CONH_2$, COOH, $-(CH_2)_nCOOH$, $NO_2$, CN, $SO_3H$, $SONH_2$, pyridyl, $O_2CR'$ wherein R' is alkyl of 1 to 3 carbons, vinyl and alkyl vinyl having 1 to 3 carbons in the alkyl group.

Preferred embodiments of the hydrophilic monomer of the organic polymer include olefinic carboxylic acids and sulfonic acids selected from one or more of (meth)acrylic acid, crotonic acid, pentenoic acid, hexenoic acid, maleic acid, fumaric acid, glutaconic acid, itaconic acid, citraconic acid, mesaconic acid, vinyl sulfonic acid or any combination thereof. More preferred olefinic carboxylic acids include (meth)acrylic acid, crotonic acid, vinyl sulfonic acid, maleic acid, fumaric acid and itaconic acid. Most preferred olefinic carboxylic acids include (meth)acrylic acid, crotonic acid, maleic acid and itaconic acid. Especially preferred olefinic carboxylic acids include (meth)acrylic acid and crotonic acid.

Additional preferred embodiments of the hydrophilic monomer of the organic polymer alone or in combination with preferred olefinic carboxylic and sulfonic acids include the preferred hydroxyalkyl esters of the foregoing preferred acids esterified with a C2-C6 diol including ethylene diol, propylene diol, butylene diol, pentylene diol or cyclohexane diol aminoethanol, aminopropanol and aminobutanol. Especially preferred hydroxyalkyl esters include the more preferred olefinic carboxylic acids esterified with any of these C2-C6 diols. More preferred hydroxyalkyl esters include the most preferred olefinic carboxylic acids with ethylene diol, propylene diol or butylene diol.

Additional preferred embodiments of the hydrophilic monomer of the organic polymer alone or in combination with the preferred olefinic carboxylic and sulfonic acids or in combination with the preferred hydroxyalkyl esters or in combination with the preferred carboxylic and sulfonic acids and the preferred hydroxyalkyl esters includes the aminoalkyl esters of the preferred olefinic carboxylic and sulfonic acids esterified with a C2 C4 amino alcohol including amino ethanol, amino propanol and aminobutanol. More preferred aminoalkyl esters include the more preferred olefinic carboxylic acids esterified with amino ethanol or amino propanol.

Additional preferred embodiments of the hydrophilic monomer of the organic polymer alone or in combination with preferred olefinic carboxylic and sulfonic acids, or in combination with the preferred hydroxyalkyl esters or in combination with the preferred amino alkyl esters and with any combination thereof include the mercapto alky esters of the preferred olefinic carboxylic and sulfonic acids. The preferred mercapto alcohols for these esters include mercaptoethanol, mercaptopropanol and mercaptobutanol. More preferred mercaptoalkyl esters include the more preferred olefinic carboxylic acids esterified with mercaptoethanol.

Additional preferred embodiments of the hydrophilic monomer of the organic polymer alone or in combination with preferred olefinic carboxylic and sulfonic acids, or in combination with the preferred hydroxyalkyl esters or in combination with the preferred amino alkyl esters, or in combination with the preferred mercaptoalkyl esters and with any combination thereof include polar olefinic monomers selected from p-hydroxystyrene, styrene-p-carboxylic acid, o,p-dihydroxystyrene, styrene-p-sulfonic acid and any combination thereof.

Preferred embodiments of the hydrophobic monomer of the organic polymer include the alkyl esters wherein the preferred olefinic carboxylic and sulfonic acids are esterified with a C1 to C8 alcohol including methanol, ethanol, propanol, isopropanol, butanol, isobutanol, pentanol, isopentanol, hexanol, isohexanol, ethylhexanol, cyclohexyl alcohol. More preferred alkyl esters include the more preferred olefinic carboxylic acids esterified with ethanol, propanol, butanol, ethylhexanol or cyclohexyl alcohol. Most preferred alkyl esters include the most preferred olefinic carboxylic acids esterified with ethanol, butanol, ethylhexanol or cyclohexyl alcohol.

Additional preferred embodiments of the hydrophobic monomer of the organic polymer include non-polar olefin monomers selected from styrene, methylstyrene, ethylstyrene, propylstyrene, butadiene, 1-phenylbutadiene, isoprene or any combination thereof.

Preferred combinations of the recited species of the hydrophilic monomer and the hydrophobic monomer of the foregoing preferences include any combination of the recited preferred non-polar olefinic monomers, the recited preferred polar olefinic monomers, the recited preferred alkyl esters, the recited preferred hydroxyalkyl esters, the recited preferred aminoalkyl esters, the recited preferred mercapto alkyl esters and the preferred olefinic carboxylic and sulfonic acids. The choice of any combination of these species means selection of the first species of the preferred list of olefinic carboxylic and sulfonic acids, selection of the first species of the preferred list of hydroxy alkyl esters, selection of the first species of the preferred list of amino alkyl esters, selection of the first species of the preferred list of mercapto alkyl esters, selection of the first species of the preferred list of preferred polar olefinic monomers and selection of the first species of the preferred list of non-polar olefinic monomers and combining any two of the selections, any three of the selections, any four of the selections, any five of the selections or combining all six of the selections according to the parameters indicating the amounts of hydrophilic monomer and hydrophobic monomer are to be present in the organic polymer. The choice may also be made in a similar fashion by choosing any species from any preferred list and combining it with any species of any other list or multiple lists to provide all combinations of selections.

The organic polymer embodiments generally may have an acid value ranging from zero or 0.01 to about 700, preferably about 1 to about 500, more preferably 2 to 250, most preferably 7-90 with typical acid numbers below approximately 100. Typical hydroxyl content may average approximately 1 to 20 wt % or may be approximately 5-10 wt %. The organic polymer may have a weight average molecular weight in the range of about 2 KDa to about 2 MDa, preferably about 2 KDa to about 100 KDa, more preferably about 2 KDa to about 25 KDa. The organic polymer may have a glass transition temperature of from about −125° C. to about −40° C.

The organic polymer may be constructed with random distribution of the different monomer units along the polymer backbone or may be block copolymers which has blocks of single monomer units or may be a graft copolymer which has one monomer unit forming the polymer backbone and a different monomer unit forming polymeric side chains. The different constructions of polymer provide differing polymer to polymer binding properties and different macromolecular characteristics. The block copolymer can provide regions of hard and soft polymer characteristics. A block copolymer can display crystalline regions and amorphous regions that can enable development of water soluble and water resistant regions. Blocks of differing electronic and lipophilic character can impart an open repulsive character to the polymer so that tightly fit inter-structures are minimized. A grafted polymer or segmented polymer are capable of intertwined conformation and compact molecular dimension so as to enable tightly fitted inter-structures.

Additional organic polymer embodiments may comprise one or more monomer unit(s) comprising one or more functional group(s) selected from the group consisting of sulfate, sulfonate, carboxylate, phosphate, phosphonate groups and mixtures thereof as substitutes for the olefinic carboxylic acids of the hydrophilic monomer of the organic polymer. These monomer units may be combined with the other hydrophilic monomers and with the hydrophobic monomers described above to form additional embodiments of the organic polymer. The functional group(s) may preferably be selected from the group consisting of sulfate, sulfonate, carboxylate groups and mixtures thereof. Additionally, anionic polymers of such monomeric units may be combined with the organic polymer embodiments described above to form a mixture of anionic polymer and organic polymer.

The polymeric portions of these substitutes for the acidic hydrophilic units constitute monomers from anionic polymers selected from the group consisting of polystyrene sulfonate salts, λ-carrageenan salts, dextran sulfate salts, polyacrylic acid salts, poly(methacrylic acid) salts, alginic acid salts, carboxymethylcellulose salts, polystyrene sulfonate/polystyrene copolymer salts, copolymers thereof and mixtures thereof. The salts may be sodium salts.

Examples of the anionic polymer(s) from which such substitute acidic monomers may be selected may be but are not limited to embodiments including:

a) Polystyrene sulfonate (PSS) sodium salt of the formula:

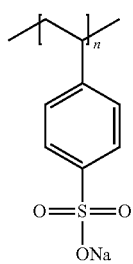

in which n is an integer representing the degree of polymerization, wherein n ranges from 50 to 20,000, alternatively from 150 to 500;

b) Co-polymer of polystyrene sulfonate (PSS) sodium salt and poly(4-styrenesulfonic acid-co-maleic acid) of the formula:

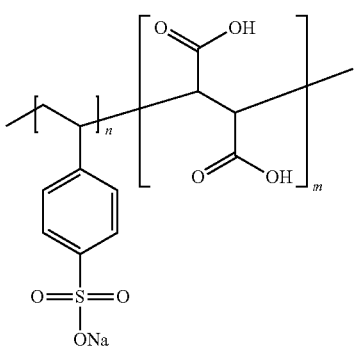

in which n and m are integers representing the degree of polymerization, wherein n+m ranges from 50 to 20,000, alternatively from 150 to 2500;
c) λ-Carrageenan;
d) Dextran sulfate sodium salt;
e) Polyacrylic acid (PAA) of the formula:

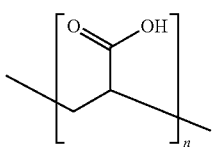

in which n is an integer representing the degree of polymerization, wherein n ranges from 50 to 20,000, alternatively from 150 to 5000;
f) Alginic acid sodium salt;
g) Carboxymethylcellulose sodium salt of the formula:

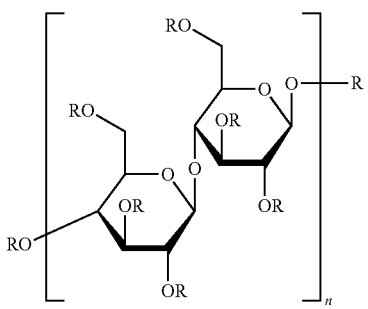

in which: R is H or $(CH_2)_2COONa$ and n is an integer representing the degree of polymerization; copolymers thereof and mixtures thereof.

These polymers and copolymer embodiment examples as well as the corresponding monomeric units may be random or block copolymers in combination with the hydrophobic monomers and hydrophilic monomers described above for the organic polymer except that these monomeric units may alternatively be substitutes for the olefinic carboxylic acids of the hydrophilic monomers of the organic polymer.

The Second Component

Embodiments of the second may combine with embodiments of the first component of the bicomponent composition to interact together (e.g., blend, combine, unite together as one) into a colored coating on treated material that displays significant remanence. Embodiments of the substantive feature of the second component are the base compound. Embodiments of the base compound incorporate amine groups into and onto an organic or silicone core or chain. The base compound preferably has a weight average molecular weight of about 150 Da to about 1 MDa. When the base compound is a polymer, preferably about 400 Da to about 500 KDa, more preferably about 400 Da to about 250 KDa, most preferably about 2 KDa to about 100 KDa.

Embodiments of the base compound as an organic core with amine groups may be one or more amine polymer(s). The amine polymer(s) may comprise one or more amino functional group(s) per polymer chain, wherein the amino functional group(s) are selected from the group consisting of primary, secondary, tertiary amino functional groups and mixtures thereof, preferably from the group consisting of secondary, tertiary amino functional groups and mixtures thereof.

Embodiments of the base compound may be selected from the group consisting of polyethyleneimine, polyallylamine hydrochloride, polydiallyldimethylammonium chloride, polyvinylamine, aminopolysaccharide, copolymers thereof and mixtures thereof. The cationic polymer(s) may preferably be selected from the group consisting of polyethyleneimine, aminosilicone, polydiallyldimethylammonium chloride, copolymers thereof and mixtures thereof.

Additional embodiments of the base compound include polymers with carboxylate groups, sulfonate groups, carbamate groups and mercaptan groups. Exemplary base compounds include polymercaptan compounds such as tri-(mercaptoethylenyl) methane, di, tri and poly sulfonate compounds such as tri-(sulfoethylenyl) methane, di, tri and poly carboxylate compounds such as adipic acid, citric acid and polyacrylic acid, and carbamate compounds such as tri-(methylcarbamoylethylenyl) methane.

Preferred base compounds are those carrying amine functionality. These embodiments of the base compound may be linear or branched and/or may be random or block copolymers.

As amine polymer(s) such as the embodiments of the base compound described above, exemplary selections include:
a) Linear polyethyleneimine of the formula:

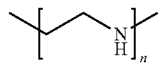

in which n is an integer representing the degree of polymerization, wherein n ranges from 5 to 25,000, alternatively from 11 to 2,500;
b) Branched polyethyleneimine consisting of primary, secondary and tertiary amine groups of the formula:

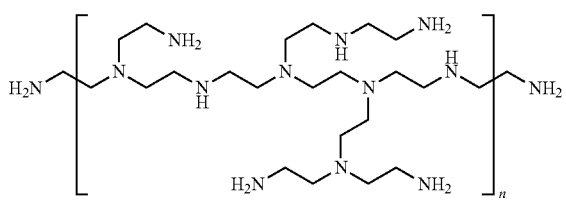

in which n is an integer representing the degree of polymerization, wherein n ranges from 2 to 4,000, alternatively from 5 to 500;

c) Polyallylamine hydrochloride of the formula:

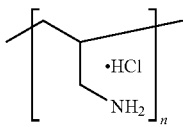

in which n is an integer representing the degree of polymerization, wherein n ranges from 50 to 20,000, alternatively from 5 to 1250;

d) Polydiallyldimethylammonium chloride of the formula:

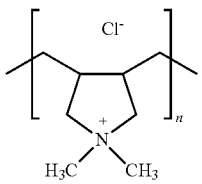

in which n is an integer representing the degree of polymerization, wherein n ranges from 10 to 20,000, alternatively from 150 to 4,000;

copolymers thereof and mixtures thereof.

These embodiments of the base compound, e.g., the amine polymer(s) may have a charge density when fully protonated of at least 0.3, preferably at least 0.6, more preferably at least 0.8, even more preferably at least 1.0 positive charges per monomer unit.

Embodiments of the base compound may also be amino silicone compounds. Embodiments of the amino silicone polymer base compound may comprise any silicone polymer chain that incorporates amine functional groups into the silicone polymer. The amino silicone compounds may also be aminosiloxane compounds or oligomers and aminosilane compounds.

A preferred silicone polymer is one having amine functional groups (hereinafter an aminosilicone polymer). The molar ratio of siloxane monomeric units with at least one pendant organic amine group (hereinafter SiA moieties) to siloxane monomeric units having silicon bonded to a substituent selected from the group consisting of alkyl (C1 to C6) (hereinafter SiC moieties) is in the range of from about 1:1000 to 1:10 (ratio of SiA units to SiC units), preferably 1:1000 to 1:25, more preferably 1:600 to 1:50, most preferably 1:400 to 1:75 or 1:300 to 1:200. An SiA moiety may contain more than one amine group in which case it counts as just one SiA moiety. An SiC moiety may contain any number of other pendant groups as long as a primary, secondary, tertiary or quaternary amine group is not present. The aminosilicone polymer may have a weight average molecular weight ranged from about 10 kDa to about 150 kDa, preferably about 18 kDa to about 130 kDa, more preferably about 22 kDa to about 120 kDa.

The amine functional groups of the aminosilicone polymer may be primary, secondary, tertiary amine groups or quaternary ammonium groups or any combination thereof. The secondary, tertiary or quaternary amine groups may be substituted by alkyl groups of 1 to 6 carbons, such as methyl, ethyl, propyl, butyl, pentyl or hexyl or any combination thereof. The amine functional groups may be organic pendant groups wherein the amine group terminates the end of the organic group. The pendant organic amine group is bonded to the silicone backbone by a carbon to silicon bond between the organic group and a siloxane monomeric unit as —O—Si(R')$_2$—O— wherein each R' is independently selected from a pendant organic amine group and an alkyl group of 1 to 6 carbons and at least one R' group is a pendant organic amine group. The organic amine group may be a linear alkyl group of 1 to 16 carbons or a branched or cyclic alkyl group of 3 to 16 carbons. The alkyl group may contain one or more heteroatoms and/or hetero-groups in the chain including such groups as —NH—, —O—, —S—, —CONH— or —NHCO—, —SO$_2$NH— or —NHSO$_2$—.

Typical pendant amine groups include such arrangements as:
(CH$_2$)$_3$—NH—(CH$_2$)$_3$NH$_2$, —CH$_2$—CH(CH$_3$)—CH$_2$—NH—(CH$_2$)$_3$NH$_2$
(CH$_2$)$_3$—CONH—(CH$_2$)$_3$NH$_2$, —(CH$_2$)$_3$—NHCO—(CH$_2$)$_3$NH$_2$ and
single amine groups such as —(CH$_2$)$_n$—NH$_2$ wherein n is 2 to 6, preferably 3 or 4 or branched chain versions thereof such as —CH$_2$—CH$_2$—CH$_2$—NH$_2$, —CH$_2$—CH(CH$_3$)—CH$_2$—NH$_2$.

The amine group or groups may be pendant to the silicone chain at uniform or random locations along and within the silicone chain. The amine functional group may also terminate the ends of the silicone chain but an aminosilcone polymer having terminal amine groups preferably will also have pendant amine groups along the silicone chain. If the aminosilicone polymer contains only terminal amine groups, its weight average molecular weight preferably will be low so that its SiA:SiC ratio will conform to the foregoing values.

The silicone chain of the aminosilicone polymer may be linear, branched or crosslinked. In addition to the SiA and SiC moieties, aminosilicone may also include any one or more of MDTQ groups of the formulas A, B, C and D wherein R is a methyl group:

A) —O(R)$_2$Si—O— (known as a D siloxane unit)
B) —O(R)SI(—O—)$_2$ or —O—Si(—O—)$_2$—O— (known as T siloxane unit and Q sesquisilicate unit respectively)
C) (R)$_3$SI—O— (known as M siloxane unit).

For this embodiment of the aminosilicone polymer component of the base compound the A), B), C) and D) groups constitute together the SiC moieties defined above. The A) group provides a linear silicone chain link, the B) group provides a branched or crosslinked silicone chain link, the C and D groups provide a silicone chain termination. The distribution of the SiA moiety and the A), B), C), and D) groups of the SiC moiety follows ordered or random arrangement and the SiA to SiC ratios and weight average molecular weight ranges given above.

Relationships and Preferences for the Components

An especially preferred embodiment of the organic polymer includes an organic polymer comprising the hydrophilic monomer as (meth)acrylic acid and hydroxyethyl or hydroxypropyl (meth)acrylate, the hydrophobic monomer as methyl or ethyl (meth)acrylate, and no olefin monomer such as styrene or detectable or moderate amount of olefin. An additional especially preferred embodiment of the organic polymer includes an organic polymer comprising the hydrophilic monomer as crotonic acid, hydroxyethyl crotonate or hydroxypropyl crotonate; the hydrophobic monomer as methyl or ethyl crotonate, and the no olefin monomer such as styrene or a detectable amount or a moderate amount of the olefin.

Additional preferred organic polymers include those constructed of monomeric units of alkyl (meth)acrylate or alkyl crotonate or a combination thereof with the alkyl group being 1 to 3 carbons; hydroxyalkyl (meth)acrylate or hydroxyalkyl crotonate or a combination thereof with the alkyl group being 1 to 3 carbons; (meth)acrylic acid or crotonic acid or any combination thereof; and optional styrene. The preferred embodiment of the base compound is polyethylene imine.

An especially preferred embodiment of the first and second components incorporates an organic polymer comprising monomeric units of alkyl (meth)acrylate, hydroxyalkyl (meth)acrylate and (meth)acrylic acid wherein the hydroxyl content ranges from 1 wt % to about 20 wt % with a preference of from 2 wt % to about 5 wt % and a typical weight percent of about 3.3 wt %. The acid number may be 7-90 with a typical acid number below approximately 100. The especially preferred embodiment also incorporates a pretreatment base compound of polyethylene imine.

An especially most preferred embodiment of the combination of the first and second components of the bicomponent composition includes the organic polymer as a copolymer of ethyl (meth)acrylate, C2-C6 hydroxyalkyl (meth)acrylate and about 0.1 to about 5 wt % of (meth)acrylic acid relative to the weight of the organic polymer and the base compound as polyethyleneimine.

The first and second components of these preferred embodiments include medium and either or both of the first and second components include pigment microparticles.

The organic polymer of this highly preferred embodiment comprises an organic polymer of the combination of hydrophobic monomers and hydrophilic monomers. The hydrophobic monomer comprises a C1-C24 alkyl linear or branched (meth)acrylate monomer or a C1-C24 alkyl linear or branched crotonate monomer or a combination thereof and optional styrene. The styrene may be absent or may be present up to a moderate amount such as up to 20 wt % or up to 50 wt % relative to the total weight of the organic copolymer. The hydrophilic monomer comprises an olefinic acid selected from (meth)acrylic acid or crotonic acid or a combination thereof, and a hydroxyalkyl olefinic ester selected from hydroxymethyl or hydroxyethyl (meth)acrylate or crotonate or any combination thereof. A preferable arrangement of this organic polymer comprises ethyl(meth)acrylate, hydroxyethyl (meth)acrylate and (meth)acrylic acid with optional styrene which may be absent or when present may be present at a weight percentage relative to the total weight of the organic polymer of from zero up to about 30 wt %. The $M_w$ of the organic polymer may be in the range of about 2 KDa to about 25 KDa. The acid number of the organic polymer is in a range of about 3 to about 150. The hydroxyalkyl olefinic ester portion of the organic copolymer is in a range of about 1-15 wt % preferably about 3 to 8 wt % relative to the total weight of the organic copolymer.

The base compound of this highly preferred embodiment is polyethyleneimine at a concentration of 0.1-5% in an aqueous medium relative to the total weight of the combination of the base compound and the medium. The base compound is arranged to be applied to the treated material as a pretreatment before application of the first component.

The medium for the organic polymer of this highly preferred embodiment is water. The pretreatment base compound is neat and is combined with the first component immediately before use. The weight percentage of the organic polymer and the pretreatment base compound is between 1-10 wt. % of the combined first and second components including the medium and pigment.

Viscosity, Composition Concentrations

The viscosity of the composition functions to hold the composition with pigment microparticles in place on the treated material while the coating is formed. The viscosity substantially avoids free translational flow of the composition. Free translation flow would cause the composition to rapidly run and drip off the surfaces of the hair strands. Nevertheless, the viscosity is not so high that it will not undergo self-leveling to substantially uniformly coat the treated material. Appropriate viscosity of the composition is the result of the interaction of the organic polymer, the base compound, their concentrations, the pigment microparticles, and as appropriate, an optional viscosity control agent, an optional suspending agent and an optional thickening agent. Generally, the viscosity of the composition may range from about 0.001 to about 2000 Pa s$^{-1}$. Viscosity measurements are carried out on a controlled stress rheometer e.g. Using an AR2000 type manufactured by TA Instruments, or equivalent instrument. A 6 cm flat acrylic cross hatched parallel plate geometry (TA item 518600.901) and a stainless steel cross hatched base plate (TA item 570011.001) are used. The rheometer is prepared for flow measurements as per standard manufacturer procedure. The parallel plate geometry gap is set to 1000 microns. The flow procedure is programmed to the rheometer with the following conditions: continuous stress ramp 0.1-300 Pa over 2 minutes at 25° C., including 250 measurement points in linear mode. The product is loaded into the geometry as per standard procedure and the measurement commences at 5 min after the mixture preparation. Shear stress value at 10 sec$^{-1}$ shear rate is obtained from the shear stress vs. shear rate curve, and the corresponding viscosity is calculated by dividing the obtained shear stress by 10.

The concentration of the organic polymer in the composition may range from about 2% to about 30%, preferably about 4% to about 25%, more preferably about 6% to about 20%, most preferably about 8% to about 15% by weight relative to the total weight of the composition. Specific concentrations include about 2%, about 4%, about 6%, about 8%, about 10%, about 12%, about 14%, about 16%, about 18%, about 20%, about 22% about 24% by weight relative to the total weight of the composition. The determination of the concentration for embodiments of the organic polymer and pretreatment base compound will depend in part upon the resulting viscosity, the saturation point of the organic polymer in the medium. As discussed above, the viscosity is managed so that the composition will not run off the surfaces of strands of hair yet will level and flow to substantially coat those surfaces. Development of appropriate viscosity in part by management of the concentration of the organic polymer can be experimentally determined by routine methods such as formulation of several samples of differing concentrations of polymer in the composition, coating those samples on a hair tress and observing the flow, spread and leveling of the composition on the hair strands. The product can be applied to a treated material such as a hair tress using the coloring procedure described herein afterwards. The top of the hair strand, where it is glued together is clamped in a stand such that the hair is aligned vertically downwards. After a 5 minute dwell time it is observed if any and how much product has dripped from the hair tress. The results obtained from the several samples can be plotted against flow time and leveling time to determine an appropriate concentration or range of concentrations of the organic polymer in the composition.

The glass transition temperatures of the organic polymer and the pretreatment base compound in part contribute to the flexibility, strength, hardness and similar qualities of the coating on the treated material surfaces. The glass transition temperature of these embodiments may range in degrees Celsius from about −125° C. to about 90° C. This glass transition temperature or $T_g$ determines the solid-solid transition of the polymer from a hard glassy material to a soft rubbery material. If the $T_g$ of the polymer is too high, the coating on the treated material will be stiff and inflexible. This is an undesirable result. The coating should be soft, flexible and unnoticeable to touch and sight yet should not flake, break-up or otherwise release from the keratin fiber, and especially from human hair, when stroked by a hand or brushed with a brush. The Tg of a polymer can be measured using ASTM D7426-08 (2008).

Examples of the organic polymer and base compound of the bicomponent composition according to the present invention include Cationic Acrylate Polymers useful as organic polymers include, for example; ttopol KX-10; Ottopol KX-99; Ottopol KX-101 from Gellner Industrial; RayCat® 65124 Specialty Polymers; FIOWLEN DOPA-15B; FIOWLEN DOPA-15 BHFS; FIOWLEN DOPA-17 HF; FIOWLEN DOPA-22; FIOWLEN DOPA-35 from Kyoeisha Chemical; MyCroFence AM 215 from Croda; WorléeCryl® 8721 from Worlée. Acrylate polymers useful as organic polymers and precursor organic polymers to which can be added at least two first functional groups such as hydroxyl, amine, mercapto and/or carboxyl include:

- Acrylates/Beheneth-25 Methacrylate Copolymer
- Acrylates/Beheneth-25 Methacrylate/Steareth-30 Methacrylate Copolymer
- Acrylates/C5-8 Alkyl Acrylate Copolymer
- Acrylates/C10-30 Alkyl Methacrylate Copolymer
- Acrylates/C12-22 Alkyl Methacrylate Copolymer
- Acrylates/Ceteth-20 Methacrylate Copolymer
- Acrylates/C26-28 Olefin Copolymer
- Acrylates/Ethylhexyl Acrylate Copolymer
- Acrylates/Hydroxyethyl Acrylate/Lauryl Acrylate Copolymer
- Acrylates/Hydroxyethyl Acrylate/Methoxyethyl Acrylate Copolymer
- Acrylates/Laureth-25 Methacrylate Copolymer
- Acrylates/Lauryl Methacrylate Copolymer
- Acrylates/Methoxy PEG-4 Methacrylate Copolymer
- Acrylates/Methoxy PEG-15 Methacrylate Copolymer
- Acrylates/Methoxy PEG-23 Methacrylate Copolymer
- Acrylates/Palmeth-25 Acrylate Copolymer
- Acrylates/Steareth-30 Methacrylate Copolymer
- Acrylates/Stearyl Methacrylate Copolymer
- Acrylic Acid/C12-22 Alkyl Acrylate Copolymer
- Acrylic Acid/Stearyl Acrylate Copolymer
- Ammonium Acrylates/Ethylhexyl Acrylate Copolymer
- Ammonium Acrylates/Methyl Styrene/Styrene Copolymer
- Ammonium Styrene/Acrylates/EthylhexylAcrylate/Lauryl Acrylate Copolymer
- Behenyl Methacrylate/t-Butyl Methacrylate Copolymer
- Butyl Acrylate/Cyclohexyl Methacrylate Copolymer a copolymer of butyl
- acrylate and cyclohexyl methacrylate film formers NR
- Butyl Acrylate/Ethylhexyl Methacrylate Copolymer a copolymer of butyl
- acrylate and 2-ethylhexyl methacrylate monomers film formers;
- Butyl Acrylate/Hydroxyethyl Methacrylate Copolymer
- Butyl Methacrylate/Acryoyloxy PG Methacrylate Copolymer
- C12-22 Alkyl Acrylate/Hydroxyethylacrylate Copolymer
- Cyclohexyl Methacrylate/Ethylhexyl Methacrylate Copolymer
- Ethylhexyl Acrylate/Methoxy PEG-23 Methacrylate/Vinyl Acetate Copolymer
- Ethylhexyl Acrylate/Methyl Methacrylate Copolymer
- Glyceryl Acrylate/Acrylic Acid Copolymer
- Hydroxyethyl Acrylate/Methoxyethyl Acrylate Copolymer
- Methoxy PEG-23 Methacrylate/Glyceryl Diisostearate Methacrylate Copolymer
- Poly C10-30 Alkyl Acrylate
- Potassium Acrylates Copolymer
- Potassium Acrylates/Ethylhexyl Acrylate Copolymer
- Sodium Acrylates/Ethylhexyl Acrylate Copolymer
- Sodium Acrylate/Vinyl Alcohol Copolymer
- Acrylates/Ceteareth-20 Methacrylate Crosspolymer
- Acrylates/Ceteareth-20 Methacrylate Crosspolymer-2
- Acrylates Crosspolymer-3
- Acrylates Crosspolymer-4
- Acrylates Crosspolymer-5
- Acrylates/Lauryl Methacrylate/Tridecyl Methacrylate Crosspolymer
- Acrylates/Methoxy PEG-90 Methacrylate Crosspolymer
- Acrylates/VA Crosspolymer
- Lauryl Acrylate Crosspolymer
- Lauryl Acrylate/VA Crosspolymer
- Methyl Methacrylate/PEG/PPG-4/3 Methacrylate Crosspolymer
- Polyacrylate-1 Crosspolymer
- Potassium Acrylate Crosspolymer
- Sodium Acrylates/Beheneth-25 Methacrylate Crosspolymer
- Poly(Methoxy PEG-9 Methacrylate)
- Polybutyl Acrylate
- Polybutyl Methacrylate
- Polyethylacrylate
- Polyhydroxyethylmethacrylate
- Polyisobutyl Methacrylate
- Polymethyl Acrylate
- Polypropyl Methacrylate
- Polystearyl Methacrylate
- Sodium Polymethacrylate
- Acrylates/C10-30Alkyl Acrylate Crosspolymer
- Acrylates/C12-13 Alkyl Methacrylates/Methoxyethyl Acrylate Crosspolymer
- Acrylates Crosspolymer
- Acrylates/Ethylhexyl Acrylate Crosspolymer
- Acrylates/Ethylhexyl Acrylate/Glycidyl Methacrylate Crosspolymer
- Acrylates/PEG-4 Dimethacrylate Crosspolymer
- Acrylates/Steareth-20 Methacrylate Crosspolymer
- Acrylates/Vinyl Isodecanoate Crosspolymer
- Acrylates/Vinyl Neodecanoate Crosspolymer
- Allyl Methacrylate/GlycolDimethacrylate Crosspolymer
- Allyl Methacrylates Crosspolymer
- Butyl Acrylate/Glycol Dimethacrylate Crosspolymer
- C8-22 Alkyl Acrylates/Methacrylic Acid Crosspolymer
- Glycol Dimethacrylate/Vinyl Alcohol Crosspolymer
- Lauryl Methacrylate/Glycol Dimethacrylate Crosspolymer
- Lauryl Methacrylate/Sodium Methacrylate Crosspolymer
- Methacrylic Acid/PEG-6 Methacrylate/PEG-6 Dimethacrylate Crosspolymer
- PEG/PPG-5/2 Methacrylate/Methacrylic Acid Crosspolymer
- Potassium Acrylates/C10-30 Alkyl Acrylate Crosspolymer Sodium Acrylates Crosspolymer-2

Sodium Acrylates/C10-30 Alkyl Acrylate Crosspolymer

Sodium Acrylates/Vinyl Isodecanoate Crosspolymer

Stearyl/Lauryl Methacrylate Crosspolymer

B. Plasticizer

If the glass transition temperature of the bicomponent composition and/or the substantive ingredients of the first and second components rare too high for the desired use yet the other properties of the polymer are appropriate, such as but not limited to color and wash fastness, one or more plasticizers can be combined with the bicomponent composition embodiments so as to lower the $T_g$ of the organic polymer and provide the appropriate feel and visual properties to the coating. The plasticizer can be incorporated directly in the coloring composition or can be applied to the hair before or after the coloring composition. The plasticizer can be chosen from the plasticizers usually used in the field of application.

The plasticizer or plasticizers can have a molecular mass of less than or equal to 5,000 g/mol, such as less than or equal to 2,000 g/mol, for example less than or equal to 1,000 g/mol, such as less than or equal to 900 g/mol. In at least one embodiment, the plasticizer, for example, has a molecular mass of greater than or equal to 40 g/mol.

Thus, the bicomponent composition can also comprise at least one plasticizer. For example, non-limiting mention can be made, alone or as a mixture, of common plasticizers such as: glycols and derivatives thereof, silicones, silicone polyethers, polyesterpolyols; adipic acid esters (such as diisodecyladipate), trimellitic acid esters, sebacic acid esters, azalaeic acid esters; nonlimiting examples of glycol derivatives are diethylene glycol ethyl ether, diethylene glycol methyl ether, diethylene glycol butyl ether or diethylene glycol hexyl ether, ethylene glycol ethyl ether, ethylene glycol butyl ether, or ethylene glycol hexyl ether; polyethylene glycols, polypropylene glycols, polyethylene glycol-polypropylene glycol copolymers, and mixtures thereof, such as high molecular weight polypropylene glycols, for example having a molecular mass ranging from 500 to 15,000, for instance glycol esters; propylene glycol derivatives such as propylene glycol phenyl ether, propylene glycol diacetate, dipropylene glycol ethyl ether, tripropylene glycol methyl ether, diethylene glycol methyl ether, and dipropylene glycol butyl ether. Such compounds are sold by Dow Chemical under the names DOWANOL PPH and DOWANOL DPnB; acid esters, for example esters of carboxylic acids, such as triacids, citrates, phthalates, adipates, carbonates, tartrates, phosphates, and sebacates; esters derived from the reaction of a monocarboxylic acid of formula $R_{11}COOH$ with a diol of formula $HOR_{12}OH$ in which $R_{11}$ and $R_{12}$, which can be identical or different, are chosen from a linear, branched or cyclic, saturated, or unsaturated hydrocarbon-based chain containing, for example, from 3 to 15 carbon atoms for example the monoesters resulting from the reaction of isobutyric acid and octanediol such as 2,2,4-trimethyl-1,3-pentanediol, such as the product sold under the reference TEXANOL ESTER ALCOHOL by the company Eastman Chemical; oxyethylenated derivatives, such as oxyethylenated oils, such as plant oils, such as castor oil; mixtures thereof.

Among the esters of tricarboxylic acids mention can be made of the esters of triacids wherein the triacid corresponds to formula

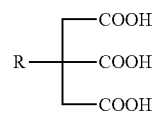

wherein R is a group —H, —OH or —OCOR' wherein R' is an alkyl group containing from 1 to 6 carbon atoms. For example, R can be a group —OCOCH$_3$. The esterifying alcohol for such tricarboxylic acids may be those described above for the monocarboxylic acid esters.

The plasticizer can be present in the composition of the present disclosure in an amount from about 0.01% to 20%.

C. Medium

The medium of the bicomponent composition embodiments of the invention may be water alone, water in mixture with a volatile polar protic or aprotic organic solvent, or a non-aqueous solvent or a mixture of non-aqueous solvents with polar protic or aprotic polar organic solvent. In general, the medium is any solvent suitable for dispersing the organic polymer, the pretreatment base compound and the base compound of the embodiments of the bicomponent composition described herein. In addition to water present in the medium, a volatile solvent may be present including a volatile polar protic or aprotic organic solvent, or mixtures thereof. Volatile organic solvents of which non-limiting mention may be made include: volatile pyrolidones 1-methylpyrrolidin-2-one, volatile $C_1$-$C_4$ alkanols such as methanol, ethanol or isopropanol; esters of liquid $C_2C_6$ acids and of volatile $C_1$-$C_8$ alcohols such as methyl acetate, n-butyl acetate, ethyl acetate, propyl acetate, isopentyl acetate, or ethyl 3-ethoxypropionate; ketones that are liquid at room temperature and volatile, such as methyl ethyl ketone, methyl isobutyl ketone, diisobutyl ketone, isophorone, cyclohexanone, or acetone; volatile polyols such as ethylene glycol and propylene glycol.

According to at least one embodiment of the present disclosure, the organic solvent is chosen from ethanol, isopropanol, acetone, and isododecane.

The medium with or without one or more volatile organic solvent may be present in the composition according to the present disclosure in an amount ranging from about 0.1% to about 95% by weight, such as from about 1% to about 70% by weight, for example ranging from 5% to 90% by weight relative to the total weight of the composition.

According to an embodiment, the medium is an aqueous medium.

D. Pigments

The color composition embodiments of the present invention make it possible to obtain colored and remnant coatings, without substantially altering the keratin fibers. As used herein, the term "pigment" generally refers to any particle colorant having or containing pigment material that gives hair fibers color including black and white, such as titanium dioxide that give only white to hair fibers. The pigments are substantially water-insoluble. The pigments, to distinguish from dyes presented in molecular from, are also referred to as pigment microparticles or pigment particles. The terms pigment microparticles and pigment particles are synonymous and are used herein interchangeably. The pigments can be organic, inorganic, or a combination of both. The pigments may be in pure form or coated, for example with a polymer or a dispersant.

Selections, multiple kinds and varying forms of the pigment microparticles as described in the following passages can be incorporated in any of the first and second components of the bicomponent composition, or can be incorporated in any two of these components or in all three. Preferably, pigment microparticles can be incorporated in either or both of the first and second components. More preferably, pigment particles can be incorporated in the first component.

The at least one pigment that can be used can be chosen from the organic and/or mineral pigments known in the art, such as those described in Kirk-Othmer's Encyclopedia of Chemical Technology and in Ullmann's Encyclopedia of Industrial Chemistry. The pigments comprised in the microparticles comprising at least one pigment will not substantially diffuse or dissolve into keratin fibers. Instead, the pigment comprised in the microparticles comprising at least one pigment will substantially remain separate from but attached to the keratin fibers.

The at least one pigment can be in the form of powder or of pigmentary paste. It can be coated or uncoated. The at least one pigment can be chosen, for example, from mineral pigments, organic pigments, elemental metal and their oxides, and other metal modifications, lakes, pigments with special effects such as nacres or glitter flakes, and mixtures thereof.

Pigment Shape

The pigment microparticles can have any suitable shape, including substantially spherical. But the pigment microparticles can also be oval, elliptical, tubular, irregular, etc., or even combinations of various shapes. In addition, the pigment microparticles can have two dimensions, length and width/diameter, of similar magnitude. In addition, the pigment microparticles can be micro platelets, i.e. having a thickness that is substantially smaller than the planar dimension. For example, five, ten or even 20 times smaller in thickness than in the planer dimension. In one embodiment with any of the reactive components of the instant invention, the pigments may be surface treated, surface coated or encapsulated.

In a particular aspect, the pigment microparticles can have a shape approximating that of a sphere, in which case the microparticles are referred to as being microspheres. Pigment microparticles which can be described as microspheres are understood as particles having an aspect ratio, defined as a function of the largest diameter, or largest dimension, dmax and the smallest diameter, or smallest dimension, dmin, which can be orthogonal to each other: AR=dmax/dmin which is from about 1:1 to 10:1, preferably from 1:1 to 5:1, more preferably from 1:1 to 4:1, such as from 1:1 to 3:1. More particularly, the expression "spherical-type" means that the pigment microparticles have a shape approximating that of a sphere. In other words, the pigment microparticles can be nearly orbicular in shape and can have a cross-sectional geometry that is essentially circular. Although not excluded, this does not necessarily mean that the pigment microparticles have the shape of a perfect sphere or ball. More likely, the shape of the pigment microparticles can exhibit a certain deviation from a sphere as long as the skilled person considers the shape as being similar to a sphere or as an approximation of a sphere.

In addition, the pigment microparticles can have a rather two-dimensional shape, with the smallest dimension substantially smaller than the two other dimensions, in which case the microparticles are referred to as being 2-dimensional microparticles. For example, the thickness of the microparticles can be significantly less than their length and width. The length and width can be of similar magnitude. Examples includes pigment microparticles having a shape of platelets, i.e. with a thickness that is substantially smaller than the planar dimension. For example, the aspect ratio AR=dmax/dmin, as defined above, of microparticles having a substantially two-dimensional shape, can be from about 10:1 to about 1000:1, preferably from about 10:1 to about 800:1, preferably from about 20:1 to about 800:1, preferably from about 10:1 to about 600:1, preferably from about 20:1 to about 600:1. Typically, the 2D-microparticles have a largest and a smallest dimension in their planer dimension, which both are significantly larger than the smallest dimension of the 2D-microparticles extending perpendicular to the planer dimension.

According to an embodiment, the pigments can include pigment microparticles of different shape. For example, microparticles of different size can be used to provide different reflecting and absorbing properties. Microparticles having different shape can also be formed of different pigment material. Furthermore, microparticles having different shape can also formed of different pigment material to provide different color.

Pigment Size

The pigments can be present in the composition in undissolved form. Depending on the shape, the pigments can have a D50[vol] particle diameter of from 0.001 micron to 1 micron.

For example, pigments that can be described as being microspheres can have a D50[vol] particle diameter of from 0.01 micron to 1 micron, preferably of from 0.015 micron to 0.75 micron, more preferably of from 0.02 micron to 0.50 micron. The microspheres can also have a D50[vol] particle diameter of from 0.6 micron to 0.9 micron, preferably of from 0.08 micron to 0.9 micron, and more preferably between of from 0.08 micron to 0.9 micron, such as from 0.08 micron to 0.8 micron, or such as of from 0.8 micron to 0.6 micron. According to an embodiment, the microspheres can also have a D50[vol] particle diameter of from 0.1 micron to 1 micron, preferably of from 0.12 micron to 1 micron, and more preferably between of from 0.16 micron to 1 micron, such as of from 0.2 micron to 1 micron, or such as of from 0.08 micron to 0.4 micron. The terms "micron" and "microns" describe the size in micrometers [μm].

In further embodiments, which can be combined with other embodiments described herein, the pigments, which can be described as microspheres, can have a D90[vol] particle diameter of from 0.1 micron to 1 micron, preferably of from 0.2 micron to 1 micron, and more preferably between of from 0.3 micron to 1 micron, such as of from 0.3 micron to 0.9 micron, or such as of from 0.4 micron to 0.8 micron, or such as of from 0.5 micron to 0.9 micron.

In some embodiments described herein, the pigments, which can be described as microspheres, can have a D10[vol] particle diameter of from 0.02 micron to 0.3 micron, preferably of from 0.06 micron to 0.3 micron, more preferably of from 0.08 micron to 0.3 micron, such as of from 0.08 micron to 0.2 micron, or such as of from 0.1 micron to 0.2 micron, or such as 0.12 micron to 0.3 micron.

In embodiments described herein, the D10[vol] particle diameter can be of from 0.02 micron to 0.3 micron and the D90[vol] can be of from 0.3 micron to 1 micron. In further embodiments, the D10[vol] particle diameter can be of from 0.06 micron to 0.2 micron and the D90[vol] can be of from 0.4 micron to 1 micron.

The particle diameter is represented by D10, D50 and/or by D90, which is the median diameter by volume. D10, D50 and D90 is measured with a Malvern Mastersizer 2000, which is a laser diffraction particle sizer and it is measured according to ISO 13320:2009(en) with Hydro 2000G or Hydro 2000S where the dispersant is water or ethanol. Detection range is from 0.01 micron to 2000 micron. D50 is expressed as x50 in ISO 13320:2009(en).

The term "D10," as used herein refers, to the 10th percentile number- or volume-based median particle diameter, which is the diameter below which 10% by number or volume of the particle population is found. The term "D50," as used herein refers, to the 50th percentile number- or volume-based median particle diameter, which is the diameter below which 50% by number or volume of the particle population is found. The term "D90," as used herein refers, to the 90th percentile number- or volume-based median particle diameter, which is the diameter below which 90% by number or volume of the particle population is found. The number or volume measurement is indicated by [num] for number or [vol] for volume. If not indicated otherwise, the particle size is given as D10[vol], D50[vol], and D90[vol], respectively.

Laser diffraction measures particle size distributions by measuring the angular variation in intensity of light scattered as a laser beam passes through a dispersed particulate sample analyzer and the particle size is reported as a volume equivalent sphere diameter. A discussion of calculating D50 is provided in Barber et al, Pharmaceutical Development and Technology, 3(2), 153-161 (1998), which is incorporated herein by reference. Pigment microparticles having a D50[vol] particle diameter of less than 20 nm may enter the cuticles and are therefore difficult to remove. For scattering purposes, Pigment(s) having a D10[vol] particle diameter of at least 60 nm, or at least 80 nm can be used. Pigment(s) having a D50[vol] particle diameter of more than 1 micron typically do not sufficiently adhere onto hair fibers.

According to an embodiment, the particle size distribution, either relative to the number or volume of the particles, of the pigment microparticles can be at least bi-modal. A bi-modal particle size distribution has two distinct peaks which are spaced relative from, while tri-modal particle size distribution has three distinct peaks. The term "peak" means a local maximum of the distribution curve. The "distance" between two peaks, expressed relative to the particle size, can be at least 0.05 micron, preferably at least 0.1 micron, such as at least 0.2 micron. Providing an at least bi-modal particle size distribution allows to tailor the optical appearance of the colored hair. For example, the scattering properties varies with the particle size so that particles of different size scatter the light into different directions.

The at least bi-modal particle size distribution can be relative to pigment microparticles formed by the same pigment material. In addition to that or alternatively, the at least bi-model particle size distribution can be provided by pigment microparticles of different pigment material.

The size of pigment microparticles which can be described to have a 2-dimensional shape, and which are referred to as 2-dimensional microparticles can be determined by SEM. The size of 2-dimensional microparticles can also be determined by laser diffraction measurements. The particle size determined by laser diffraction is a mean size of the different dimensions of the 2-dimensional particles. The apparent D50[vol] particle diameter of 2-dimensional microparticles, as measured by SEM, can be from 0.5 micron to 50 microns, more preferably from 0.8 micron to 20 microns, more preferably from 1 micron to 15 microns, more preferably from 1.5 micron to 10 microns.

According to an embodiment, pigment particles are referred to as being microspheres can be used light-scattering and/or light absorbing purposes. Those particles, due to their pigment material, impart the hair with a specific color.

According to an embodiment, pigment particles are referred to as being 2-dimensional microparticles can be mainly used for light-reflecting and/or light absorbing purposes. Those particles, due to their pigment material, mainly reflect the light without significantly alter the color of the light.

The pigment microparticles can be light absorbing, but which for wavelengths of visible light provide negligible to low or no scattering. While not wishing to bound by any specific theory, it is believed that such pigments can provide more chromatic colors. Such pigment microparticles can have a D50[vol] value between about 0.001 micron and about 0.15 micron, between about 0.005 micron and about 0.1 micron or between about 0.010 micron and about 0.075 micron.

The pigment microparticles can be predominantly light scattering for wavelengths of visible light and provide low light absorption. While not wishing to bound by any specific theory, it is believed that such pigments can provide the visual effect of lightening the hair. Such pigment microparticles, which can be microspheres, can have a D50[vol] value between about 0.05 micron to about about 1 micron, between 0.08 micron to about 0.9 micron, between about 0.05 micron and about 0.75 micron, between about 0.1 micron and about 0.5 micron or about 0.15 micron and about 0.4 micron. Such materials can have a refractive index above 1.5, above 1.7 or above 2.0.

Pigments made from metal and metal like materials which can conduct electricity, and which can absorb light and re-emit the light out of the metal to give the appearance of strong reflectance. While not wishing to be bound by any specific theory, it is believed that the absorbed light will induce alternating electric currents on the metal surface, and that this currents immediately re-emit light out of the metal. Such pigment microparticles can be platelets, e.g., having a thickness that is substantially smaller than the planar dimension. For example about five, about 10 or even about 400 times smaller in thickness than in the planer. Such platelets can have a planar dimension less than about 30 nm, but with a thickness less than about 10 micron wide. This includes a ratio of 10000 to 30, or 333. Platelets larger in size, such as 50 microns are even available in this thickness of 10 microns, and so the ratios can even go up to 2000.

The pigment microparticles can be a composite formed by two different types of pigment microparticles. Examples include a composite of a 2-dimensional microparticle and at least one micro spherical particle (microsphere), a composite of different micro spherical particles, and a composite of different 2-dimensional particles. Composite particles formed by 2-dimensional microparticles to which micro spherical particles adhere provide an attractive alternative to a pure mixture of 2-dimensional microparticles and micro spherical particles. For example, a metallic 2-dimensional microparticle can carry one or more micro spherical particle such as one or more organic micro spherical particle. The micro spherical particles attached or bonded to the 2-dimensional microparticle can be formed of the same pigment material or can be formed of different pigment material. Composite microparticles formed of 2-dimensional microparticles and micro spherical particles can provide multiple functionality in one particle such as (metallic) reflectance and dielectric scattering, reflectance and absorption.

Pigment microparticles may be materials which are composite comprising a core of pigments made from metal and metal like materials which can conduct electricity, and which can absorb light and re-emit the light out of the metal to give the appearance of strong reflectance. While not wishing to be bound by any specific theory, it is believed that the absorbed light will induce alternating electric currents on the metal surface, and that this currents immediately re-emit light out of the metal. Upon this pigment light absorbing microparticles is immobilized. Such pigment microparticles can be platelets, e.g., having a thickness that is substantially smaller than the planar dimension. For example, five, ten or even 20 times smaller in thickness than in the planer. Such platelets can have a planer dimension less than 15 microns, but with a thickness less than 1 microns, more preferably with a planer dimension less than 12 microns but with a thickness less than 750 nm, even more preferably with a plan dimension less than 10 microns and a thickness less than 0.5 micron. The light absorbing microparticles can have D50 [vol] value between 0.001 micron and 0.15 micron, more preferably between 0.002 micron and 0.1 micron and even more preferable between 0.005 micron and 0.075 micron.

The light absorbing microparticles may also include dyes, pigments, or materials with color centers in the crystal structure, or photonic structures resulting in destructive or constructive interference, diffraction or other structures and materials mentioned in the book "The Physics and Chemistry of Color: the Fifteen Causes of Color", $2^{nd}$ Edition by K.I. Nassau (ISBN 978-0-471-39106-7).

The pigment microparticles can be both light scattering and absorbing for wavelengths of visible light. While not wishing to bound by any specific theory, it is believed that such pigments can provide both some visual effect of lightening the hair. Such pigment microparticles can have a D50[num] value between about 50 nm and about 750 nm, between about 100 nm and about 500 nm or between about 150 nm and about 400 nm. Such materials have a refractive index above about 1.5, above about 1.7 or above about 2.0.

According to an embodiment, different pigment microparticles are combined to provide reflective, transmitting and refractive properties of the hair colored with the color composition described herein. A microparticle combination can be a material composite using at least two different pigment materials to form the pigment microparticles. In addition to, or alternating to, the microparticle combination, a mixture of separate pigment microparticles of different type can be used to bring about the desired reflective, transmitting and refractive properties.

The composite pigments, combination of pigments, and mixtures of pigment microparticles eliminate, or at least significantly reduce, hair penetration and scattering by light and thus eliminate the perception of pigment of natural hair color change.

Pigment Concentration

The color composition for coloring hair fibers according to the present disclosure comprises microparticles comprising at least one pigment. The color composition comprises from about 0.01% to about 40%, about 0.05% to about 35%, about 0.1 to about 25%, or about 0.15% and about 20% pigment(s), by weight of the color composition.

Pigment Material

The material of the pigment microparticles can be inorganic or organic. Inorganic-organic mixed pigments are also possible.

According to an embodiment, inorganic pigment(s) are used. The advantage of inorganic pigment(s) is their excellent resistance to light, weather, and temperature. The inorganic pigment(s) can be of natural origin, and are, for example, derived from material selected from the group consisting of chalk, ochre, umber, green earth, burnt sienna, and graphite. The pigment(s) can preferably be white pigments, such as, for example, titanium dioxide or zinc oxide. The pigment(s) can also be colored pigments, such as, for example, ultramarine or iron oxide red, luster pigments, metal effect pigments, pearlescent pigments, and fluorescent or phosphorescent pigments. The pigment(s) can be selected from the group consisting of metal oxides, hydroxides and oxide hydrates, mixed phase pigments, sulfur-containing silicates, metal sulfides, complex metal cyanides, metal sulfates, chromates and molybdates, alloys, and the metals themselves. The pigment(s) can be selected from the group consisting of titanium dioxide (CI 77891), black iron oxide (CI 77499), yellow iron oxide (CI 77492), red and brown iron oxide (CI 77491), manganese violet (CI 77742), ultramarine (sodium aluminum sulfosilicates, CI 77007, Pigment Blue 29), chromium oxide hydrate (CI 77289), Prussian blue (ferric ferrocyanide, CI 77510), carmine (cochineal), zinc sulfide, barium sulfate, zinc oxide, siliconised titanium dioxide, siliconised zinc sulfide, siliconised zinc oxide, and mixtures thereof. The pigment(s) can be selected from the group consisting of iron oxide, titanium dioxide, mica, borosilicate, and combinations thereof. The pigment(s) can comprise an iron oxide ($Fe_2O_3$) pigment. The pigment(s) can comprise a combination of mica and titanium dioxide.

The pigment(s) can be pearlescent and colored pigment(s), and can preferably be based on mica which are coated with a metal oxide or a metal oxychloride, such as titanium dioxide or bismuth oxychloride, and optionally further color-imparting substances, such as iron oxides, Prussian blue, ultramarine, and carmine. The color exhibited by a pigment can be adjusted by varying the layer thickness. Such pigments are sold, for example, under the trade names Rona®, Colorona®, Dichrona®, RonaFlair®, Ronastar®, Xirona® and Timiron® all of which are available from Merck, Darmstadt, Germany. For example, Xirona® is a brand for color travel pigments that display color shifting effects depending on the viewing angle and are based on either natural mica, $SiO_2$ or calcium aluminum borosilicate flakes, coated with varying layers of $TiO_2$. Pigment(s) from the line KTZ® from Kobo Products, Inc., 3474 So. Clinton Ave., So. Plainfield, USA, are also useful herein, in particular the Surface Treated KTZ® Pearlescent Pigments from Kobo. Particularly useful are KTZ® FINE WHITE (mica and TiO2) having a D50 particle diameter of 5 to 25 micron and also KTZ® CELESTIAL LUSTER (mica and TiO2, 10 to 60 micron) as well as KTZ® CLASSIC WHITE (mica and TiO2, 10 to 60 micron). Also useful are SynCrystal Sapphire from Eckart Effect Pigments, which is a blue powder comprising platelets of synthetic fluorphlogopite coated with titanium dioxide, ferric ferrocyanide and small amounts of tin oxide. Also useful is SYNCRYSTAL Almond also from Eckart, which is a beige powder with a copper reflection color and is composed of platelets of synthetic fluorphlogopite and coated with titanium dioxide and iron oxides. Also useful is Duocrome® RV 524C from BASF, which provides a two color look via a lustrous red powder with a violet reflection powder due to its composition of mica, titanium dioxide and carmine. The colored pigment(s) can be lightly bright colored pigment(s), and can particularly be white color variations.

The pigment(s) can be organic pigments. The at least one pigment can be an organic pigment. As used herein, the term "organic pigment" means any pigment that satisfies the definition in Ullmann's encyclopedia in the chapter on organic pigments. For instance, the at least one organic pigment can be chosen from nitroso, nitro, azo, xanthene, quinoline, anthraquinone, phthalocyanin, copper phthalocyanin, copper hexadecachlorophthalocyanine, 2-[(2-Methoxy-4-nitrophenyl)azo]-N-(2-methoxyphenyl)-3-oxobutyramide, metal-complex, isoindolinone, isoindoline, quinacridone, perinone, perylene, diketopyrrolopyrrole, thioindigo, dioxazine, triphenylmethane, dimethylquinacridone and quinophthalone compounds, Azo-dyes, Nonionic azo dyes, Anionic Azo dyes, Cationic azo dyes, Complex forming azo dye, aza annulene dyes, aza analogue of diarylmethane dyes, aza annulene dyes, Nitro-dyes and their pigments, Carbonyl dyes and their pigments (for example, Anthrachinon dyes, indigo), Sulfur dyes, Florescence dyes, Anthracene or Insoluble alkali or earth metal acid dyes.

Or the pigment can be at least one of uncolored and UV absorbing.

The organic pigment(s) can be selected from the group consisting of natural pigments sepia, gamboge, bone charcoal, Cassel brown, indigo, chlorophyll and other plant pigments. The synthetic organic pigments can be selected from the group consisting of azo pigments, anthraquinoids, indigoids, dioxazine, quinacridone, phthalocyanine, isoindolinone, perylene and perinone, metal complex, alkali blue, diketopyrrolopyrrole pigments, and combinations thereof. A particularly preferred pigment is 7-Bis(1,3-dichloropropan-2-yl)benzo[lmn][3,8]phenanthrolin-1,3,6,8(2H,7H)-tetraon.

According to an embodiment, the pigment(s) can be selected from the pigment group consisting of, including any combination thereof (with CI meaning color index and CAS meaning Chemical Abstract Service Number)

Pigment Black 10 [C.I. 77265, (CAS: 7782-42-5)], Pigment Black 11 [C.I. 77499, (CAS: 12227-89-3)], Pigment Black 12 [C.I. 77543, (CAS: 68187-02-0)], Pigment Black 13 [C.I. 77322, (CAS: 1307-96-6)], Pigment Black 14 [C.I. 77728, (CAS: 83512-98-5)], Pigment Black 15 [C.I. 77403, (CAS: 1317-38-0)], Pigment Black 17 [C.I. 77975, (CAS: 1314-98-3)], Pigment Black 18 [C.I. 77011, (CAS: 12001-98-8)], Pigment Black 23 [C.I. 77865, (CAS: 68187-54-2)], Pigment Black 24 [C.I. 77898, (CAS: 68187-00-8)], Pigment Black 25 [C.I. 77332, (CAS: 68186-89-0)], Pigment Black 26 [C.I. 77494, (CAS: 68186-94-7)], Pigment Black 27 [C.I. 77502, (CAS: 68186-97-0)], Pigment Black 28 [C.I. 77428, (CAS: 68186-91-4)], Pigment Black 29 [C.I. 77498, (CAS: 68187-50-8)], Pigment Black 30 [C.I. 77504, (CAS: 71631-15-7)], Pigment Black 31 [C.I. 71132, (CAS: 67075-37-0)], Pigment Black 32 [C.I. 71133, (CAS: 83524-75-8)], Pigment Black 33 [C.I. 77537, (CAS: 188735-18-4)], Pigment Black 34 [C.I. 77770, (CAS: 1317-33-5)], Pigment Black 6 [C.I. 77266, (CAS: 1333-86-4)], Pigment Black 7 [C.I. 77266, (CAS: 1333-86-4)], Pigment Black 8 [C.I. 77268, (CAS: 1339-82-8)], Pigment Black 9 [C.I. 77267, (CAS: 8021-99-6)], Pigment Blue 10 [C.I. 44040, (CAS: 1325-93-5)], Pigment Blue 15 [C.I. 74160, (CAS: 147-14-8)], Pigment Blue 16 [C.I. 74100, (CAS: 574-93-6)], Pigment Blue 18 [C.I. 42770, (CAS: 1324-77-2)], Pigment Blue 21 [C.I. 69835, (CAS: 1324-26-1)], Pigment Blue 22 [C.I. 69810, (CAS: 1324-27-2)], Pigment Blue 25 [C.I. 21180, (CAS: 10127-03-4)], Pigment Blue 26 [C.I. 21185, (CAS: 5437-88-7)], Pigment Blue 28 [C.I. 77346, (CAS: 1345-16-0)], Pigment Blue 29 [C.I. 77007, (CAS: 57455-37-5)], Pigment Blue 30 [C.I. 77420, (CAS: 1339-83-9)], Pigment Blue 32 [C.I. 77365, (CAS: 69458-70-4)], Pigment Blue 33 [C.I. 77112, (CAS: 8046-59-1)], Pigment Blue 34 [C.I. 77450, (CAS: 1317-40-4)], Pigment Blue 35 [C.I. 77368, (CAS: 83712-59-8)], Pigment Blue 36 [C.I. 77343, (CAS: 68187-11-1)], Pigment Blue 56 [C.I. 42800, (CAS: 6417-46-5)], Pigment Blue 57 [C.I. 42795, (CAS: 5905-38-4)], Pigment Blue 60 [C.I. 69800, (CAS: 81-77-6)], Pigment Blue 61 [C.I. 42765, (CAS: 1324-76-1)], Pigment Blue 62 [C.I. 42595, (CAS: 82338-76-9)], Pigment Blue 63 [C.I. 73015, (CAS: 16521-38-3)], Pigment Blue 64 [C.I. 69825, (CAS: 130-20-1)], Pigment Blue 65 [C.I. 59800, (CAS: 116-71-2)], Pigment Blue 66 [C.I. 73000, (CAS: 482-89-3)], Pigment Blue 71 [C.I. 77998, (CAS: 68186-95-8)], Pigment Blue 72 [C.I. 77347, (CAS: 68186-87-8)], Pigment Blue 73 [C.I. 77364, (CAS: 68187-40-6)], Pigment Blue 74 [C.I. 77366, (CAS: 68412-74-8)], Pigment Blue 75 [C.I. 74160, (CAS: 3317-67-7)], Pigment Blue 76 [C.I. 742520, (CAS: 176365-61-0)], Pigment Blue 78 [C.I. 42090, (CAS: 68921-42-6)], Pigment Blue 79 [C.I. 741300, (CAS: 14154-42-8)], Pigment Blue 9 [C.I. 42025B, (CAS: 596-42-9)], Pigment Brown 1 [C.I. 12480, (CAS: 6410-40-8)], Pigment Brown 10 [C.I. 77227, (CAS: 12013-69-3)], Pigment Brown 11 [C.I. 77495, (CAS: 64294-89-9)], Pigment Brown 2 [C.I. 12071, (CAS: 10279-43-3)], Pigment Brown 22 [C.I. 10407, (CAS: 29398-96-7)], Pigment Brown 23 [C.I. 20060, (CAS: 35869-64-8)], Pigment Brown 24 [C.I. 77310, (CAS: 68186-90-3)], Pigment Brown 26 [C.I. 71129, (CAS: 81-33-4)], Pigment Brown 27 [C.I. 73410, (CAS: 3989-75-1)], Pigment Brown 28 [C.I. 69015, (CAS: 131-92-0)], Pigment Brown 33 [C.I. 77503, (CAS: 68186-88-9)], Pigment Brown 34 [C.I. 77497, (CAS: 68187-10-0)], Pigment Brown 35 [C.I. 77501, (CAS: 68187-09-7)], Pigment Brown 37 [C.I. 77890, (CAS: 70248-09-8)], Pigment Brown 38 [C.I. 561660, (CAS: 126338-72-5)], Pigment Brown 39 [C.I. 77312, (CAS: 71750-83-9)], Pigment Brown 6 [C.I. 77491, 77492 and 77499, (CAS: 52357-70-7)], Pigment Brown 9 [C.I. 77430, (CAS: 8014-85-5)], Pigment Green 10 [C.I. 12775, (CAS: 61725-51-7)], Pigment Green 12 [C.I. 10020, (CAS: 84682-41-7)], Pigment Green 15 [C.I. 77600, (CAS: 12224-92-9)], Pigment Green 17 [C.I. 77288, (CAS: 1308-38-9)], Pigment Green 18 [C.I. 77289, (CAS: 12001-99-9)], Pigment Green 19 [C.I. 77335, (CAS: 8011-87-8)], Pigment Green 20 [C.I. 77408, (CAS: 8007-61-2)], Pigment Green 21 [C.I. 77410, (CAS: 12002-03-8)], Pigment Green 22 [C.I. 77412, (CAS: 1345-20-6)], Pigment Green 23 [C.I. 77009, (CAS: 1344-98-5)], Pigment Green 24 [C.I. 77013, (CAS: 1345-00-2)], Pigment Green 26 [C.I. 77344, (CAS: 68187-49-5)], Pigment Green 27 [C.I. 77520, (CAS: 15418-51-6)], Pigment Green 36 [C.I. 74265, (CAS: 14302-13-7)], Pigment Green 37 [C.I. 74255, (CAS: 1330-37-6)], Pigment Green 38 [C.I. 74265, (CAS: 14302-13-7)], Pigment Green 42 [C.I. 74260, (CAS: 1328-53-6)], Pigment Green 47 [C.I. 59825, (CAS: 128-58-5)], Pigment Green 50 [C.I. 77377, (CAS: 68186-85-6)], Pigment Green 51 [C.I. 77300, (CAS: 68553-01-5)], Pigment Green 54 [C.I. 59830, (CAS: 25704-81-8)], Pigment Green 58 [C.I. 742655, (CAS: 1143572-73-9)], Pigment Green 8 [C.I. 10006, (CAS: 16143-80-9)], Pigment Green 9 [C.I. 49415, (CAS: 1326-13-2)], Pigment Orange 1 [C.I. 11725, (CAS: 6371-96-6)], Pigment Orange 13 [C.I. 21110, (CAS: 3520-72-7)], Pigment Orange 14 [C.I. 21165, (CAS: 6837-37-2)], Pigment Orange 15 [C.I. 21130, (CAS: 6358-88-9)], Pigment Orange 16 [C.I. 21160, (CAS: 6505-28-8)], Pigment Orange 17 [C.I. 15510, (CAS: 15782-04-4)], Pigment Orange 17 [C.I. 15510, (CAS: 15876-51-4)], Pigment Orange 18 [C.I. 15970, (CAS: 1325-14-0)], Pigment Orange 19 [C.I. 15990, (CAS: 5858-88-8)], Pigment Orange 20 [C.I. 77202, (CAS: 12656-57-4)], Pigment Orange 21 [C.I. 77601, (CAS: 1344-38-3)], Pigment Orange 22 [C.I. 12470, (CAS: 6358-48-1)], Pigment Orange 23 [C.I. 77201, (CAS: 1345-09-1)], Pigment Orange 24 [C.I. 12305, (CAS: 6410-27-1)], Pigment Orange 3 [C.I. 12105, (CAS: 6410-15-7)], Pigment Orange 31 [C.I. 20050, (CAS: 5280-74-0)], Pigment Orange 34 [C.I. 21115, (CAS: 15793-73-4)], Pigment Orange 39 [C.I. 45370, (CAS: 15876-57-0)], Pigment Orange 4 [C.I. 12459, (CAS: 21889-27-0)], Pigment Orange 40 [C.I. 59700, (CAS: 128-70-1)], Pigment Orange 43 [C.I. 71105, (CAS: 4424-06-0)], Pigment Orange 44 [C.I. 21162, (CAS: 17453-73-5)], Pigment Orange 45 [C.I. 77601, (CAS: 59519-55-0)], Pigment Orange 46 [C.I. 15602, (CAS: 63467-26-5)], Pigment Orange 5 [C.I. 12075, (CAS: 3468-63-1)], Pigment Orange 6 [C.I. 12730, (CAS: 6407-77-8)], Pigment Orange 61 [C.I. 11265, (CAS: 40716-47-0)], Pigment Orange 64 [C.I. 12760, (CAS: 72102-84-2)], Pigment Orange 65 [C.I. 48053, (CAS: 20437-10-9)], Pigment Orange 66 [C.I. 48210, (CAS: 68808-69-5)], Pigment Orange 67 [C.I. 12915, (CAS: 74336-59-7)], Pigment Orange 68 [C.I. 486150, (CAS: 42844-93-9)], Pigment Orange 69 [C.I. 56292, (CAS: 85959-60-0)], Pigment Orange 7 [C.I. 15530, (CAS: 5850-81-7)], Pigment Orange 71 [C.I. 561200, (CAS: 84632-50-8)], Pigment Orange 72 [C.I. 211095, (CAS: 384329-80-0)], Pigment Orange 73 [C.I. 561170, (CAS: 84632-59-7)], Pigment Orange 75 [C.I. 772830, (CAS: 12014-93-6)], Pigment Orange 77 [C.I. 59105, (CAS: 1324-11-4)], Pigment Red 10 [C.I. 12440, (CAS: 6410-35-1)], Pigment Red 100 [C.I. 13058, (CAS: 6371-55-7)], Pigment Red 101 [C.I. 77491, (CAS: 1309-37-1)], Pigment Red 101 [C.I. 77015, (CAS: 529484-30-8)], Pigment Red 103 [C.I. 77601, (CAS: 59519-56-1)], Pigment Red 104 [C.I. 77605, (CAS: 12656-85-8)], Pigment Red 105 [C.I. 77578, (CAS: 1314-41-6)], Pigment Red 106 [C.I. 77766, (CAS: 1344-48-5)], Pigment Red 107 [C.I. 77060, (CAS: 1345-04-6)], Pigment Red 108 [C.I. 77202, (CAS: 58339-34-7)], Pigment Red 109 [C.I. 77482, (CAS: 1345-24-0)], Pigment Red 11 [C.I. 12430, (CAS: 6535-48-4)], Pigment Red 112 [C.I. 12370, (CAS: 6535-46-2)], Pigment Red 113 [C.I. 77201, (CAS: 1345-09-1)], Pigment Red 114 [C.I. 12351, (CAS: 6358-47-0)], Pigment Red 115 [C.I. 15851, (CAS: 6358-40-3)], Pigment Red 117 [C.I. 15603, (CAS: 10142-77-5)], Pigment Red 119 [C.I. 12469, (CAS: 72066-77-4)], Pigment Red 12 [C.I. 12385, (CAS: 6410-32-8)], Pigment Red 121 [C.I. 77302, (CAS: 12125-42-7)], Pigment Red 122 [C.I. 73915, (CAS: 980-26-7)], Pigment Red 13 [C.I. 12395, (CAS: 6535-47-3)], Pigment Red 133 [C.I. 15920, (CAS: 5280-67-1)], Pigment Red 14 [C.I. 12380, (CAS: 6471-50-7)], Pigment Red 141 [C.I. 20044, (CAS: 3864-06-0)], Pigment Red 144 [C.I. 20735, (CAS: 5280-78-4)], Pigment Red 146 [C.I. 12485, (CAS: 5280-68-2)], Pigment Red 147 [C.I. 12433, (CAS: 68227-78-1)], Pigment Red 148 [C.I. 12369, (CAS: 94276-08-1)], Pigment Red 149 [C.I. 71137, (CAS: 4948-15-6)], Pigment Red 15 [C.I. 12465, (CAS: 6410-39-5)], Pigment Red 150 [C.I. 12290, (CAS: 56396-10-2)], Pigment Red 151 [C.I. 15892, (CAS: 61013-97-6)], Pigment Red 157 [C.I. 12355, (CAS: 6471-49-4)], Pigment Red 16 [C.I. 12500, (CAS: 6407-71-2)], Pigment Red 162 [C.I. 12431, (CAS: 6358-59-4)], Pigment Red 163 [C.I. 12455, (CAS: 6410-37-3)], Pigment Red 164 [C.I. 212855, (CAS: 72659-69-9)], Pigment Red 166 [C.I. 20730, (CAS: 3905-19-9)], Pigment Red 168 [C.I. 59300, (CAS: 4378-61-4)], Pigment Red 169 [C.I. 45160, (CAS: 12237-63-7)], Pigment Red 17 [C.I. 12390, (CAS: 6655-84-1)], Pigment Red 170 [C.I. 12475, (CAS: 2786-76-7)], Pigment Red 170 [C.I. 12474, (CAS: 36968-27-1)], Pigment Red 171 [C.I. 12512, (CAS: 6985-95-1)], Pigment Red 172 [C.I. 45430, (CAS: 12227-78-0)], Pigment Red 173 [C.I. 45170, (CAS: 12227-77-9)], Pigment Red 174 [C.I. 45410, (CAS: 15876-58-1)], Pigment Red 175 [C.I. 12513, (CAS: 6985-92-8)], Pigment Red 177 [C.I. 65300, (CAS: 4051-63-2)], Pigment Red 179 [C.I. 71130, (CAS: 5521-31-3)], Pigment Red 18 [C.I. 12350, (CAS: 3564-22-5)], Pigment Red 181 [C.I. 73360, (CAS: 2379-74-0)], Pigment Red 184 [C.I. 12487, (CAS: 99402-80-9)], Pigment Red 185 [C.I. 12516, (CAS: 51920-12-8)], Pigment Red 187 [C.I. 12486, (CAS: 59487-23-9)], Pigment Red 188 [C.I. 12467, (CAS: 61847-48-1)], Pigment Red 189 [C.I. 71135, (CAS: 2379-77-3)], Pigment Red 19 [C.I. 12400, (CAS: 6410-33-9)], Pigment Red 190 [C.I. 71140, (CAS: 6424-77-7)], Pigment Red 192 [C.I. 739155, (CAS: 61968-81-8)], Pigment Red 193 [C.I. 16185, (CAS: 12227-62-2)], Pigment Red 195 [C.I. 70320, (CAS: 4203-77-4)], Pigment Red 196 [C.I. 67000, (CAS: 2379-79-5)], Pigment Red 198 [C.I. 73390, (CAS: 6371-31-9)], Pigment Red 2 [C.I. 12310, (CAS: 6041-94-7)], Pigment Red 200 [C.I. 15867, (CAS: 58067-05-3)], Pigment Red 200 [C.I. 15867, (CAS: 32041-58-0)], Pigment Red 202 [C.I. 73907, (CAS: 3089-17-6)], Pigment Red 208 [C.I. 12514, (CAS: 31778-10-6)], Pigment Red 21 [C.I. 12300, (CAS: 6410-26-0)], Pigment Red 210 [C.I. 12477, (CAS: 61932-63-6)], Pigment Red 211 [C.I. 15910, (CAS: 85702-54-1)], Pigment Red 212 [C.I. 12360, (CAS: 6448-96-0)], Pigment Red 214 [C.I. 200660, (CAS: 40618-31-3)], Pigment Red 216 [C.I. 59710, (CAS: 1324-33-0)], Pigment Red 22 [C.I. 12315, (CAS: 6448-95-9)], Pigment Red 220 [C.I. 20055, (CAS: 68259-05-2)], Pigment Red 221 [C.I. 20065, (CAS: 71566-54-6)], Pigment Red 222 [C.I. 123665, (CAS: 20981-12-8)], Pigment Red 224 [C.I. 71127, (CAS: 128-69-8)], Pigment Red 226 [C.I. 597200, (CAS: 72828-01-4)], Pigment Red 229 [C.I. 77006, (CAS: 85536-78-3)], Pigment Red 230 [C.I. 77003, (CAS: 68187-27-9)], Pigment Red 231 [C.I. 77005, (CAS: 68186-99-2)], Pigment Red 232 [C.I. 77996, (CAS: 68412-79-3)], Pigment Red 233 [C.I. 77301, (CAS: 68187-12-2)], Pigment Red 235 [C.I. 77290, (CAS: 68201-65-0)], Pigment Red 236 [C.I. 77863, (CAS: 68187-53-1)], Pigment Red 242 [C.I. 20067, (CAS: 52238-92-3)], Pigment Red 243 [C.I. 15910, (CAS: 50326-33-5)], Pigment Red 243 [C.I. 15910, (CAS: 431991-58-1)], Pigment Red 247 [C.I. 15915, (CAS: 43035-18-3)], Pigment Red 248 [C.I. 200552, (CAS: 80648-58-4)], Pigment Red 251 [C.I. 12925, (CAS: 74336-60-0)], Pigment Red 253 [C.I. 12375, (CAS: 85776-13-2)], Pigment Red 254 [C.I. 56110, (CAS: 84632-65-5)], Pigment Red 255 [C.I. 561050, (CAS: 54660-00-3)], Pigment Red 256 [C.I. 124635, (CAS: 79102-65-1)], Pigment Red 257 [C.I. 562700, (CAS: 70833-37-3)], Pigment Red 258 [C.I. 12318, (CAS: 57301-22-1)], Pigment Red 259 [C.I. 77007, (CAS: 113956-14-2)], Pigment Red 260 [C.I. 56295, (CAS: 71552-60-8)], Pigment Red 261 [C.I. 12468, (CAS: 16195-23-6)], Pigment Red 264 [C.I. 561300, (CAS: 88949-33-1)], Pigment Red 265 [C.I. 772830, (CAS: 12014-93-6)], Pigment Red 267 [C.I. 12396, (CAS: 68016-06-8)], Pigment Red 268 [C.I. 12316, (CAS: 16403-84-2)], Pigment Red 269 [C.I. 12466, (CAS: 67990-05-0)], Pigment Red 271 [C.I. 487100, (CAS: 85958-80-1)], Pigment Red 273 [C.I. 16035, (CAS: 68583-95-9)], Pigment Red 274 [C.I. 16255, (CAS: 12227-64-4)], Pigment Red 3 [C.I. 12120, (CAS: 2425-85-6)], Pigment Red 30 [C.I. 12330, (CAS: 6471-48-3)], Pigment Red 32 [C.I. 12320, (CAS: 6410-29-3)], Pigment Red 37 [C.I. 21205, (CAS: 6883-91-6)], Pigment Red 38 [C.I. 21120, (CAS: 6358-87-8)], Pigment Red 39 [C.I. 21080, (CAS: 6492-54-2)], Pigment Red 4 [C.I. 12085, (CAS: 2814-77-9)], Pigment Red 40 [C.I. 12170, (CAS: 2653-64-7)], Pigment Red 41 [C.I. 21200, (CAS: 6505-29-9)], Pigment Red 42 [C.I. 21210, (CAS: 6358-90-3)], Pigment Red 48 [C.I. 15865, (CAS: 3564-21-4)], Pigment Red 48 [C.I.

15865, (CAS: 1325-12-8)], Pigment Red 48 [C.I. 15865, (CAS: 7585-41-3)], Pigment Red 48 [C.I. 15865, (CAS: 7023-61-2)], Pigment Red 48 [C.I. 15865, (CAS: 15782-05-5)], Pigment Red 48 [C.I. 15865, (CAS: 5280-66-0)], Pigment Red 48 [C.I. 15865, (CAS: 71832-83-2)], Pigment Red 48 [C.I. 15865, (CAS: 68966-97-2)], Pigment Red 49 [C.I. 15630, (CAS: 1248-18-6)], Pigment Red 49 [C.I. 15630, (CAS: 1325-06-0)], Pigment Red 49 [C.I. 15630, (CAS: 1103-38-4)], Pigment Red 49 [C.I. 15630, (CAS: 1103-39-5)], Pigment Red 49 [C.I. 15630, (CAS: 6371-67-1)], Pigment Red 5 [C.I. 12490, (CAS: 6410-41-9)], Pigment Red 50 [C.I. 15500, (CAS: 5850-76-0)], Pigment Red 50 [C.I. 15500, (CAS: 6372-81-2)], Pigment Red 51 [C.I. 15580, (CAS: 5850-87-3)], Pigment Red 52 [C.I. 15860, (CAS: 5858-82-2)], Pigment Red 52 [C.I. 15860, (CAS: 1325-11-7)], Pigment Red 52 [C.I. 15860, (CAS: 17852-99-2)], Pigment Red 52 [C.I. 15860, (CAS: 17814-20-9)], Pigment Red 52 [C.I. 15860, (CAS: 12238-31-2)], Pigment Red 53 [C.I. 15585, (CAS: 2092-56-0)], Pigment Red 53 [C.I. 15585, (CAS: 1325-04-8)], Pigment Red 53 [C.I. 15585, (CAS: 67990-35-6)], Pigment Red 53 [C.I. 15585, (CAS: 73263-40-8)], Pigment Red 54 [C.I. 14830, (CAS: 6373-10-0)], Pigment Red 55 [C.I. 15820, (CAS: 141052-43-9)], Pigment Red 57 [C.I. 15850, (CAS: 5858-81-1)], Pigment Red 57 [C.I. 15850, (CAS: 17852-98-1)], Pigment Red 57 [C.I. 15850, (CAS: 55491-44-6)], Pigment Red 58 [C.I. 15825, (CAS: 1325-09-3)], Pigment Red 58 [C.I. 15825, (CAS: 7538-59-2)], Pigment Red 58 [CI 15825, (CAS: 15782-03-3)], Pigment Red 58 [C.I. 15825, (CAS: 76613-71-3)], Pigment Red 58 [C.I. 15825, (CAS: 64552-28-9)], Pigment Red 6 [C.I. 12090, (CAS: 6410-13-5)], Pigment Red 60 [C.I. 16105, (CAS: 15782-06-6)], Pigment Red 60 [C.I. 16105, (CAS: 1325-16-2)], Pigment Red 61 [C.I. 24830, (CAS: 1325-29-7)], Pigment Red 62 [C.I. 23295, (CAS: 109823-18-9)], Pigment Red 63 [C.I. 15880, (CAS: 21416-46-6)], Pigment Red 63 [C.I. 15880, (CAS: 6417-83-0)], Pigment Red 63 [C.I. 15880, (CAS: 15792-20-8)], Pigment Red 63 [C.I. 15880, (CAS: 35355-77-2)], Pigment Red 64 [C.I. 15800, (CAS: 16508-79-5)], Pigment Red 64 [C.I. 15800, (CAS: 6371-76-2)], Pigment Red 65 [C.I. 18020, (CAS: 1325-21-9)], Pigment Red 66 [C.I. 18000, (CAS: 1325-19-5)], Pigment Red 67 [C.I. 18025, (CAS: 1325-22-0)], Pigment Red 68 [C.I. 15525, (CAS: 5850-80-6)], Pigment Red 69 [C.I. 15595, (CAS: 5850-90-8)], Pigment Red 7 [C.I. 12420, (CAS: 6471-51-8)], Pigment Red 70 [C.I. 15590, (CAS: 5850-89-5)], Pigment Red 77 [C.I. 15826, (CAS: 6358-39-0)], Pigment Red 8 [C.I. 12335, (CAS: 6410-30-6)], Pigment Red 83 [C.I. 58000, (CAS: 104074-25-1)], Pigment Red 84 [C.I. 58210, (CAS: 1328-07-0)], Pigment Red 85 [C.I. 63350, (CAS: 6370-96-3)], Pigment Red 86 [C.I. 73375, (CAS: 6371-26-2)], Pigment Red 89 [C.I. 60745, (CAS: 6409-74-1)], Pigment Red 9 [C.I. 12460, (CAS: 6410-38-4)], Pigment Red 90 [C.I. 45380, (CAS: 15876-39-8)], Pigment Red 93 [C.I. 12152, (CAS: 6548-36-3)], Pigment Red 95 [C.I. 15897, (CAS: 72639-39-5)], Pigment Red 99 [C.I. 15570, (CAS: 5850-85-1)], Pigment Violet 10 [C.I. 42535, (CAS: 1325-82-2)], Pigment Violet 12 [C.I. 58050, (CAS: 1328-03-6)], Pigment Violet 13 [C.I. 125085, (CAS: 83399-83-1)], Pigment Violet 14 [C.I. 77360, (CAS: 10101-56-1)], Pigment Violet 15 [C.I. 77007, (CAS: 12769-96-9)], Pigment Violet 16 [C.I. 77742, (CAS: 10101-66-3)], Pigment Violet 19 [C.I. 46500, (CAS: 1047-16-0], Pigment Violet 20 [C.I. 58225, (CAS: 6486-92-6)], Pigment Violet 23 [C.I. 51319, (CAS: 215247-95-3)], Pigment Violet 25 [C.I. 12321, (CAS: 6358-46-9)], Pigment Violet 27 [C.I. 42535, (CAS: 12237-62-6)], Pigment Violet 29 [C.I. 71129, (CAS: 81-33-4)], Pigment Violet 3 [C.I. 42535, (CAS: 68647-35-8)], Pigment Violet 3 [C.I. 42535, (CAS: 68308-41-8)], Pigment Violet 3 [C.I. 42535, (CAS: 67989-22-4)], Pigment Violet 31 [C.I. 60010, (CAS: 1324-55-6)], Pigment Violet 33 [C.I. 60005, (CAS: 1324-17-0)], Pigment Violet 36 [C.I. 73385, (CAS: 5462-29-3)], Pigment Violet 37 [C.I. 51345, (CAS: 17741-63-8)], Pigment Violet 38 [C.I. 73395, (CAS: 2379-75-1)], Pigment Violet 47 [C.I. 77363, (CAS: 68610-13-9)], Pigment Violet 48 [C.I. 77352, (CAS: 68608-93-5)], Pigment Violet 49 [C.I. 77362, (CAS: 16827-96-6)], Pigment Violet 5 [C.I. 58055, (CAS: 1328-04-7)], Pigment Violet 6 [C.I. 58060, (CAS: 6483-85-8)], Pigment Violet 6 [C.I. 58060, (CAS: 1328-05-8)], Pigment Violet 7 [C.I. 58065, (CAS: 1328-06-9)], Pigment Violet 8 [C.I. 18005, (CAS: 1325-20-8)], Pigment Yellow 1 [C.I. 11680, (CAS: 2512-29-0)], Pigment Yellow 10 [C.I. 12710, (CAS: 6407-75-6)], Pigment Yellow 100 [C.I. 19140, (CAS: 12225-21-7)], Pigment Yellow 104 [C.I. 15985, (CAS: 15790-07-5)], Pigment Yellow 105 [C.I. 11743, (CAS: 12236-75-8)], Pigment Yellow 109 [C.I. 56284, (CAS: 5045-40-9)], Pigment Yellow 11 [C.I. 10325, (CAS: 2955-16-0)], Pigment Yellow 110 [C.I. 56280, (CAS: 5590-18-1)], Pigment Yellow 111 [C.I. 11745, (CAS: 15993-42-7)], Pigment Yellow 112 [C.I. 70600, (CAS: 475-71-8)], Pigment Yellow 114 [C.I. 21092, (CAS: 68610-87-7)], Pigment Yellow 115 [C.I. 47005, (CAS: 68814-04-0)], Pigment Yellow 116 [C.I. 11790, (CAS: 61968-84-1)], Pigment Yellow 117 [C.I. 48043, (CAS: 21405-81-2)], Pigment Yellow 118 [C.I. 77894, (CAS: 61512-65-0)], Pigment Yellow 119 [C.I. 77496, (CAS: 68187-51-9)], Pigment Yellow 12 [C.I. 21090, (CAS: 6358-85-6)], Pigment Yellow 123 [C.I. 65049, (CAS: 4028-94-8)], Pigment Yellow 124 [C.I. 21107, (CAS: 67828-22-2)], Pigment Yellow 126 [C.I. 21101, (CAS: 90268-23-8)], Pigment Yellow 127 [C.I. 21102, (CAS: 68610-86-6)], Pigment Yellow 128 [C.I. 20037, (CAS: 79953-85-8)], Pigment Yellow 129 [C.I. 48042, (CAS: 15680-42-9)], Pigment Yellow 13 [C.I. 21100, (CAS: 5102-83-0)], Pigment Yellow 130 [C.I. 117699, (CAS: 23739-66-4)], Pigment Yellow 133 [C.I. 139395, (CAS: 85702-53-0)], Pigment Yellow 134 [C.I. 21111, (CAS: 31775-20-9)], Pigment Yellow 138 [C.I. 56300, (CAS: 30125-47-4)], Pigment Yellow 139 [C.I. 56298, (CAS: 36888-99-0)], Pigment Yellow 14 [C.I. 21095, (CAS: 5468-75-7)], Pigment Yellow 147 [C.I. 60645, (CAS: 4118-16-5)], Pigment Yellow 148 [C.I. 50600, (CAS: 20572-37-6)], Pigment Yellow 15 [C.I. 21220, (CAS: 6528-35-4)], Pigment Yellow 150 [C.I. 12764, (CAS: 872613-79-1)], Pigment Yellow 153 [C.I. 48545, (CAS: 29204-84-0)], Pigment Yellow 155 [C.I. 200310, (CAS: 68516-73-4)], Pigment Yellow 157 [C.I. 77900, (CAS: 68610-24-2)], Pigment Yellow 158 [C.I. 77862, (CAS: 68186-93-6)], Pigment Yellow 159 [C.I. 77997, (CAS: 68187-15-5)], Pigment Yellow 16 [C.I. 20040, (CAS: 5979-28-2)], Pigment Yellow 160 [C.I. 77991, (CAS: 68187-01-9)], Pigment Yellow 161 [C.I. 77895, (CAS: 68611-43-8)], Pigment Yellow 162 [C.I. 77896, (CAS: 68611-42-7)], Pigment Yellow 163 [C.I. 77897, (CAS: 68186-92-5)], Pigment Yellow 164 [C.I. 77899, (CAS: 68412-38-4)], Pigment Yellow 167 [C.I. 11737, (CAS: 38489-24-6)], Pigment Yellow 168 [C.I. 13960, (CAS: 71832-85-4)], Pigment Yellow 169 [C.I. 13955, (CAS: 73385-03-2)], Pigment Yellow 17 [C.I. 21105, (CAS: 4531-49-1)], Pigment Yellow 173 [C.I. 561600, (CAS: 51016-63-8)], Pigment Yellow 174 [C.I. 21098, (CAS: 78952-72-4)], Pigment Yellow 176 [C.I. 21103, (CAS: 90268-24-9)], Pigment Yellow 177 [C.I. 48120, (CAS: 60109-88-8)], Pigment Yellow 179 [C.I. 48125, (CAS: 63287-28-5)], Pigment Yellow 180 [C.I. 21290, (CAS: 77804-81-0)], Pigment Yellow 181 [C.I. 11777, (CAS: 74441-05-7)], Pigment Yellow 182 [C.I. 128300, (CAS: 67906-31-4)], Pigment Yellow 183 [C.I. 18792, (CAS: 65212-77-3)], Pigment Yellow 184 [C.I. 771740, (CAS: 14059-33-7)], Pigment Yellow 185 [C.I. 56290, (CAS: 76199-85-4)], Pigment Yellow 188 [C.I. 21094, (CAS: 23792-68-9)], Pigment Yellow 190 [C.I. 189785, (CAS: 94612-75-6)], Pigment Yellow 191 [C.I. 18795, (CAS: 129423-54-7)], Pigment Yellow 191 [C.I. 18795, (CAS: 154946-66-4)], Pigment Yellow 192 [C.I. 507300, (CAS: 56279-27-7)], Pigment Yellow 193 [C.I. 65412, (CAS: 70321-14-1)], Pigment Yellow 194 [C.I. 11785, (CAS: 82199-12-0)], Pigment Yellow 199 [C.I. 653200, (CAS: 136897-58-0)], Pigment Yellow 2 [C.I. 11730, (CAS: 6486-26-6)], Pigment Yellow 202 [C.I. 65410, (CAS: 3627-47-2)], Pigment Yellow 203 [C.I. 117390, (CAS: 150959-17-4)], Pigment Yellow 213 [C.I. 117875, (CAS: 220198-21-0)], Pigment Yellow 218 [C.I. 561805, (CAS: 910868-14-3)], Pigment Yellow 220 [C.I. 561806, (CAS: 17352-39-5)], Pigment Yellow 227 [C.I. 777895, (CAS: 1374645-21-2)], Pigment Yellow 3 [C.I. 11710, (CAS: 6486-23-3)], Pigment Yellow 30 [C.I. 77592, (CAS: 1345-30-8)], Pigment Yellow 31 [C.I. 77103, (CAS: 10294-40-3)], Pigment Yellow 33 [C.I. 77223, (CAS: 8012-75-7)], Pigment Yellow 34 [C.I. 77603, (CAS: 1344-37-2)], Pigment Yellow 35 [C.I. 77205, (CAS: 90604-89-0)], Pigment Yellow 36 [C.I. 77956, (CAS: 49663-84-5)], Pigment Yellow 37 [C.I. 77199, (CAS: 90604-90-3)], Pigment Yellow 38 [C.I. 77878, (CAS: 1315-01-1)], Pigment Yellow 39 [C.I. 77086, (CAS: 1303-33-9)], Pigment Yellow 4 [C.I. 11665, (CAS: 1657-16-5)], Pigment Yellow 41 [C.I. 77588, (CAS: 8012-00-8)], Pigment Yellow 42 [C.I. 77492, (CAS: 51274-00-1)], Pigment Yellow 43 [C.I. 77492, (CAS: 64294-91-3)], Pigment Yellow 44 [C.I. 77188, (CAS: 1345-08-0)], Pigment Yellow 45 [C.I. 77505, (CAS: 1328-64-9)], Pigment Yellow 46 [C.I. 77577, (CAS: 1317-36-8)], Pigment Yellow 48 [C.I. 77610, (CAS: 592-05-2)], Pigment Yellow 5 [C.I. 11660, (CAS: 4106-67-6)], Pigment Yellow 53 [C.I. 77788, (CAS: 8007-18-9)], Pigment Yellow 55 [C.I. 21096, (CAS: 6358-37-8)], Pigment Yellow 6 [C.I. 11670, (CAS: 4106-76-7)], Pigment Yellow 60 [C.I. 12705, (CAS: 6407-74-5)], Pigment Yellow 61 [C.I. 13880, (CAS: 5280-69-3)], Pigment Yellow 62 [C.I. 13940, (CAS: 12286-66-7)], Pigment Yellow 62 [C.I. 13940, (CAS: 5280-70-6)], Pigment Yellow 65 [C.I. 11740, (CAS: 6528-34-3)], Pigment Yellow 7 [C.I. 12780, (CAS: 6407-81-4)], Pigment Yellow 73 [C.I. 11738, (CAS: 13515-40-7)], Pigment Yellow 74 [C.I. 11741, (CAS: 6358-31-2)], Pigment Yellow 75 [C.I. 11770, (CAS: 52320-66-8)], Pigment Yellow 77 [C.I. 20045, (CAS: 5905-17-9)], Pigment Yellow 81 [C.I. 21127, (CAS: 22094-93-5)], Pigment Yellow 83 [C.I. 21108, (CAS: 5567-15-7)], Pigment Yellow 83 [C.I. 21107, (CAS: 15110-84-6)], Pigment Yellow 9 [C.I. 11720, (CAS: 6486-24-4)], Pigment Yellow 93 [C.I. 20710, (CAS: 5580-57-4)], Pigment Yellow 94 [C.I. 20038, (CAS: 5580-58-5)], Pigment Yellow 95 [C.I. 20034, (CAS: 5280-80-8)], Pigment Yellow 98 [C.I. 11727, (CAS: 32432-45-4)], Prussian blue [C.I. 77510, (CAS: 12240-15-2)], Pigment Blue 1 [(CAS: 1325-87-7)], Pigment Blue 1 [(CAS: 69980-72-9)], Pigment Blue 1 [(CAS: 68409-66-5)], Pigment Blue 10 [(CAS: 84057-86-3)], Pigment Blue 12 [(CAS: 1325-77-5)], Pigment Blue 14 [(CAS: 1325-88-8)], Pigment Blue 2 [(CAS: 1325-94-6)], Pigment Blue 3 [(CAS: 1325-79-7)], Pigment Blue 9 [(CAS: 1325-74-2)], Pigment Green 1 [(CAS: 1325-75-3)], Pigment Green 3 [(CAS: 68845-37-4)], Pigment Green 4 [(CAS: 61725-50-6)], Pigment Red 80 [(CAS: 12224-98-5)], Pigment Red 81 [(CAS: 80083-40-5)], Pigment Red 81 [(CAS: 75627-12-2)], Pigment Red 81 [(CAS: 68310-07-6)], Pigment Red 81 [(CAS: 85959-61-1)], Pigment Red 81 [(CAS: 63022-06-0)], Pigment Red 81 [(CAS: 63022-07-1)], Pigment Violet 1 [(CAS: 1326-03-0)], Pigment Violet 2 [(CAS: 1326-04-1)], Pigment Violet 2 [(CAS: 103443-41-0)], Pigment Violet 4 [(CAS: 1325-80-0)], Pigment Black 1 [(CAS: 73104-73-0], Pigment Black 1 [(CAS: 9064-44-2)], Pigment Black 11 [(CAS: 120899-48-1)], Pigment Black 11 [(CAS: 128666-38-6)], Pigment Black 11 [(CAS: 128666-37-5)], Pigment Black 11 [(CAS: 128666-36-4)], Pigment Black 11 [(CAS: 147858-25-1)], Pigment Black 16 [(CAS: 7440-66-6)], Pigment Black 19 [(CAS: 874954-47-9)], Pigment Black 2 [(CAS: 12236-57-6)], Pigment Black 20 [(CAS: 12216-93-2)], Pigment Black 21 [(CAS: 12216-94-3)], Pigment Black 22 [(CAS: 55353-02-1)], Pigment Black 3 [(CAS: 945563-42-8)], Pigment Black 35 [(CAS: 945563-51-9)], Pigment Black 5 [(CAS: 945563-45-1)], Pigment Blue 1 [(CAS: 68647-33-6)], Pigment Blue 10 [(CAS: 308086-15-9)], Pigment Blue 11 [(CAS: 71798-70-4)], Pigment Blue 13 [(CAS: 945558-73-6)], Pigment Blue 15-Pigment Green 7 mixt. [(CAS: 1026025-11-5)], Pigment Blue 15-Pigment Red 122-Pigment Yellow 74 mixt. [(CAS: 1357447-02-9)], Pigment Blue 151 [(CAS: 685529-31-1)], Pigment Blue 16 [(CAS: 424827-05-4)], Pigment Blue 17 [(CAS: 153640-87-0)], Pigment Blue 17 [(CAS: 71799-04-7)], Pigment Blue 19 [(CAS: 58569-23-6)], Pigment Blue 2 [(CAS: 1126074-38-1)], Pigment Blue 20 [(CAS: 945558-74-7)], Pigment Blue 209 [(CAS: 215590-82-2)], Pigment Blue 23 [(CAS: 57486-30-3)], Pigment Blue 24 [(CAS: 1042940-03-3)], Pigment Blue 28 [(CAS: 151732-17-1)], Pigment Blue 29 [(CAS: 151732-19-3)], Pigment Blue 31 [(CAS: 945558-75-8)], Pigment Blue 4 [(CAS: 945558-70-3)], Pigment Blue 5 [(CAS: 945558-72-5)], Pigment Blue 52 [(CAS: 945558-90-7)], Pigment Blue 53 [(CAS: 945558-91-8)], Pigment Blue 53 [(CAS: 190454-42-3)], Pigment Blue 56 [(CAS: 64427-27-6)], Pigment Blue 58 [(CAS: 12236-58-7)], Pigment Blue 59 [(CAS: 12236-59-8)], Pigment Blue 6 [(CAS: 371759-37-4)], Pigment Blue 61 [(CAS: 1126075-97-5)], Pigment Blue 63 [(CAS: 815586-00-6)], Pigment Blue 67 [(CAS: 945558-93-0)], Pigment Blue 68 [(CAS: 129406-28-6)], Pigment Blue 69 [(CAS: 945558-94-1)], Pigment Blue 7 [(CAS: 71838-91-0)], Pigment Blue 7 [(CAS: 120177-75-5)], Pigment Blue 70 [(CAS: 72827-99-7)], Pigment Blue 77 [(CAS: 945558-95-2)], Pigment Blue 8 [(CAS: 12224-90-7)], Pigment Blue 80 [(CAS: 391663-82-4)], Pigment Blue 81 [(CAS: 945558-98-5)], Pigment Blue 83 [(CAS: 1126076-49-0)], Pigment Blue 84 [(CAS: 2095508-48-6)], Pigment Brown 126 [(CAS: 128664-60-8)], Pigment Brown 29 [(CAS: 109414-04-2)], Pigment Brown 3 [(CAS: 1325-24-2)], Pigment Brown 30 [(CAS: 135668-57-4)], Pigment Brown 31 [(CAS: 126338-71-4)], Pigment Brown 32 [(CAS: 72828-00-3)], Pigment Brown 36 [(CAS: 945563-08-6)], Pigment Brown 4 [(CAS: 109944-91-4)], Pigment Brown 40 [(CAS: 945563-13-3)], Pigment Brown 41 [(CAS: 211502-16-8)], Pigment Brown 42 [(CAS: 211502-17-9)], Pigment Brown 43 [(CAS: 75864-23-2)], Pigment Brown 44 [(CAS: 945563-18-8)], Pigment Brown 45 [(CAS: 945563-37-1)], Pigment Brown 46 [(CAS: 945563-38-2)], Pigment Brown 47 [(CAS: 945563-39-3)], Pigment Brown 48 [(CAS: 2170864-80-7)], Pigment Brown 5 [(CAS: 16521-34-9)], Pigment Brown 6 [(CAS: 1275574-14-5)], Pigment Green 1 [(CAS: 68814-00-6)], Pigment Green 1 [(CAS: 68123-12-6)], Pigment Green 13 [(CAS: 148092-61-9)], Pigment Green 14 [(CAS: 114013-40-0)], Pigment Green 16 [(CAS: 65505-26-2)], Pigment Green 2 [(CAS: 12213-69-3)], Pigment Green 2 [(CAS: 76963-33-2)], Pigment Green 25 [(CAS: 945560-75-8)], Pigment Green 45 [(CAS: 945561-

39-7)], Pigment Green 46 [(CAS: 945561-40-0)], Pigment Green 48 [(CAS: 945561-55-7)], Pigment Green 49 [(CAS: 945561-56-8)], Pigment Green 52 [(CAS: 945562-08-3)], Pigment Green 55 [(CAS: 945563-02-0)], Pigment Green 56 [(CAS: 945563-05-3)], Pigment Green 59 [(CAS: 2170445-83-5)], Pigment Green 6 [(CAS: 945559-56-8)], Pigment Green 62 [(CAS: 2108056-55-7)], Pigment Green 63 [(CAS: 2108056-56-8)], Pigment Green 7 [(CAS: 68022-83-3)], Pigment Green 77 [(CAS: 12715-62-7)], Pigment Green 7-Pigment Yellow 93 mixt. [(CAS: 1046461-83-9)], Pigment Orange 12 [(CAS: 945426-49-3)], Pigment Orange 20 [(CAS: 957128-28-8)], Pigment Orange 25 [(CAS: 12224-97-4)], Pigment Orange 32 [(CAS: 945426-51-7)], Pigment Orange 36 [(CAS: 12236-62-3)], Pigment Orange 38 [(CAS: 12236-64-5)], Pigment Orange 42 [(CAS: 12768-99-9)], Pigment Orange 43-Pigment Orange 64 mixt. [(CAS: 1046461-84-0)], Pigment Orange 47 [(CAS: 71819-73-3)], Pigment Orange 48 [(CAS: 71819-74-4)], Pigment Orange 49 [(CAS: 71819-75-5)], Pigment Orange 50 [(CAS: 76780-89-7)], Pigment Orange 51 [(CAS: 61512-61-6)], Pigment Orange 52 [(CAS: 61512-62-7)], Pigment Orange 53 [(CAS: 945426-52-8)], Pigment Orange 54 [(CAS: 945426-53-9)], Pigment Orange 55 [(CAS: 304891-88-1)], Pigment Orange 56 [(CAS: 74433-73-1)], Pigment Orange 57 [(CAS: 945426-54-0)], Pigment Orange 58 [(CAS: 945426-55-1)], Pigment Orange 59 [(CAS: 304891-93-8)], Pigment Orange 60 [(CAS: 68399-99-5)], Pigment Orange 62 [(CAS: 52846-56-7)], Pigment Orange 63 [(CAS: 76233-79-9)], Pigment Orange 70 [(CAS: 914936-31-5)], Pigment Orange 74 [(CAS: 516493-26-8)], Pigment Orange 76 [(CAS: 945426-61-9)], Pigment Orange 79 [(CAS: 945426-62-0)], Pigment Orange 8 [(CAS: 945426-48-2)], Pigment Orange 80 [(CAS: 945426-63-1)], Pigment Orange 81 [(CAS: 656223-72-2)], Pigment Orange 82 [(CAS: 2170864-77-2)], Pigment Orange 86 [(CAS: 1883421-38-2)], Pigment Orange 9 [(CAS: 71799-05-8)], Pigment Red 1 [(CAS: 39781-24-3)], Pigment Red 102 [(CAS: 1332-25-8)], Pigment Red 108 [(CAS: 918496-78-3)], Pigment Red 110 [(CAS: 854102-21-9)], Pigment Red 111 [(CAS: 12224-99-6)], Pigment Red 118 [(CAS: 945428-13-7)], Pigment Red 120 [(CAS: 57485-96-8)], Pigment Red 123 [(CAS: 24108-89-2)], Pigment Red 134 [(CAS: 12286-59-8)], Pigment Red 135 [(CAS: 945428-14-8)], Pigment Red 136 [(CAS: 945428-21-7)], Pigment Red 137 [(CAS: 71799-07-0)], Pigment Red 139 [(CAS: 12262-44-1)], Pigment Red 140 [(CAS: 383890-12-8)], Pigment Red 142 [(CAS: 109944-97-0)], Pigment Red 143 [(CAS: 12286-63-4)], Pigment Red 152 [(CAS: 405113-25-9)], Pigment Red 154 [(CAS: 109944-98-1)], Pigment Red 155 [(CAS: 109944-99-2)], Pigment Red 156 [(CAS: 109945-00-8)], Pigment Red 158 [(CAS: 945552-90-9)], Pigment Red 159 [(CAS: 109945-01-9)], Pigment Red 160 [(CAS: 854524-60-0)], Pigment Red 161 [(CAS: 945552-91-0)], Pigment Red 165 [(CAS: 12225-03-5)], Pigment Red 167 [(CAS: 12236-66-7)], Pigment Red 176 [(CAS: 12225-06-8)], Pigment Red 178 [(CAS: 3049-71-6)], Pigment Red 17-Pigment Red 150-Pigment White 18 mixt. [(CAS: 2247196-29-6)], Pigment Red 180 [(CAS: 12769-00-5)], Pigment Red 182 [(CAS: 61036-51-9)], Pigment Red 183 [(CAS: 51920-11-7)], Pigment Red 191 [(CAS: 85068-75-3)], Pigment Red 199 [(CAS: 61901-78-8)], Pigment Red 20 [(CAS: 945426-74-4)], Pigment Red 200 [(CAS: 67801-10-9)], Pigment Red 201 [(CAS: 68258-66-2)], Pigment Red 202-Pigment Violet 19 mixt. [(CAS: 1122063-75-5)], Pigment Red 203 [(CAS: 945553-87-7)], Pigment Red 204 [(CAS: 438231-79-9)], Pigment Red 205 [(CAS: 741692-71-7)], Pigment Red 206 [(CAS: 71819-76-6)], Pigment Red 207 [(CAS: 71819-77-7)], Pigment Red 215 [(CAS: 304892-29-3)], Pigment Red 217 [(CAS: 155421-17-3)], Pigment Red 218 [(CAS: 383891-32-5)], Pigment Red 219 [(CAS: 909006-21-9)], Pigment Red 223 [(CAS: 26789-26-4)], Pigment Red 225 [(CAS: 125270-32-8)], Pigment Red 227 [(CAS: 71872-64-5)], Pigment Red 228 [(CAS: 304898-64-4)], Pigment Red 234 [(CAS: 945554-26-7)], Pigment Red 237 [(CAS: 220424-27-1)], Pigment Red 238 [(CAS: 140114-63-2)], Pigment Red 239 [(CAS: 220424-28-2)], Pigment Red 240 [(CAS: 141489-67-0)], Pigment Red 241 [(CAS: 945554-27-8)], Pigment Red 244 [(CAS: 882858-66-4)], Pigment Red 245 [(CAS: 68016-05-7)], Pigment Red 246 [(CAS: 431991-59-2)], Pigment Red 249 [(CAS: 97955-62-9)], Pigment Red 25 [(CAS: 945426-75-5)], Pigment Red 250 [(CAS: 146358-78-3)], Pigment Red 252 [(CAS: 945554-31-4)], Pigment Red 26 [(CAS: 109944-92-5)], Pigment Red 262 [(CAS: 211502-19-1)], Pigment Red 263 [(CAS: 278792-06-6)], Pigment Red 270 [(CAS: 251086-13-2)], Pigment Red 272 [(CAS: 350249-32-0)], Pigment Red 276 [(CAS: 945554-32-5)], Pigment Red 277 [(CAS: 945554-33-6)], Pigment Red 278 [(CAS: 945554-34-7)], Pigment Red 279 [(CAS: 832743-59-6)], Pigment Red 280 [(CAS: 945554-58-5)], Pigment Red 281 [(CAS: 945554-64-3)], Pigment Red 282 [(CAS: 938065-79-3)], Pigment Red 283 [(CAS: 945554-67-6)], Pigment Red 284 [(CAS: 1089180-60-8)], Pigment Red 285 [(CAS: 1248412-35-2)], Pigment Red 29 [(CAS: 109944-93-6)], Pigment Red 34 [(CAS: 71872-60-1)], Pigment Red 35 [(CAS: 104491-86-3)], Pigment Red 46 [(CAS: 945427-33-8)], Pigment Red 47 [(CAS: 945427-55-4)], Pigment Red 48 [(CAS: 16013-44-8)], Pigment Red 48 [(CAS: 17797-35-2)], Pigment Red 48-Pigment Red 122 mixt. [(CAS: 1046461-81-7)], Pigment Red 48 [(CAS: 218138-44-4)], Pigment Red 48 [(CAS: 218138-41-1)], Pigment Red 48 [(CAS: 68023-17-6)], Pigment Red 51 [(CAS: 25705-30-0)], Pigment Red 51 [(CAS: 446242-29-1)], Pigment Red 52 [(CAS: 27757-95-5)], Pigment Red 52 [(CAS: 67828-72-2)], Pigment Red 52 [(CAS: 218138-27-3)], Pigment Red 53 [(CAS: 15958-19-7)], Pigment Red 56 [(CAS: 25310-96-7)], Pigment Red 57 [(CAS: 88593-07-1)], Pigment Red 58 [(CAS: 25310-97-8)], Pigment Red 59 [(CAS: 945427-99-6)], Pigment Red 60 [(CAS: 446245-60-9)], Pigment Red 63 [(CAS: 5858-84-4)], Pigment Red 63 [(CAS: 16510-21-7)], Pigment Red 63 [(CAS: 1325-13-9)], Pigment Red 64 [(CAS: 5858-77-5)], Pigment Red 68 [(CAS: 25311-19-7)], Pigment Red 71 [(CAS: 384329-78-6)], Pigment Red 72 [(CAS: 945428-03-5)], Pigment Red 73 [(CAS: 109944-94-7)], Pigment Red 74 [(CAS: 109944-95-8)], Pigment Red 75 [(CAS: 109944-96-9)], Pigment Red 78 [(CAS: 71799-06-9)], Pigment Red 81-Pigment White 21 mixt. [(CAS: 192390-71-9)], Pigment Red 82 [(CAS: 110927-51-0)], Pigment Red 88 [(CAS: 14295-43-3)], Pigment Red 90 [(CAS: 51868-24-7)], Pigment Red 92 [(CAS: 909006-04-8)], Pigment Red 94 [(CAS: 12213-62-6)], Pigment Red 96 [(CAS: 945428-04-6)], Pigment Red 97 [(CAS: 239795-92-7)], Pigment Red 98 [(CAS: 945428-07-9)], Pigment Violet 1 [(CAS: 63022-09-3)], Pigment Violet 1 [(CAS: 62973-79-9)], Pigment Violet 11 [(CAS: 875014-31-6)], Pigment Violet 11 [(CAS: 765310-46-1)], Pigment Violet 122 [(CAS: 104491-87-4)], Pigment Violet 123 [(CAS: 80619-33-6)], Pigment Violet 17 [(CAS: 945554-69-8)], Pigment Violet 18 [(CAS: 945554-81-4)], Pigment Violet 21 [(CAS: 945555-53-3)], Pigment Violet 26 [(CAS: 945556-80-9)], Pigment Violet 28 [(CAS: 12236-70-3)], Pigment Violet 30 [(CAS: 12225-07-9)], Pigment Violet 32 [(CAS: 12225-08-0)], Pigment Violet 34 [(CAS: 12612-32-7)], Pigment Violet 35 [(CAS: 55177-94-0)], Pigment Violet 39 [(CAS: 64070-98-0)], Pigment Violet 39 [(CAS: 68477-

21-4)], Pigment Violet 4 [(CAS: 68310-88-3)], Pigment Violet 40 [(CAS: 61968-83-0)], Pigment Violet 41 [(CAS: 945557-07-3)], Pigment Violet 42 [(CAS: 71819-79-9)], Pigment Violet 43 [(CAS: 79665-29-5)], Pigment Violet 44 [(CAS: 87209-55-0)], Pigment Violet 45 [(CAS: 945557-40-4)], Pigment Violet 46 [(CAS: 945557-42-6)], Pigment Violet 5 [(CAS: 22297-70-7)], Pigment Violet 50 [(CAS: 76233-81-3)], Pigment Violet 51 [(CAS: 945557-43-7)], Pigment Violet 52 [(CAS: 945557-99-3)], Pigment Violet 53 [(CAS: 945558-15-6)], Pigment Violet 54 [(CAS: 1126076-80-9)], Pigment Violet 55 [(CAS: 1126076-86-5)], Pigment Violet 56 [(CAS: 1126076-93-4)], Pigment Violet 7 [(CAS: 16035-60-2)], Pigment Violet 9 [(CAS: 945554-68-7)], Pigment Yellow 1 [(CAS: 12240-03-8)], Pigment Yellow 102 [(CAS: 12236-74-7)], Pigment Yellow 103 [(CAS: 12225-22-8)], Pigment Yellow 106 [(CAS: 12225-23-9)], Pigment Yellow 107 [(CAS: 12270-64-3)], Pigment Yellow 113 [(CAS: 14359-20-7)], Pigment Yellow 120 [(CAS: 29920-31-8)], Pigment Yellow 121 [(CAS: 14569-54-1)], Pigment Yellow 122 [(CAS: 852620-87-2)], Pigment Yellow 125 [(CAS: 304891-45-0)], Pigment Yellow 131 [(CAS: 945423-41-6)], Pigment Yellow 132 [(CAS: 945424-04-4)], Pigment Yellow 135 [(CAS: 945424-77-1)], Pigment Yellow 136 [(CAS: 181285-33-6)], Pigment Yellow 140 [(CAS: 945425-58-1)], Pigment Yellow 141 [(CAS: 945425-59-2)], Pigment Yellow 142 [(CAS: 177020-91-6)], Pigment Yellow 143 [(CAS: 945425-60-5)], Pigment Yellow 144 [(CAS: 945425-61-6)], Pigment Yellow 145 [(CAS: 115742-72-8)], Pigment Yellow 146 [(CAS: 945425-66-1)], Pigment Yellow 149 [(CAS: 945425-67-2)], Pigment Yellow 150 [(CAS: 939382-97-5)], Pigment Yellow 151 [(CAS: 31837-42-0)], Pigment Yellow 154 [(CAS: 68134-22-5)], Pigment Yellow 156 [(CAS: 63661-26-7)], Pigment Yellow 165 [(CAS: 865763-85-5)], Pigment Yellow 166 [(CAS: 76233-82-4)], Pigment Yellow 170 [(CAS: 31775-16-3)], Pigment Yellow 171 [(CAS: 53815-04-6)], Pigment Yellow 172 [(CAS: 76233-80-2)], Pigment Yellow 175 [(CAS: 35636-63-6)], Pigment Yellow 178 [(CAS: 945425-73-0)], Pigment Yellow 17 [(CAS: 221358-38-9)], Pigment Yellow 18 [(CAS: 1326-11-0)], Pigment Yellow 18 [(CAS: 68310-89-4)], Pigment Yellow 186 [(CAS: 945425-92-3)], Pigment Yellow 187 [(CAS: 131439-24-2)], Pigment Yellow 189 [(CAS: 69011-05-8)], Pigment Yellow 191 [(CAS: 1051932-58-1)], Pigment Yellow 195 [(CAS: 135668-58-5)], Pigment Yellow 196 [(CAS: 945425-96-7)], Pigment Yellow 197 [(CAS: 945425-97-8)], Pigment Yellow 198 [(CAS: 516493-10-0)], Pigment Yellow 20 [(CAS: 61512-63-8)], Pigment Yellow 200 [(CAS: 945425-98-9)], Pigment Yellow 201 [(CAS: 945425-99-0)], Pigment Yellow 204 [(CAS: 945426-05-1)], Pigment Yellow 205 [(CAS: 945426-18-6)], Pigment Yellow 206 [(CAS: 945426-19-7)], Pigment Yellow 207 [(CAS: 945426-23-3)], Pigment Yellow 208 [(CAS: 945426-25-5)], Pigment Yellow 209 [(CAS: 945426-27-7)], Pigment Yellow 21 [(CAS: 945421-49-8)], Pigment Yellow 210 [(CAS: 945426-35-7)], Pigment Yellow 211 [(CAS: 945426-36-8)], Pigment Yellow 212 [(CAS: 945426-37-9)], Pigment Yellow 214 [(CAS: 577980-23-5)], Pigment Yellow 215 [(CAS: 913621-26-8)], Pigment Yellow 216 [(CAS: 817181-98-9)], Pigment Yellow 217 [(CAS: 945426-39-1)], Pigment Yellow 219 [(CAS: 874963-72-1)], Pigment Yellow 221 [(CAS: 945426-41-5)], Pigment Yellow 223 [(CAS: 2095507-47-2)], Pigment Yellow 224 [(CAS: 1207669-05-3)], Pigment Yellow 23 [(CAS: 4981-43-5)], Pigment Yellow 231 [(CAS: 2148300-50-7)], Pigment Yellow 25 [(CAS: 945421-63-6)], Pigment Yellow 26 [(CAS: 945421-64-7)], Pigment Yellow 27 [(CAS: 945421-65-8)], Pigment Yellow 28 [(CAS: 945421-66-9)], Pigment Yellow 29 [(CAS: 945421-67-0)], Pigment Yellow 34 [(CAS: 147858-25-1)], Pigment Yellow 36 [(CAS: 37300-23-5)], Pigment Yellow 37 [(CAS: 68859-25-6)], Pigment Yellow 40 [(CAS: 13782-01-9)], Pigment Yellow 47 [(CAS: 12060-00-3)], Pigment Yellow 50 [(CAS: 945421-71-6)], Pigment Yellow 51 [(CAS: 945421-76-1)], Pigment Yellow 56 [(CAS: 12225-09-1)], Pigment Yellow 58 [(CAS: 12225-11-5)], Pigment Yellow 61 [(CAS: 12286-65-6)], Pigment Yellow 72 [(CAS: 945421-81-8)], Pigment Yellow 79 [(CAS: 331414-25-6)], Pigment Yellow 8 [(CAS: 71872-65-6)], Pigment Yellow 80 [(CAS: 945421-85-2)], Pigment Yellow 82 [(CAS: 12225-14-8)], Pigment Yellow 84 [(CAS: 945421-87-4)], Pigment Yellow 85 [(CAS: 12286-67-8)], Pigment Yellow 86 [(CAS: 12286-68-9)], Pigment Yellow 86 [(CAS: 5280-65-9)], Pigment Yellow 88 [(CAS: 945422-67-3)], Pigment Yellow 89 [(CAS: 945422-85-5)], Pigment Yellow 90 [(CAS: 713104-87-1)], Pigment Yellow 91 [(CAS: 945423-18-7)], Pigment Yellow 96 [(CAS: 12213-63-7)], Pigment Yellow 97 [(CAS: 12225-18-2)], Pigment Yellow 99 [(CAS: 12225-20-6)]

The pigment(s) used in the color composition can include at least two different pigments selected from the above pigment group, or can include at least three different pigments selected from the above pigment group. According to an embodiment, the pigment(s) used in the color composition can include at least one yellow pigment selected from the yellow pigment group consisting of: a Pigment Yellow 83 (CI 21108), CAS #5567-15-7, Pigment Yellow 155 (C.I. 200310), (CAS: 68516-73-4), Pigment Yellow 180 (C.I. 21290), (CAS: 77804-81-0).

In addition to the at least one yellow pigment, or alternatively, the pigments(s) used in the color composition can include at least one red pigment selected from the red pigment group consisting of: Pigment Red 5 (CI 12490), (CAS #6410-41-9), Pigment Red 112 (CI 12370), (CAS #6535-46-2), Pigment Red 122 (CI 73915), (CAS #980-26-7).

In addition to the at least one yellow pigment and/or the at least one red pigment, or alternatively, the pigments(s) used in the color composition can include at least one green pigment selected from the green pigment group consisting of: Pigment Green 36, (C.I. 74265), (CAS: 14302-13-7).

In addition to the at least one yellow pigment and/or the at least one red pigment and or the at least one green pigment, or alternatively, the pigments(s) used in the color composition can include at least one blue pigment selected from the blue pigment group consisting of: Pigment Blue 16, (CAS: 424827-05-4), Pigment Blue 60 (C.I. 69800), (CAS: 81-77-6), Pigment Blue 66, (C.I. 73000), (CAS: 482-89-3)

In addition to the at least one yellow pigment and/or the at least one red pigment and/or the at least one green pigment, and/or the at least one blue pigment or alternatively, the pigments(s) used in the color composition can include at least one black pigment selected from the black pigment group consisting of: Pigment Black 6 (C.I. 77266), (CAS 1333-86-4), Pigment Black 7 (C.I. 77266), (CAS 1333-86-4).

The pigment(s) can optionally have a surface zeta potential of $\geq \pm 15$ mV, preferably $\geq \pm 20$ mV, more preferably $\geq \pm 25$ mV. The surface zeta potential can be measured with a zetasizer, for example, a Zetasizer 3000 HS. Surface zeta potential measurements are conducted, for example, according to ISO 13099.

For example, the white or colored organic pigments can be chosen from carmine, carbon black, aniline black, melanin, azo yellow, quinacridone, phthalocyanin blue, sorghum red, the blue pigments codified in the Color Index under the references CI 42090, 69800, 69825, 73000, 74100, and 74160, the yellow pigments codified in the Color Index under the references CI 11680, 11710, 15985, 19140, 20040, 21090, 21100, 21108, 47000, 47005 and 77492.

The green pigments codified in the Color Index under the references CI 61565, 61570, 74265, and 74260, the orange pigments codified in the Color Index under the references CI 11725,12075, 15510, 45370, and 71105, the red pigments codified in the Color Index under the references CI 12085, 12120, 12370, 12420, 12490, 14700, 15525, 15580, 15585, 15620, 15630, 15800, 15850, 15865, 15880, 17200, 26100, 45380, 45410, 45430, 58000, 73360, 73915, 75470, and 77491

Non-limiting examples that can also be mentioned include pigmentary pastes of organic pigments, such as the products sold by the company Hoechst under the names: JAUNE COSMENYL IOG: Pigment Yellow 3 (CI 11710); JAUNE COSMENYL G: Pigment Yellow 1 (CI 11680); ORANGE COSMENYL GR: Pigment Orange 43 (CI 71105); ROUGE COSMENYL R: Pigment Red 4 (CI 12085); CARMINE COSMENYL FB: Pigment Red 5 (CI 12490); VIOLET COSMENYL RL: Pigment Violet 23 (CI 51319); BLEU COSMENYL A2R: Pigment Blue 15.1 (CI 74160); VERT COSMENYL GG: Pigment Green 7 (CI 74260); and NOIR COSMENYL R: Pigment Black 7 (CI 77266).

The at least one pigment in accordance with the present disclosure can also be in the form of at least one composite pigment as described in European Patent Publication No. EP 1 184 426 A2. These composite pigments can be, for example, compounds of particles comprising a mineral core, at least one binder for ensuring the binding of the organic pigments to the core, and at least one organic pigment at least partially covering the core.

The at least one pigment in accordance with the present disclosure can be in the form of small undissolved micropar- ticles, which do not diffuse into the hair color, but deposit on the outer wall of the keratin fiber. Suitable color pigments can be of organic and/or inorganic origin. But the pigments can also be inorganic color pigments, given the excellent light, weather and/or temperature resistance thereof.

Inorganic pigments, whether natural or synthetic in origin, include those produced from chalk, red ocher, umbra, green earth, burnt sienna or graphite, for example. Furthermore, it is possible to use black pigments, such as iron oxide black, color pigments such as ultramarine or iron oxide red, and fluorescent or phosphorescent pigments as inorganic color pigments.

Colored metal oxides, metal hydroxides and metal oxide hydrates, mixed phase pigments, sulfurous silicates, sili- cates, metal sulfides, complex metal cyanides, metal sul- fates, metal chromates and/or metal molybdates are particu- larly suitable. In particular, preferred color pigments are black iron oxide (CI 77499), yellow iron oxide (CI 77492), red and brown iron oxide (CI 77491), manganese violet (CI 77742), ultramarine (sodium aluminum sulfosilicates, CI 77007, Pigment Blue 29), chromium oxide hydrate (CI 77289), iron blue (ferric ferrocyanide, CI 77510) and/or carmine (cochineal).

The at least one pigment can also be colored pearlescent pigments. These are usually mica-based and can be coated with one or more metal oxides from the group consisting of titanium dioxide (CI 77891), black iron oxide (CI 77499), yellow iron oxide (CI 77492), red and brown iron oxide (CI 77491, CI 77499), manganese violet (CI 77742), ultramarine (sodium aluminum sulfosilicates, CI 77007, Pigment Blue 29), chromium oxide hydrate (CI 77289), chromium oxide (CI 77288) and/or iron blue (ferric ferrocyanide, CI 77510).

Mica forms part of the phyllosilicates, including musco- vite, phlogopite, paragonite, biotite, lepidolite, and marga- rite. To produce the pearlescent pigments in combination with metal oxides, the mica, primarily muscovite or phlogo- pite, is coated with a metal oxide.

As an alternative to natural mica, it is also optionally possible to use synthetic mica coated with one or more metal oxides as the pearlescent pigment. Such suitable pearlescent pigments based on natural micas are described in, e.g., WO 2005/065632. The at least one pigment can also be pearl- escent pigments based on natural or synthetic mica and are coated with one or more of the aforementioned metal oxides. The color of the respective pigments can be varied by varying the layer thickness of the metal oxide or metal oxides.

The at least one pigment can also be at least one inorganic color pigment selected from the group consisting of colored metal oxides, metal hydroxides, metal oxide hydrates, sili- cates, metal sulfides, complex metal cyanides, metal sul- fates, bronze pigments and/or colored pigments based on mica, which are coated with at least one metal oxide and/or a metal oxychloride.

The at least one pigment can also be at least one mica- based colored pigment, which is coated with one or more metal oxides from the group consisting of titanium dioxide (CI 77891), black iron oxide (CI 77499), yellow iron oxide (CI 77492), red and/or brown iron oxide (CI 77491, CI 77499), manganese violet (CI 77742), ultramarine (sodium aluminum sulfosilicates, CI 77007, Pigment Blue 29), chro- mium oxide hydrate (CI 77289), chromium oxide (CI 77288) and/or iron blue (ferric ferrocyanide, CI 77510).

The at least one pigment can also be color pigments commercially available, for example, under the trade names Rona®, Colorona®, Dichrona® and Timiron® from Merck, Ariabel® and Unipure® from Sensient, Prestige® from Eckart Cosmetic Colors, and Sunshine® from Sunstar.

The at least one pigment can also be color pigments bearing the trade name Colorona® are, for example: Colo- rona Copper, Merck, MICA, CI 77491 (IRON OXIDES); Colorona Passion Orange, Merck, Mica, CI 77491 (Iron Oxides), Alumina; Colorona Patina Silver, Merck, MICA, CI 77499 (IRON OXIDES), CI 77891 (TITANIUM DIOX- IDE); Colorona RY, Merck, CI 77891 (TITANIUM DIOX- IDE), MICA, CI 75470 (CARMINE); Colorona Oriental Beige, Merck, MICA, CI 77891 (TITANIUM DIOXIDE), CI 77491 (IRON OXIDES); Colorona Dark Blue, Merck, MICA, TITANIUM DIOXIDE, FERRIC FERROCYA- NIDE; Colorona Chameleon, Merck, CI 77491 (IRON OXIDES), MICA; Colorona Aborigine Amber, Merck, MICA, CI 77499 (IRON OXIDES), CI 77891 (TITANIUM DIOXIDE); Colorona Blackstar Blue, Merck, CI 77499 (IRON OXIDES), MICA; Colorona Patagonian Purple, Merck, MICA, CI 77491 (IRON OXIDES), CI 77891 (TI- TANIUM DIOXIDE), CI 77510 (FERRIC FERROCYA- NIDE); Colorona Red Brown, Merck, MICA, CI 77491 (IRON OXIDES), CI 77891 (TITANIUM DIOXIDE); Colo- rona Russet, Merck, CI 77491 (TITANIUM DIOXIDE), MICA, CI 77891 (IRON OXIDES); Colorona Imperial Red, Merck, MICA, TITANIUM DIOXIDE (CI 77891), D&C RED NO. 30 (CI 73360); Colorona Majestic Green, Merck, CI 77891 (TITANIUM DIOXIDE), MICA, CI 77288 (CHROMIUM OXIDE GREENS); Colorona Light Blue, Merck, MICA, TITANIUM DIOXIDE (CI 77891), FERRIC FERROCYANIDE (CI 77510); Colorona Red Gold, Merck, MICA, CI 77891 (TITANIUM DIOXIDE), CI 77491 (IRON); Colorona Gold Plus MP 25, Merck, MICA, TITA- NIUM DIOXIDE (CI 77891), IRON OXIDES (CI 77491);

Colorona Carmine Red, Merck, MICA, TITANIUM DIOXIDE, CARMINE Colorona Blackstar Green, Merck, MICA, CI 77499 (IRON OXIDES); Colorona Bordeaux, Merck, MICA, CI 77491 (IRON OXIDES); Colorona Bronze, Merck, MICA, CI 77491 (IRON OXIDES); Colorona Bronze Fine, Merck, MICA, CI 77491 (IRON OXIDES); Colorona Fine Gold MP 20, Merck, MICA, CI 77891 (TITANIUM DIOXIDE), CI 77491 (IRON OXIDES); Colorona Sienna Fine, Merck, CI 77491 (IRON OXIDES), MICA Colorona Sienna, Merck, MICA, CI 77491 (IRON OXIDES); Colorona Precious Gold, Merck, Mica, CI 77891 (Titanium dioxide), Silica, CI 77491 (Iron oxides), Tin oxide; Colorona Sun Gold Sparkle MP 29, Merck, MICA, TITANIUM DIOXIDE, IRON OXIDES, MICA, CI 77891, CI 77491 (EU); Colorona Mica Black, Merck, CI 77499 (Iron oxides), Mica, CI 77891 (Titanium dioxide) Colorona Bright Gold, Merck, Mica, CI 77891 (Titanium dioxide), CI 77491 (Iron oxides); Colorona Blackstar Gold, Merck, MICA, CI 77499 (IRON OXIDES); color pigments bearing the trade name Unipure® are, for example: Unipure Red LC 381 EM, Sensient CI 77491 (Iron Oxides), Silica; Unipure Black LC 989 EM, Sensient, CI 77499 (Iron Oxides), Silica; Unipure Yellow LC 182 EM, Sensient, CI 77492 (Iron Oxides), Silica.

Depending on the degree of the change in color that is desired on the keratin fiber, the at least one pigment can also be can be used in varying amounts. The more color pigment that is used, the higher is the extent of the change in color in general. Starting at a certain usage amount, however, the adherence of the pigments to the keratin fiber approaches a limiting value, beyond which it is no longer possible to increase the extent of the change in color by further increasing the pigment amount used. While not wishing to be bound by any specific theory, it is believed that when a certain thickness is achieved, an insignificant amount of the incident lights passes through the pigment layer to make a difference to the observed color due to the hair itself. The rest of the light is either scattered back towards the surface, or absorbed.

The at least one pigment can be partially (Scheme 1, (b), where the dark oval represents a pigment, even though the pigment can be white or colorless) or completely enveloped in a matrix (e.g., a polymer matrix or an inorganic matrix; (Scheme 1, (a)). Or the pigment can be adhered to the surface of a matrix that can be colored or colorless (Scheme 1 (c)).

Scheme 1

(a)

(b)

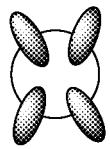

(c)

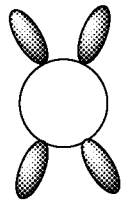

The matrix can be, e.g., $CaCO_3$, $MnCO_3$. Or the matrix can be a melamine formaldehyde matrix.

In another example, the at least one pigment can be encapsulated in silica, as described in Published U.S. Appl. No. 2007/0134180. Other examples of encapsulated pigments include encapsulated Carmine, Iron Oxides, Titanium dioxide, and Chrome Oxide/Hydroxide, the colorants D&C Red 21 Aluminum Lake, D&C Red 7 Calcium Lake, D&C Green 6 Liposoluble, and Aluminium Blue #1 (Indigo Carmine Lake). The encapsulated pigment can be titanium dioxide (used to lighten other pigments and to lend opacity to formulations) in any one of its mineral forms anatase, brookite or rutile, or mixtures thereof. Or the pigment can be at least one iron oxide in any of the 3 basic colors—red, black and yellow iron oxides, or mixtures thereof. From these 3 oxides and the addition of titanium dioxide, any shade of brown (skin tones) can be achieved.

The organic pigment can also be a lake. As used herein, the term "lake" means at least one dye adsorbed onto insoluble particles, the assembly thus obtained remaining insoluble during use. The inorganic substrates onto which the dyes are adsorbed can be, for example, alumina, silica, calcium sodium borosilicate, calcium aluminum borosilicate, calcium carbonate, manganese carbonate, aluminum, nitro-dyes, triarylmethin dyes, Azo-dyes, Anthrazen, Acid dyes, polymethine dyes, triarylmethin dyes, aza annulene dyes and polymethine dyes.

Among the dyes, non-limiting mention can be made of cochineal carmine. Non-limiting mention can also be made of the dyes known under the following names: D&C Red 21 (CI 45 380), D&C Orange 5 (CI 45 370), D&C Red 27 (CI 45 410), D&C Orange 10 (CI 45 425), D&C Red 3 (CI 45 430), D&C Red 4 (CI 15 510), D&C Red 33 (CI 17 200), D&C Yellow 5 (CI 19 140), D&C Yellow 6 (CI 15 985), D&C Green (CI 61 570), D&C Yellow 1 O (CI 77 002), D&C Green 3 (CI 42 053), and D&C Blue 1 (CI 42 090). A non-limiting example of a lake that can be mentioned is the product known under the following name: D&C Red 7 (CI 15 850:1).

The at least one pigment can also be a pigment with special effects. As used herein, the term "pigments with special effects" means pigments that generally create a non-uniform colored appearance (characterized by a certain shade, a certain vivacity, and a certain lightness) that changes as a function of the conditions of observation (light, temperature, observation angles, etc.). They thus contrast with white or colored pigments that afford a standard uniform opaque, semi-transparent, or transparent shade.

Several types of pigments with special effects exist, including those with a low refractive index, such as fluorescent, photochromic, or thermochromic pigments, and those with a high refractive index, such as nacres or glitter flakes. Examples of pigments with special effects of which non-limiting mention can be made include nacreous pigments such as mica coated with titanium or with bismuth oxychloride, colored nacreous pigments such as titanium mica with iron oxides, titanium mica for example with ferric blue or with chromium oxide, titanium mica with an organic pigment of the abovementioned type, and also nacreous pigments based on bismuth oxychloride. Nacreous pigments of which non-limiting mention can be made include the CELLINI nacres sold by Engelhard (mica-TiO$_2$-lake), PRESTIGE sold by Eckart (mica-TiO$_2$), PRESTIGE BRONZE sold by Eckart (mica-Fe$_2$O$_3$), and COLORONA sold by Merck (mica-TiO$_2$—Fe$_2$O$_3$).

In addition to nacres on a mica support, multilayer pigments based on synthetic substrates such as alumina, silica, sodium calcium borosilicate, calcium aluminum borosilicate, and aluminum, can be envisaged.

Non-limiting mention can also be made of pigments with an interference effect that are not fixed onto a substrate, for instance liquid crystals (HELICONES HC from Wacker) and holographic interference flakes (GEOMETRIC PIGMENTS or SPECTRA F/X from Spectratek). Pigments with special effects also comprise fluorescent pigments, whether these are substances that are fluorescent in daylight or that produce an ultraviolet fluorescence, phosphorescent pigments, photochromic pigments, thermochromic pigments, and quantum dots, sold, for example, by the company Quantum Dots Corporation.

Quantum dots are luminescent semiconductive nanoparticles capable of emitting, under light excitation, irradiation with a wavelength ranging from 400 nm to 700 nm. These nanoparticles are known from the literature. They can be manufactured, for example, according to the processes described, for example, in U.S. Pat. Nos. 6,225,198 or 5,990,479, in the publications cited therein, and also in the following publications: Dabboussi B. O. et al. "(CdSe)ZnS core-shell quantum dots: synthesis and characterization of a size series of highly luminescent nanocrystallites" Journal of Physical Chemistry B, vol. 101, 1997 pp. 9463-9475 and Peng, Xiaogang et al. "Epitaxial growth of highly luminescent CdSe/CdS core/shell nanocrystals with photostability and electronic accessibility", Journal of the American Chemical Society, vol. 119, No. 30, pp. 7019-7029.

The variety of pigments that can be used in the present disclosure makes it possible to obtain a wide range of colors, and also optical effects such as metallic effects or interference effects.

The pigments that can be used in the present disclosure can transmit light of various wavelengths, including visible light (e.g., light having a wavelength of above 350 nm). The pigment(s) can also transmit light of certain wavelengths, but also reflect light of certain wavelengths. And the pigment(s) can also be 100% reflective. For examples, reflective pigments provide a high specular reflection of visible light. Reflective pigments include those that are partially or completely coated with a non-matt and non-scattering surface layer of a metal or metal oxide. The substrate can be chosen from glasses, ceramics, graphite, metal oxides, aluminas, silicas, silicates, especially aluminosilicates and borosilicates and synthetic mica (e.g., fluorophlogopite), to name a few. The metal or metal oxide can be, without limitation, titanium oxides, iron oxides, tin oxide, chromium oxide, barium sulfate, $MgF_2$, $CeF_3$, ZnS, ZnSe, $SiO_2$, $Al_2O_3$, MgO, $Y_2O_3$, $SeO_3$, SiO, $HfO_2$, $ZrO_2$, $CeO_2$, $Nb_2O_5$, $Ta_2O_5$ and $MoS_2$, and mixtures thereof. Reflective pigments can have a spectral reflectance in the visible spectrum of at least 70%.

Other reflective pigments include those having non-goniochromatic layered structure of two or more polymeric and/or metallic layers of different refractive indices. For example, reflective particles comprising layers of 2,6-polyethylene naphthalate (PEN) and of polymethyl (meth)acrylate are sold by 3M under the name Mirror Glitter™. Other effect pigments are available under the trade name Metasomes Standard/Glitter in various colors (yellow, red, green, blue) from Flora Tech.

Color Gamut for Pigment Blends

CIE L*a*b* (CIELAB) is a color space specified by the International Commission on Illumination. It describes all the colors visible to the human eye and serves as a device-independent model to be used as a reference.

The three coordinates of CIELAB represent the lightness of the color (L*=0 yields black and L*=100 indicates diffuse white; specular white may be higher), its position between red/magenta and green (a*, negative values indicate green while positive values indicate magenta) and its position between yellow and blue (b*, negative values indicate blue and positive values indicate yellow).

Since the L*a*b* model is a three-dimensional model, it can be represented properly only in a three-dimensional space. Two-dimensional depictions include chromaticity diagrams: sections of the color solid with a fixed lightness.

Because the red-green and yellow-blue opponent channels are computed as differences of lightness transformations of (putative) cone responses, CIELAB is a chromatic value color space.

In the present invention, the color gamut is determined by adding each pigment to be tested in the hair coloring composition, and then individually tested at a level such that when applied to hair, the resulting CIELAB lightness or L* value of the colored hair is 60±2. The level of pigment needed will depend on the pigment being tested. Two hair tresses (Kerling, Natural White special quality) have the hair coloring composition applied as described in the present invention. A Minolta spectrophotometer CM-2600d is used to measure the color of the dried hair tresses, five points on both the front and back sides, and the values averaged. The D65 L*a*b values are calculated. When at least three pigments have each been measured such that their resulting color reside within the target L* values of 60±2 the color gamut can be calculated. First the lengths of each side of the resulting triangle of each combination of three pigments in the a*b plane are computed using the following expressions. To calculate the distance between pigments 1 and pigment 2 the following equation is used:

$$\text{Side Length } SL_{12} = ((a_{pigment\ 1} - a_{pigment\ 2})^2 + (b_{pigment\ 1} - b_{pigment\ 2})^2)^{0.5}.$$

This is computed for each pair of pigments. Then for a series of three pigments.

The resulting color gamut is calculated using the expression:

$$\text{Color Gamut} = (S(S-SL_{12})(S-SL_{13})(S-SL_{23}))^{0.5}$$

wherein $SL_{12}$, $SL_{13}$, and $SL_{23}$ are the three lengths of the sides of the triangle within the a*b plane, and $S=(SL_{12}+SL_{13}+SL_{23})/2$. Where more than three pigments are used, this calculation can be performed for each combination of the three pigment from the more than three pigments used, and the largest Color Gamut is selected.

The hair coloring composition embodiments of the present invention can also have a color gamut of greater than 250, greater than 500, greater than 750, greater than 800, greater than 900, greater than 1100 or even greater than 1250.

Experiments Performed for Color Gamut

Using the above expression, for each combination of three pigments possible from Color Gamut Tables 1, as illustrated below, the color gamut at a nominal L value of 60 was calculated.

Color Gamut Table 1:

| Pigment level | Name | Supplier | wt% | L | a | b |
|---|---|---|---|---|---|---|
| Blue 15 | PV Fast Blue BG-NIP | Clariant | 0.155 | 59.3 | -18.7 | -2.1 |
| Blue 16 | Phthalocyanine | Carbosynth | 0.280 | 59.4 | -17.3 | 1.5 |
| Blue 66 | Indigo 229296 | Aldrich | 0.105 | 60.0 | -3.1 | 6.8 |
| Blue 60 | Paliogen Blau L 6482 | BASF | 0.260 | 60.7 | -3.9 | 5.9 |
| Black 7 | Midnight Black | Geotech | 0.045 | 59.8 | 0.0 | 12.3 |
| Green 36 | Heliogen Green K 9362 | BASF | 0.509 | 60.1 | -32.8 | 20.2 |
| Red 112 | Permanent Red FGR 250 | Clariant | 0.150 | 60.1 | 29.8 | 18.8 |
| Red 122 | Hostaperm Pink E02-EDW VP4034 | Clariant | 0.140 | 59.5 | 24.9 | 6.1 |
| Violet 19 | Ink Jet Magenta ESB 02 M250 | Clariant | 0.200 | 60.6 | 28.1 | 10.1 |
| Red 5 | Permanent Carmine FB01 | Clariant | 0.140 | 59.7 | 30.1 | 14.4 |
| Yellow 155 | Ink Jet Yellow 4GC | Clariant | 16.92 | 61.8 | 9.6 | 74.4 |
| Yellow 83 | Novoperm Yellow HR 70 | Clariant | 1.059 | 60.0 | 12.5 | 61.8 |
| Yellow 180 | Toner Yellow HG | Clariant | 9.16 | 61.4 | 11.2 | 72.8 |

These were formulated within an example formulation described later using an appropriate level of first and second components third compositions.

A few examples are exemplified of combinations of pigments and their resulting color gamut. One skilled in the art would be able to perform this for all of the possible permutations of pigments that are assessed according to the description above.

FIGS. 1 to 4 show plots of color gamut triangles created for a series of three pigment selections.

FIG. 1 shows that a combination of Pigment Green 36, Pigment Yellow 83 and Pigment Red 122 a large triangle is plotted in the a*b* color plane with an area of 1520.

Figure 2:
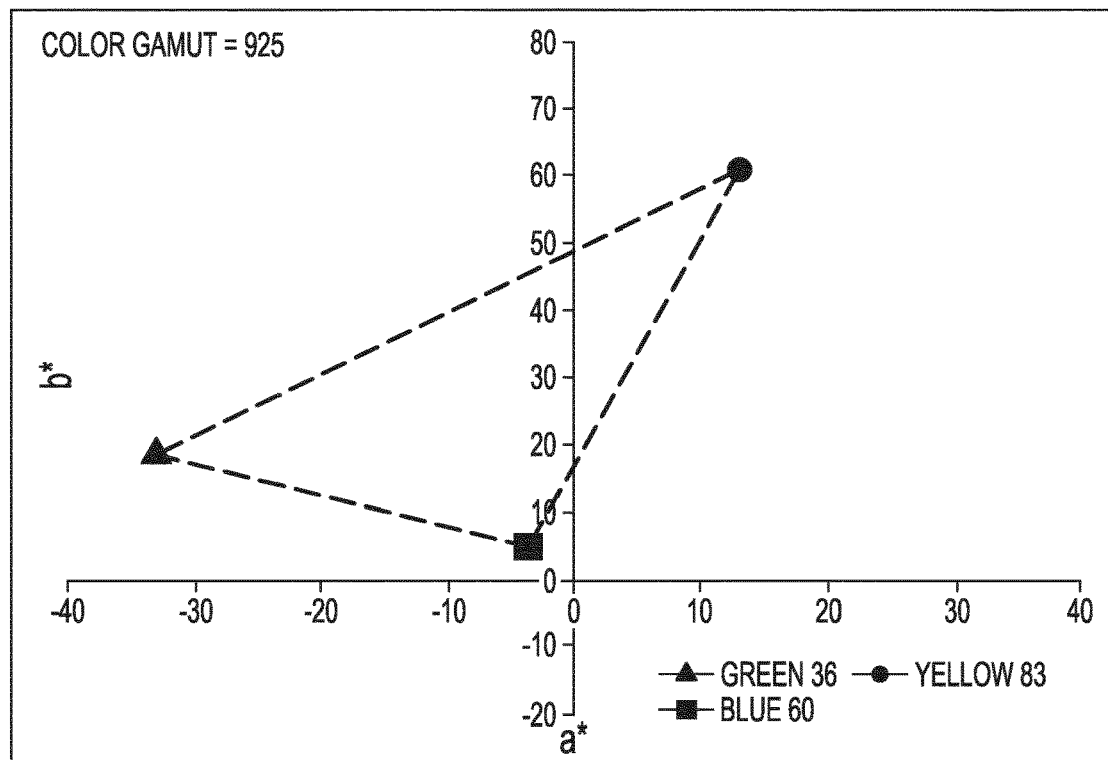
FIG. 2 depicts a Gamut plot of green, yellow and blue pigments.

FIG. 2 shows that a combination of Pigment Green 36, Pigment Yellow 83 and Pigment Blue 60 gives a smaller triangle win an area of 925.

Figure 3:
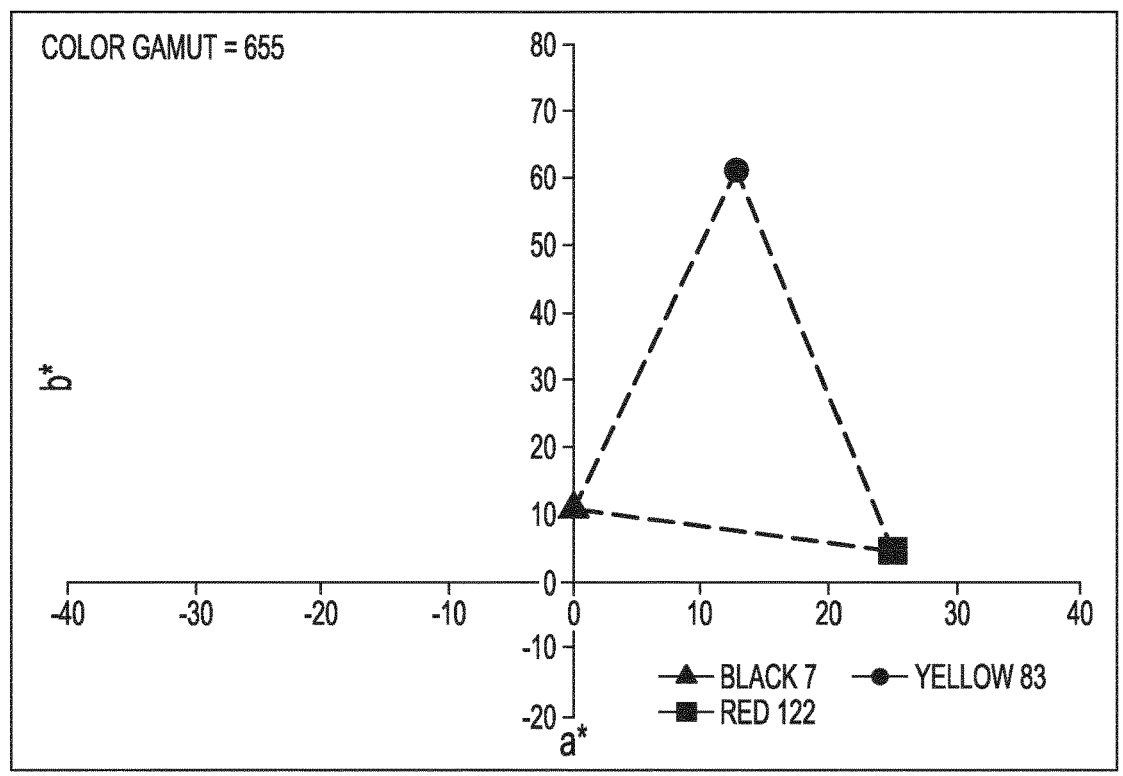
FIG. 3 depicts a Gamut plot of black, yellow and red pigments.

FIG. 3 shows that a combination of Pigment Black 7, Pigment Yellow 83 and Pigment Red 122 gives a smaller triangle win an area of 655.

Figure 4:
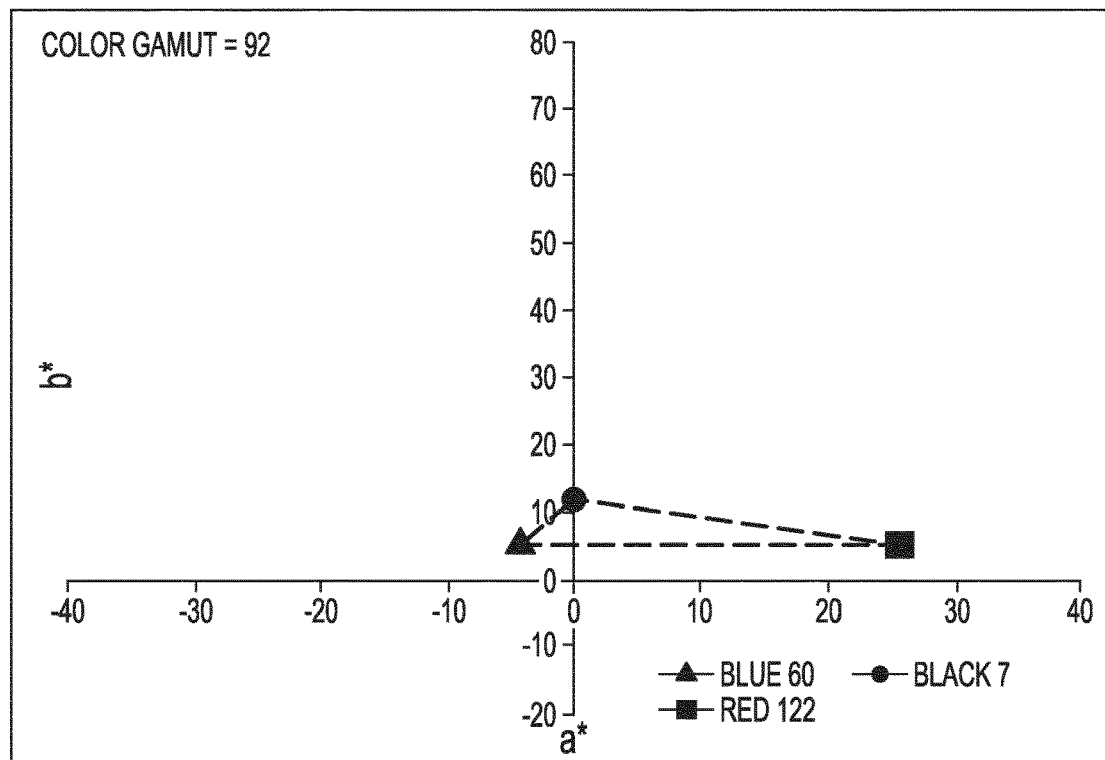
FIG. 4 depicts a Gamut plot of black blue and red pigments.

FIG. 4 shows that a combination of Pigment Black 7, Pigment Blue 60 and Pigment Red 122 gives a smaller triangle win an area of 92.

A second series of example are made for how to assess more than three pigments and their resulting color gamut. When plotted a series of triangles can be plotted as shown and for each the areas is assessed. For such a system the color gamut is defined as the largest of the triangles formed.

Figure 5:
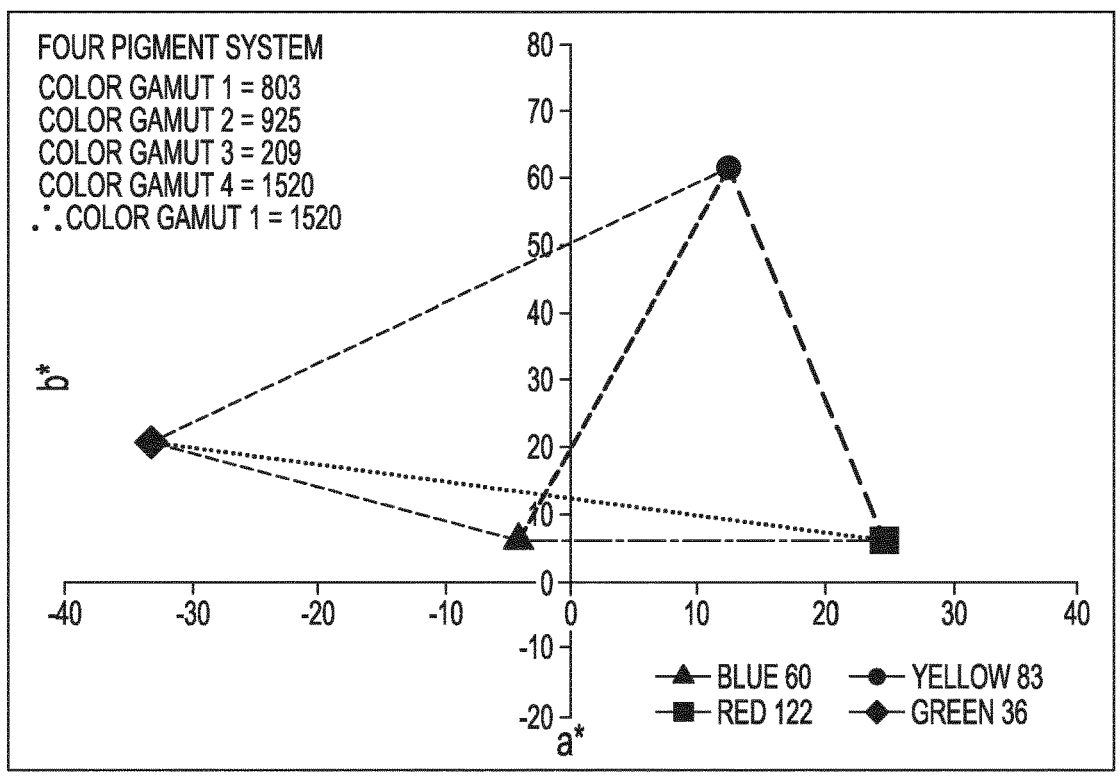
FIG. 5 depicts a Gamut plot of green, yellow, blue and red pigments.

FIG. 5 shows that a combination of Pigment Green 36, Pigment Yellow 83, Pigment Blue 60 and Pigment Red 122 a series of triangles are plotted with areas of 803, 925, 209 and 1520. The color gamut of this pigment system is 1520. [Alterative calculation of total area would yield, 1728]

Figure 6:
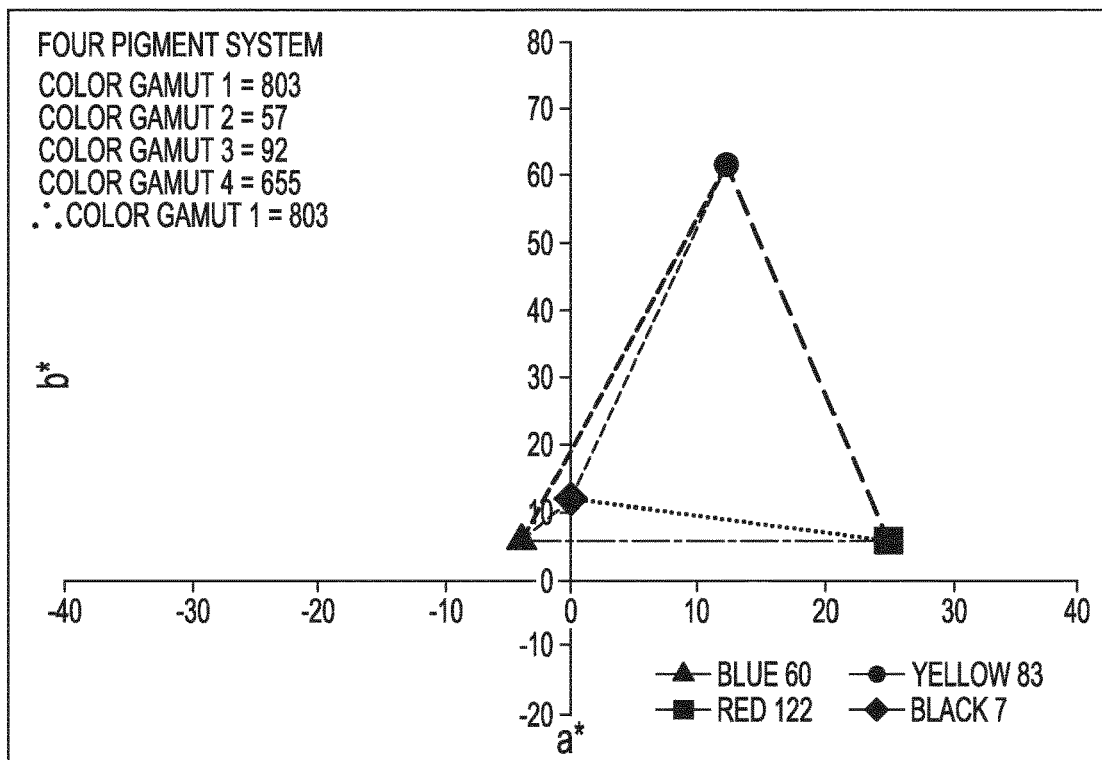
FIG. 6 depicts a Gamut plot of black, yellow and blue and red pigments.

FIG. 6 shows that a combination of Pigment Black 7, Pigment Yellow 83, Pigment Blue 60 and Pigment Red 122 a series of triangles are plotted with areas of 803, 57, 92 and 655. The color gamut of the pigment system is 803 [alternative approach would be the same]

E. The pH

The bicomponent composition embodiments in accordance with the present disclosure can have a pH ranging from about 3 to about 12, preferably about 4 to about 10 and in many embodiments 6.8 or higher. For example, the pH can be 8 or higher, 9 or higher or at most 12. In some examples, the bicomponent composition embodiments in accordance with the present invention can have a pH of from about 7 to about 10, about 5 to about 11 or about 6 to about 8.

The bicomponent composition in accordance with the present disclosure can comprise a pH modifier and/or buffering agent. The amount is sufficiently effective to adjust the pH of the composition/formulation. Suitable pH modifiers and/or buffering agents for use herein include, but are not limited to: ammonia, alkanolamines such as monoethanolamine, diethanolamine, triethanolamine, monopropanolamine, dipropanolamine, tripropanolamine, tripropanolamine, 2-amino-2-methyl-1-propanol, and 2-amino-2-hydroxymethyl-1,3,-propandiol and guanidium salts, alkali metal and ammonium hydroxides and carbonates, such as sodium hydroxide, sodium silicate, sodium meta silicate and ammonium carbonate, and acids such as inorganic and inorganic acids, e.g., phosphoric acid, acetic acid, ascorbic acid, citric acid or tartaric acid, hydrochloric acid, and mixtures thereof.

F. Dispersants

It will be apparent to one skilled in the art that careful and selective choice of dispersant can help to maximize performance in terms of maximizing the amount of color produced from an immobilized film, maximizing the remanence or washfastness, and enabling removal of the color.

For example, in the case where the binder polymer is anionic in nature, dispersants which are anionic or nonionic are preferably chosen, rather than cationic, as this avoids undesired precipitation in the formula prior to it forming a colored film on the keratin—i.e. utilizing the principle of avoiding opposing charges.

Likewise, the principle of choosing chemically similar dispersant and binder (for example, a silicone binder paired with a silicone dispersant, can be followed to ensure maximum compatibility.

As well as compatibility as noted above, the other critical criterion in selecting dispersant(s) is their ability to enable pigment to be dispersed down to the primary particle size, preferably with the minimum amount of input mechanical energy. It will be recognized by someone skilled in the art that the concentration of dispersing agent is also a critical factor. In general it is usually required that there is a minium amount for dispersing activity and that below this, the system is either not fully dispersed or, worse, that the dispersant acts as a flocculant.

These two considerations together are used to define preferred materials and their respective concentrations.

It may also be the case, depending on the type of binder polymer used, that the binder itself is also a dispersant (see below for discussion of classes of dispersant). In such cases it is possible that no further dispersing additive may be needed.

Overview of Dispersant Kinds, Properties and Chemistry

Dispersants are amphiphilic or amphiphathic meaning that they are chemical compounds possessing both hydrophilic (water-loving, polar) and lipophilic (fat-loving) properties. Dispersants are surface-active polymers that allow the homogeneous distribution and stabilization of solids, e.g. pigments in a liquid medium (like a binder), by lowering the interfacial tension between the two components. As a result, agglomerates are broken up into primary particles and protected by a protecting dispersant envelope of a re-agglomeration.

The dispersants can be subdivided on the basis of the stabilization mechanism in
1. dispersants for electrostatic stabilization
   a. Anionic dispersing additives
      i. Polyacrylates
      ii. Polyphosphates
   b. Neutral dispersing additives
   c. Cationic dispersing additives
2. Dispersants for steric stabilization Electrostatic Stabilization The pigment surface is occupied by an additive carrying an ionic charge. All pigment particles are charged the same. The mutual repulsion by the charge is greater than the attractions of the pigment particles. The electrostatic stabilization has its relevance mostly in water-based paint systems.

Polyanionic dispersing additives: polycarboxylates (mostly salts of polyacrylic acids), polyphosphates divided into linear polyphosphates and cyclic metaphosphates, polyacrylates salts of polyacrylic acid, as cations, sodium and ammonium are preferred, these polyacrylates are water-soluble, technical products have molecular weights in the range of 2000 to 20,000 g/mol, optimum is about 8000 g/mol Sodium and ammonium salts of the homo- or copolymers of acrylic acid, methacrylic acid or maleic acid Steric Stabilization The attractive forces between the pigment particles are effective only over relatively small distances of the particles from each other. The approach of two particles to each other can be prevented by molecules that are firmly anchored to the pigment surface and carry groups that extend from the surface and may reduce the potential for the pigments to contact one another. By sufficiently long chain lengths, agglomeration can be prevented.

Water-soluble polymers

Block or graft copolymers, so-called AB block copolymers

Example: AB block polymer of 2-vinylpyridine and methacrylic acid ester

Example: AB block copolymer of polyester (based caprolactam) and triethylenetetramine Typical functional groups for the A segment are carboxyl, amine, sulfate and phosphate for inogenous bonds or polyether and polyamide for hydrogen bonds. B represents the solvated side chain, molecular weights 1000 to 15000 g/mol, e.g. modified polyacrylates or polyhydroxystearates Hydrophilic moieties (e.g., polyethers) and pigment affinic groups (e.g. Groups) containing oligomers or polymers.

The following types are distinguished according to the number of monomer types used in the production:
Homopolymers: only one kind of monomer
Copolymers: two monomers
Terpolymers: three monomers Classification according to distribution of the monomers in the polymer:
Statistical polymers: A and B segments are distributed arbitrarily
Block polymers: the monomers are grouped into blocks
Graft polymers: these consist of a linear homopolymer backbone on which side chains of other monomer blocks are grafted Some examples of dispersants for solvent-based systems are:
oligomeric titanates and silanes for inorganic pigments with OH or carboxy groups.
Oligomeric polymeric carboxylic acids for inorganic pigments (cationic).
Polyamines for inorganic pigments, e.g., cationic polymers.
Salts of long-chain polyamines and polycarboxylic acids for inorganic and organic pigments (electroneutral).
Amine/amide-functional polyesters/polyacrylates for the stabilization of organic pigments.

Some examples of dispersants for aqueous systems are:
Inorganic dispersants such as fine-grained CaCO3, Ca3 (PO4) 2, polyphosphates, polyphosphoric acids.
Nonionic surfactants such as ethoxlyated fatty alcohol (e.g. Neodol 25-9), ethoxylated oils (e.g. ethxylated castor oil under the tradename Cremophore RH410)
Block and graft copolymers of the type having distinct hydrophilic and hydrophobic blocks (e.g. ethylene oxide-propylene oxide polymers under the tradename Poloxamer)
Anionic surfactants consisting of the unethoxylated or ethoxylated salts of acids (e.g. sodium ceteth-10-phosphate under the tradename Crodafos).

Examples and classes of nonionic surfactants that can function as dispersants include oligomers (e.g., example, oligomers have up to 20 monomeric units, polymers have at least 20 monomeric units), polymers, and/or a mixture of several thereof, bearing at least one functional group with strong affinity for the surface of the pigment microparticles. For example, they can physically or chemically attach to the surface of the pigment microparticles. These dispersants also contain at least one functional group that is compatible with or soluble in the continuous medium. For example, 12-hydroxystearic acid esters and $C_8$ to $C_{20}$ fatty acid esters of polyols such as glycerol or diglycerol are used, such as poly(12-hydroxystearic acid) stearate with a molecular weight of about 750 g/mol, such as the product sold under the name SOLSPERSE 21,000 by the company Avecia, polyglyceryl-2 dipolyhydroxystearate (CTFA name) sold under the reference DEHYMYLS PGPH by the company Henkel, or polyhydroxystearic acid such as the product sold under the reference ARLACEL P100 by the company Uniqema, and mixtures thereof. Similar dispersants will function to disperse the polar functional silicone polymers that are not readily dispersible and/or are not at least partially soluble in aqueous media.

The foregoing dispersant category involving cationic polymers includes polymers such as quaternary ammonium polymers. Examples of quaternary ammonium derivatives of polycondensed fatty acids include, such as for instance, SOLSPERSE 17,000 sold by the company Avecia, and polydimethylsiloxane/oxypropylene mixtures such as those sold by the company Dow Corning under the references DC2-5185 and DC2-5225 C.

The dispersant can be a polyolefin polymer. These dispersants include but are not limited to an olefinic polymer having a molecular weight of about 100 g/mol to about 5,000,000 g/mol, such as about 1,000 g/mol to about 1,000,000 g/mol. Examples of polymers, include, but are not limited to poly(ethylene), poly(propylene), poly(butylene), poly(isobutylene), poly(isoprene), poly(acetal), poly(ethylene glycol), poly(propylene glycol), poly(butylene glycol), poly(methylmethacrylate), poly(dimethylsiloxane), poly(vinylalcohol), poly(styrene), poly(maleic anhydride), poly(ethylmethacrylate), poly(isobutylmethacrylate), poly(methacrylate), poly(butylmethacrylate), poly(n-butylmethacrylate), poly(vinyl butyrate), poly(vinyl chloride), polysiloxane, and mixtures thereof. The polymers can be random, block, or alternating copolymers. In some embodiments, the polymer is a co-polymer that is made from two or more different monomers, such as the monomers that make the polymers described above. Examples of co-polymers include, but are not limited to polyethers, polyesters, polyamides, acrylics, and polystyrenes. The co-polymer can be alternating monomers, random, or block. Examples include a polyether of alternating or block PEO, PPO groups. Examples of acidic groups include, but are not limited to, carboxylic acids, sulfinic acids, sulfonic acids, phosphonic acids, phosphate esters, maleic anhydrides, and succinic anhydride. In some embodiments, the dispersive additive comprises a group selected from phosphonate, phosphate, phosphite, phosphine, and phosphate ester, such as a phosphate, phosphite, and phosphonic acid. In some embodiments, the acidic group has been converted into a salt.

Representative dispersants are also available from a variety of suppliers, and include various nonionic (e.g., ethoxylated) and anionic (e.g., non-ethoxylated salt) forms including agents from Air Products and Chemicals, Inc. (e.g., SURFYNOL™ PSA336); Archer Daniels Midland Co. (e.g., ULTRALEC™ F deoiled lecithin); Ashland Inc. (e.g., NEKAL™ WS-25-I, which is a sodium bis(2,6-dimethyl 4heptyl)sulfosuccinate); BASF (e.g., DISPEX™ AA 4144, DISPEX ULTRA FA 4425 which is a fatty acid-modified emulsifier having a viscosity of 40,000 cps, DISPEX ULTRA FA 4420 which is a fatty acid-modified emulsifier and a dark brown liquid of unspecified viscosity, DISPEX ULTRA FA 4431 which is an aliphatic polyether with acidic groups having a viscosity of 350 cps, DISPEX ULTRA PA 4501 which is a fatty acid modified polymer having a viscosity of 10,000 cps, DISPEX ULTRA PA 4510, EFKA™ PU 4010, EFKA PU 4047 which is a modified polyurethane, EFKA PX 4300, EFKA ULTRA PA 4510 and EFKA ULTRA PA 4530 which are modified polyacrylates, EFKA FA 4620 which is an acidic polyether having a viscosity of 1,400 cps, EFKA FA 4642 which is an unsaturated polyamide and acid ester salt having a viscosity of 2,000 cps, HYDROPALAT™ WE 3135, HYDROPALAT WE 3136 and HYDROPALAT WE 3317 which are difunctional block copolymer surfactants terminating in primary hydroxyl groups and having respective viscosities of 375, 450 and 600 cps, and TETRONIC™ 901 and TERTRONIC 904 which are tetrafunctional block copolymers terminating in primary hydroxyl groups and having respective viscosities of 700 and 320 cps); Borchers (e.g., BORCHI™ Gen 0451 which is a polyurethane oligomer having a viscosity of about 30,000 cps, BORCHI Gen 0652 which is an amine neutralized acrylic acid copolymer having a viscosity of about 75-300 cps, and BORCHI Gen 1252 and BORCHI Gen 1253 which are acrylic ester copolymers having respective viscosities of about 1,500-3,500 and 50-300 cps); Byk-Chemie (e.g., BYK™ 156 which is a solution of an ammonium salt of an acrylate copolymer, DISPERBYK™ which is a solution of an alkyl ammonium salt of a low-molecular-weight polycarboxylic acid polymer, DISPERBYK-102 which is an acidic copolymer, DISPERBYK™-145 which is a phosphoric ester salt of a high molecular copolymer with pigment affinic groups and a liquid of unspecified viscosity, DISPERBYK-190 which is a solution of a high molecular weight block copolymer with pigment affinic groups, DISPERBYK-2013 which is a structured copolymer with pigment affinic groups having a viscosity of 8,600 cps, DISPERBYK-2055 which is a copolymer with pigment affinic groups and a liquid of unspecified viscosity, DISPERBYK-2060 which is a solution of a copolymer with pigment affinic groups having a viscosity of 3,600 cps, DISPERBYK-2061 which is a solution of a copolymer with pigment affinic groups having a viscosity of 491 cps, DISPERBYK-2091, DISPERBYK-2200 which is a high molecular weight copolymer with pigment affinic groups sold in solid form as pastilles and BYKJET™-9152 which is a copolymer with pigment affinic groups having a viscosity of 21,600 cps); Clariant (e.g., DISPERSOGEN™ 1728 which is an aqueous solution of a novolac derivative having a viscosity of 4,000 cps, DISPEROGEN 2774 which is a novolac alkoxylate having a viscosity of 4,000 cps, GENAPOL™ X 1003 and GENAPOL X 1005 which are fatty alcohol ethoxylates having respective viscosities of about 400 cps and 1,300 cps, HOSTAPAL BV concentrate which is a sulfate ester having a viscosity of about 2,700 cps); Cray Valley (e.g., SMA1440H which is an ammonia salt of a styrene maleic anhydride copolymer solution); Dow Chemical Co. (e.g., the TAMOL™ family of dispersants including TAMOL 165A and TAMOL 731A); Elementis (e.g., NUOSPERSE™ FA196 which has a viscosity of 1,200 cps); Lubrizol (e.g., SOLSPERSE™ 27000, SOLSPERSE 28000, SOLSPERSE 32000, SOLSPERSE 39000, SOLSPERSE 64000, SOLSPERSE 65000, SOLSPERSE 66000, SOLSPERSE 71000, SOLSPERSE M387, SOLPLUS™ R700 and SOLPLUS K500); Ethox Chemicals, LLC (e.g., the E-SPERSE™ family of dispersants and ETHOX™ 4658); Evonik (e.g., TEGO™ DISPERS 656, TEGO DISPERS 685, TEGO DISPERS 750W and TEGO DISPERS 757W); Rhodia Solvay Group (e.g., ABEX 2514 and ABEX 2525 which are nonionic surfactants, RHODACAL™ IPAM which is isopropyl amine dodecylbenzene sulfonate having a viscosity of 10,000 cps, RHODAFAC™ RS-710 which is a polyoxyethylene tridecyl phosphate ester, and the RHODOLINE™ family of dispersants including RHODOLINE 4170 and RHODOLINE 4188); Sasol Wax GmbH (e.g., ADSPERSE™ 100, ADSPERSE 500 and ADSPERSE 868) and Stepan Company (e.g., G-3300 which is an isopropyl amine salt of an alkyl aryl sulfonate having a viscosity of about 6000 cps, POLYSTEP™ A-15 which is a sodium dodecylbenzene sulfonate having a viscosity of about 85 cps, POLYSTEP B-11 and POLYSTEP B-23 which are ethoxylated ammonium lauryl ether sulfates respectively containing 4 or 12 moles of ethylene oxide and having respective viscosities of 66 and 42 cps, and POLYSTEP B-24 which is sodium lauryl sulfate having a viscosity of 100 cps).

Commercial dispersant compositions and systems of the synthetic kind described above are sold by several companies who manufacture polymer systems. These include:

BASF
  Water-based system—
    Dispex® Ultra FA, Dispex® AA, Dispex® CX, Dispex® Ultra PX, Dispex® Ultra PA
  Solvent based system
    Efka® FA, Dispex® Ultra FA, Efka® FA, Efka® PU, Efka® PA, Efka® PX Clariant
  Dispersogen® 1728, Dispersogen® 2774, Dispersogen® 3169, Dispersogen® AN 100, Dispersogen® AN 200, Dispersogen® ECS, Dispersogen® ECO, Dispersogen® LFS 6, Dispersogen® PCE, Dispersogen® PL 30, Dispersogen® PL 40, Dispersogen® PTS, Dispersogen®, Emulsogen® LCN 217, Emulsogen® TS 200, Dispersogen®, Dispersogen® FN, Dispersogen® FSE, Dispersogen® MT 200, Dispersogen® LFH, Dispersogen® 145, Dispersogen® 4387, Hostapal® BV, Dispersogen® LEC, Dispersogen® PSM, Polyglykol 200 LVC, Polyglykol G500, Polyglykol 300, Polyglykol 400

Lubrizol
  Solsperse™ 3000, Solsperse™, Solsperse™ 8000, Solsperse™, Solsperse™ 12000S, Solsperse™ 13300, Solsperse™ 13400, Solsperse™ 13500, Solsperse™ 13650, Solsperse™ 13940, Solsperse™ 16000, Solsperse™ 17000, Solsperse™ 17940, Solsperse™ 17000, Solsperse™ 18000, Solsperse™ 19000, Solsperse™ 20000, Solsperse™ 21000, Solsperse™ 22000, Solsperse™ 24000SC, Solsperse™ 26000, Solsperse™ 27000, Solsperse™ 28000, Solsperse™ 32000, Solsperse™ 32500, Solsperse™ 32600, Solsperse™ 33000, Solsperse™ 35000, Solsperse™ 35100, Solsperse™ 35000, Solsperse™ 36000, Solsperse™ 36600, Solsperse™ 37500, Solsperse™ 38500, Solsperse™ 39000, solsperse W100.

Byk
  DISPERBYK-102, DISPERBYK-103, DISPERBYK-106, DISPERBYK-107, DISPERBYK-108, DISPERBYK-109, DISPERBYK-110, DISPERBYK-111, DISPERBYK-115, DISPERBYK-118, DISPERBYK-130, DISPERBYK-140, DISPERBYK-142, DISPERBYK-145, DISPERBYK-161, DISPERBYK-162, DISPERBYK-163, DISPERBYK-164, DISPERBYK-166, DISPERBYK-167, DISPERBYK-168, DISPERBYK-170, DISPERBYK-171, DISPERBYK-174, DISPERBYK-180, DISPERBYK-181, DISPERBYK-182, DISPERBYK-184, DISPERBYK-185, DISPERBYK-187, DISPERBYK-190, DISPERBYK-191, DISPERBYK-192, DISPERBYK-193, DISPERBYK-194 N, DISPERBYK-199, DISPERBYK-2000, DISPERBYK-2001, DISPERBYK-2008, DISPERBYK-2009, DISPERBYK-2010, DISPERBYK-2012, DISPERBYK-2013, DISPERBYK-2015, DISPERBYK-2022, DISPERBYK-2023, DISPERBYK-2025, DISPERBYK-2026, DISPERBYK-2050, DISPERBYK-2055, DISPERBYK-2060, DISPERBYK-2061, DISPERBYK-2062, DISPERBYK-2070, DISPERBYK-2080, DISPERBYK-2081, DISPERBYK-2096, DISPERBYK-2117, DISPERBYK-2118, DISPERBYK-2150, DISPERBYK-2151, DISPERBYK-2152, DISPERBYK-2155, DISPERBYK-2157, DISPERBYK-2158, DISPERBYK-2159, DISPERBYK-2163, DISPERBYK-2164, DISPERBYK-2200, DISPERBYK-2205

DOW
  TAMOL™ 1124; TAMOL™ 1254; TAMOL™ 165A; TAMOL™ 2002; TAMOL™ 2011; TAMOL™ 681; TAMOL™ 731A; TAMOL™ 851; TAMOL™ 901; TAMOL™ 945; TAMOL™ 960; TAMOL™ 963; TAMOL™ 983

Following the foregoing principles and guidelines, the pigment microparticles can be dispersed in the composition with the addition of at least one of a dispersant and a wetting agent. While not wishing to be bound by any specific theory, it is believed that only when the pigments are de-aggregated into their primary particles do they deliver the optimum optical performance. For examples, pigments with a primary particle size of 0.02 micron which provide brilliant bright colors, when present as aggregates of around 0.3 micron provide duller colors.

The dispersant serves to protect the pigment microparticles against agglomeration or flocculation either in the dry state or in the solvent. Dispersants also serve as wetting agents. In this capacity, dispersants as wetting agents can be low or higher molecular weight monomeric surfactants (for example, anionic, cationic or amphoteric surfactants). Dispersants as wetting agents can be higher molecular weight surface-active or pigment particle affinic polymers (for example, polyelectrolyte dispersants such as maleic acid copolymers, and polyurethanes or polyacrylates containing carboxylic acid, amine or isocyanate pigment affinic anchor groups or polyethylene imines) or other type of polyelectrolytes.

Representative wetting agents include those available from a variety of suppliers including Air Products and Chemicals (e.g., CARBOWET™ GA-210 surfactant which has a viscosity of 80 cps, CARBOWET GA-221 surfactant which has a viscosity of 100 cps, DYNOL™ 607 superwetter which has a viscosity of 205 cps and DYNOL 800 superwetter which has a viscosity of 230 cps); Dow Chemical Co. (e.g., CAPSTONE™ fluorosurfactants FS 31, FS 34, FS 35, FS 61 and FS 64); and Stepan Company (e.g., STEPWET™ DOS-70 surfactant which contains 70% active ingredients and has a viscosity of 200 cps, and STEPWET DOS-70EA surfactant which contains 70% active ingredients and has a viscosity of 220 cps).

G. Incorporation of Pigment in Dispersant

The pigments described herein can be chosen and/or modified to be similar enough such that a single dispersant can be used. In other instances, where the pigments are different, but compatible, two or more different dispersants can be used. Because of the extreme small size of the pigment microparticles and their affinity, combination of the pigment microparticles and dispersant to form a substantially homogeneous dispersion that can subsequently be modified and/or diluted as desired is to be accomplished before combination with any or all of the first and second components of the bicomponent composition.

The pigment microparticles can be dispersed and stabilized in the medium by one or more dispersants the properties and kinds of which are described above. The dispersant can either be added to the medium, or to a precursor medium or can form a coating on the microparticles to facilitate dispersion. It is also possible to provide the microparticles with a coating of a dispersant material and additionally provide a further dispersant to the medium, or to a precursor medium, which is used to form the final medium.

The dispersant, either added to the medium or provided as coating, facilitates wetting of the microparticles, dispersing of the microparticles in the medium, and stabilizing of the microparticles in the medium.

The wetting includes replacing of materials, such as air, adsorbed on the surface of the pigment microparticles and inside of agglomerates of the microparticles by the medium. Typically, a complete wetting of the individual microparticles is desired to singularize the particles and to break off agglomerates formed by microparticles adhering to each other.

After wetting, the microparticles can be subjected to de-aggregate and de-agglomerate step, generally referred to as dispersing step. The dispersing step typically includes the impact of mechanical forces such as shear to singularize the microparticles. In addition to shearing to singularize, the microparticles can be broken into even smaller microparticles using, for example, roller mills, high speed mixers, and bead mills. Usual practice involves substantially homogeneous dispersion of the pigments in dispersant through the use of high shear mixing; for example through use to the appropriate ball mill, ultra high pressure homogenizer or other system known by those skilled in the art of pigment dispersion.

During wetting and dispersing, the exposed total surface area of the microparticles increases which is wetted by the dispersant. The amount of the dispersant may be gradually increased during dispersing to account for the increased surface area.

The dispersant also functions as de-flocculation agent keeping the dispersed microparticles in a dispersed state and prevent that they flocculate to form loose aggregates. This stabilization is also needed for long term storage purposes. Different type of stabilization such as electrostatic stabilization and steric stabilization are possible, and the type of dispersant is selected in view of the medium and the material of the microparticles.

The dispersant may be added to a dry powder of the pigment particles when the particles are milled to a desired size. During milling, or any other suitable technique to singularize the pigment particles or to break them into smaller part, the dispersant comes in contact with and adheres to the surface of the microparticles. Freshly generated microparticle surface during milling will be coated by the dispersant so that, after milling, the microparticles with a coating formed by the dispersant are provided.

The coating with the dispersant can also be carried out in a liquid carrier medium to which the dispersant is added. The microparticles can also be milled in the liquid carrier.

H. Optional Components

Optional components of the composition include suspending agents, leveling agents and viscosity control agents. The suspending agents help maintain the pigment particles in dispersed condition and minimize or negate their agglomeration. Suspending agents include fatty acid esters of polyols such as polyethylene glycol and polypropylene glycol. These are similar to plasticizers and function in similar fashion to allow pigment particles to "slip" by each other without retarding or binding interaction. They act as grease in this fashion. Additionally, suspending agents in part participate in promoting the stable dispersion of the pigment particles and avoid settling. The carboxylic acid polymer also participates through its solubilization or interaction with the pigment particles and with the medium. The suspending agents provide another factor for maintaining the stable dispersion. They not only provide the "grease" to facilitate Brownian movement but also in part stabilize through interaction as emulsifiers of the pigment particles in the medium.

The bicomponent composition embodiments in accordance with the present invention can also optionally contain at least one adjuvant, chosen, for example, from reducing agents, fatty substances, softeners, antifoams, moisturizers, UV-screening agents, mineral colloids, peptizers, solubilizers, fragrances, anionic, cationic, nonionic, or amphoteric surfactants, proteins, vitamins, propellants, oxyethylenated or non-oxyethylenated waxes, paraffins, $C_{10}$-$C_{30}$ fatty acids such as stearic acid or lauric acid, and $C_{10}$-$C_{30}$ fatty amides such as lauric diethanolamide.

The bicomponent composition embodiments in accordance with the present invention can further optionally contain one or more additives, including, but not limited to, antioxidants (e.g., phenolics, secondary amines, phosphites, thioesters, and combinations thereof), crosslinking agents, reactive diluents (e.g., low molecular weight mono- or di-functional, non-aromatic, (meth)acrylate monomers such as 1,6-hexanediol di(meth)acrylate, tripropylene glycol di(meth)acrylate, isobornyl(meth)acrylate, 2(2-ethoxyethoxy)ethyl(meth)acrylate, n-vinyl formamide, tetrahydrofurfuryl(meth)acrylate, polyethylene glycol di(meth)acrylate, tripropylene glycol di(meth)acrylate, neopentyl glycol dialkoxy di(meth)acrylate, polyethyleneglycol di(meth) acrylate, and mixtures thereof), non-reactive diluents (e.g., ethylene glycol, di(ethylene glycol), tetra(ethylene glycol), glycerol, 1,5-pentanediol, ethylene glycol monomethyl ether, ethylene glycol dimethyl ether, triethylene glycol monomethyl ether, 2-ethoxyethanol, solketal, benzonitrile, hexamethylphosphoramide, 2-N-methylpyrrolidinone and N,N-dimethylformamide); dyes, fillers (e.g., silica; carbon black; clay; titanium dioxide; silicates of aluminum, magnesium, calcium, sodium, potassium and mixtures thereof; carbonates of calcium, magnesium and mixtures thereof; oxides of silicon, calcium, zinc, iron, titanium, and aluminum; sulfates of calcium, barium, and lead; alumina trihydrate; magnesium hydroxide and mixtures thereof), plasticizers (e.g., petroleum oils such as ASTM D2226 aromatic oils; paraffinic and naphthenic oils; polyalkylbenzene oils; organic acid monoesters such as alkyl and alkoxyalkyl oleates and stearates; organic acid diesters such as dialkyl, dialkoxyalkyl, and alkyl aryl phthalates, terephthalates, sebacates, adipates, and glutarates; glycol diesters such as tri-, tetra-, and polyethylene glycol dialkanoates; trialkyl trimellitates; trialkyl, trialkoxyalkyl, alkyl diaryl, and triaryl phosphates; chlorinated paraffin oils; coumarone-indene resins; pine tars; vegetable oils such as castor, tall, rapeseed, and soybean oils and esters and epoxidized derivatives thereof; esters of dibasic acids (or their anhydrides) with monohydric alcohols such as o-phthalates, adipates and benzoates; and the like and combinations thereof), processing aids, ultraviolet stabilizers (e.g., a hindered amine, an o-hydroxy-phenylbenzotriazole, a 2-hydroxy-4-alkoxybenzophenone, a salicylate, a cyanoacrylate, a nickel chelate, a benzylidene malonate, oxalanilide, and combinations thereof), and combinations thereof.

An additional additive may be a tactile hair modification agent. These may include, but are not limited to, a softening and/or lubricating and/or anti-static and/or hair alignment and/or anti-frizz benefit and/or impact on the keratin fibres.

I. Solids Content

Embodiments of the bicomponent composition include solids and liquids. The solids comprise any substance or material of the bicomponent composition that in a form uncombined with any other material, solvent, liquid or substance is has a solid physical form at ambient conditions. Included at least are the carboxylic acid polymer and the pigment microparticles of the bicomponent composition. The medium, in contrast is a liquid and functions as a solvent and/or a liquid in which solid particles are dispersed. The optional components as well as the plasticizer, dispersing agent, surface treatment agent, cross linking agent and other materials added to the medium, if any, are included in the solids content as long as they remain with the carboxylic acid polymer and pigment microparticles following application and setting of the bicomponent composition as a coating on strands of human hair. This includes substances that ordinarily would be regarded as liquids because they would remain in the coating on strands of hair. The solids content of the bicomponent composition may range from about 1 wt % to about 40 wt % relative to the total weight of the composition. A preferred solids content ranges from about 2 wt % to about 30 wt % and another preferred solids content ranges from about 4 wt % to about 20 wt % relative to the total weight of the composition. An especially preferred solids content range is about 4 wt % to about 10 wt % with contents of about 5 wt %, about 6 wt %, about 7 wt %, about 8 wt %, about 9 wt % and about 10 wt % being more especially preferred.

Testing the Flexibility of a Coating of the Bicomponent Composition

With the film prepared above, it can also be tested for optical density to check that the polymer film does not itself alter the hair appearance of the hair too significantly.

Further the polymer preferably can have a glass transition point (Tg) as described above so that it is possible to prevent the colored coating from being damaged or cracked and to secure washing and friction fastness.

The composition coating can have a surface energy between about 20 and about 50 mN m$^{-1}$ (SI unit?) mJ m$^{-2}$. The composition coating preferably has high transmission, to ensure that it does not interfere with the optics of the hair color. The polymer preferably has a refractive index between 1.4 and 1.6.

Application of First and Second Components of the Bicomponent Composition to Treated Material or Textiles The first and second components of the bicomponent composition may be maintained in separate storage compartments or in separate kit form. A convenient storage means can be utilized such as plastic squeeze tubes, plastic bottles, glass containers, sachets, multi-compartment containers, tooles, spottles syringes and plunger operated dispensing devices. Alternatively, metered or calibrated dispensing containers for providing measured amounts of the components as directed by printed instructions can be provided.

Use of the foregoing delivery means enables preparation of an embodiment for practice of the method of the present invention. This embodiment comprises sequential application of the first and second components to treated material or textiles. Pigment microparticles may be incorporated in either or both of the first and second components.

Pretreatment with Second Component

An embodiment of the method according to the present invention may comprise application of the second component to the treated material as a pretreatment before application of the first component as described above. According to this embodiment of the method, pretreatment with the may be carried out prior to application of the first component. Pretreatment may be carried out immediately prior to application of the first component, or at least 1 hour prior to application of the first component, or at least 24 hours prior to application of the first component, or at least 10 days prior to application of the first second component, or at least one month prior to application of the first component. Preferably, pretreatment may be carried out immediately prior to or within a few minutes up to an hour before application of the first component. Typically, the is at least partially dried with optional heating to at least substantially remove or otherwise eliminate the medium of the. For example excess medium may be removed by contacting with an absorbent fabric or surface or the hair may by heated with a hair drier. Preferably, removal of medium is accomplished before application of the first component.

Core and Shell Alternative

According to an embodiment in which pigment microparticles are incorporated into the, at least some of categories of the base compound can be employed to provide a "core-shell structure" (core-shell morphology) for the pigment microparticles. In the case that the base compound and pigment(s) have a "core-shell structure", the "core" corresponds to the "naked" pigment which features the same properties as defined hereinbefore with reference to the "pigment(s)". The "shell" corresponds to a coating layer of base compound surrounding the "core". The pigments having a core-shell structure may have a $D_{50}$(Vol)particle diameter of from 20 nm to 1 micron, typically 60 nm to 900 nm, more typically 100 nm to 600 nm. As such, embodiments of the present invention also relate to a bicomponent composition comprising a core-shell pigment microparticle arrangement, wherein the core comprises an inorganic and/or organic pigment microparticle material, and the shell comprises at least one base compound, the at least one core-shell construct having a $D_{50}$(Vol) particle diameter of 20 nm to 1 μm. The shell surrounding the core may comprise one or more polymeric shell layers. Typically, the shell may comprise a base compound wherein the base compound is a polymeric shell layer.

A further embodiment involving the core and shell alternative may be accomplished by pretreatment of a prepared dispersion of pigment microparticles with a portion of base compound in appropriate medium to provide a dispersion of pigment microparticles as the core and shell construct ready to be combined with any of the first component.

Application of First Component Following Pretreatment

As described above, first component may be applied to the treated material in combination with the foregoing pretreatment. Application of the first component to treated material may be accomplished by application of the first component to the material. The practice of this step with the pretreatment embodiment initially introduces the first component on top of the pretreatment layer of base compound on the treated material. Because the first component is in a medium, penetration, combination and/or mixing of the first component into the pretreatment layer is believed to be accomplished. The penetration is believed to enable interaction among the organic polymer, the pretreatment base compound and the treated material.

Application of the first component to pretreated treated material is preferably carried out after pretreatment. This sequence may be carried out immediately after pretreatment, or at least 1 hour after pretreatment, or at least 24 hours after pretreatment, or at least 10 days after pretreatment, or at least one month after pretreatment.

The application of the first component may be applied to at least a portion of the treated material or may be applied all over the treated material. The portions of first component may be applied in a single application over all the treated material or may be applied step-by-step to the treated material. The first component may be applied step-by-step, for example, in case the treated material is damaged. Applying the first component in a step-by-step manner as described above, may help to ensure that the treated portions of the treated material are saturated with the first component and may therefore provide a better coverage of the treated material.

The bicomponent composition can be applied to treated material using the coloring procedure described herein afterwards.

Manipulative Techniques for Application

After the pretreatment of the has been accomplished, and the pretreated treated material optionally rinsed, the pretreated treated material can be dried. The treated material can be dried using an elevated temperature. The temperature of the treated material can be increased to elevated temperatures above room temperature such as 40° C. or higher, for example using a hair drier. While the treated material is being dried, some form of interdigitated implement can be used to help separate portions of the treated material, and especially separate hair strands from one another. Examples of interdigitated devices include a comb or a brush. The treated material can be dried with a hair drier while simultaneously being combed or brushed until it is dry to the touch. Alternatively, other means can be employed to dry and separate the treated material such as hair simultaneously. For example, using a combination of air movement and vibrations will accomplish distribution of the bicomponent composition throughout the strands of hair.

Operational Method for Coating Hair

The performance of operational method aspects of the present invention can be applied to keratin fibers to form a coating of the bicomponent composition. This aspect of the invention concerns a method for coloring treated material and comprises applying embodiments of one or more bicomponent compositions for a time sufficient to deposit an effective colored coating on the treated material such as each keratin fiber or hair strand. A somewhat to substantially overall distribution of the coating on the length and circumference of each fiber is produced.

To accomplish this aspect, embodiments of the first component of bicomponent composition are applied to the treated material according to the sequences described above by brushing, painting, spraying, atomizing, squeezing, printing, rubbing massaging or in some manner coating the treated material such as hair strands with the embodiments. Following application of a compositional embodiment to the treated material such as hair strands, the composition is coordinated together preferably by warming with blown warm air from a hair dryer or similarly treated to remove the medium, initiate linking of the organic polymer, the pretreatment base compound, the treated material and if present, remove the volatile base. The setting leaves a substantial to essentially complete overall linked coating of the organic polymer, pretreatment base compound and base compound containing dispersed pigment microparticles and optional additional components.

The combination of the substantive constituents of first and second components during application provides a coating that enables it to resist for a time destruction by washing with dilute mixtures of soap and water or shampoo and water. Color fastness is developed so that washing with dilute aqueous soap solution or dilute aqueous shampoo will not substantially remove the coating, but the coating can be facilely removed by use of a transformation trigger. The properties of the coating include wash-fastness, flexibility, adhesion, abrasion resistance and remanence which are due at least in part to the linked character of the composition constituents including at least the organic polymer, the pretreatment base compound and the base compound and their intermolecular entwining, ionic and electrostatic intermolecular interaction, covalent and/or non-covalent linking, dipole interaction and lipophilic interaction of neutral moieties of these compositional constituents.

Selection of the substantive constituents of the bicomponent composition can be made on the basis of properties such as a solid lattice formation and interaction with the pigment microparticles. Such properties include the flexibility, the hardness, the adhesion, the remanence, the resistance to water or to other chemical compounds, and the abrasion resistance. It is also possible to take advantage of the more versatile properties of block polymers (polymers comprising at least two distinct polymer segments), grafted polymers (polymers containing a polymeric side chain grafted onto the homopolymer or copolymer backbone), or random copolymers (polymers comprising at least two different monomers). In the block copolymers, for example, the amount of hard and soft blocks has a significant impact on the properties of the polymer.

The bicomponent compositions in accordance with the present disclosure can have a viscosity that can be controlled to enable the product to be applied to the hair using either a brush and bowl or a bottle, but with sufficient rheology such that it does not drip and run from the hair onto the face or body.

Alternatively, low viscosity formulations may be applied to the hair via a suitable application device such that it does not drip and run form the hair onto the face and body.

The bicomponent compositions can be utilized in concentrated form or in serial dilutions, to provide for a consistent color results substantially along the entire length of the keratin fibers.

The aspect of coloring mammalian or synthetic keratin fibers with a bicomponent composition as described above includes a method for this coloring. The method comprises:
(i) applying the above-described bicomponent composition to keratin fibers an effective coloring amount of the composition of medium with carboxylic acid polymer, pigment microparticles and optional additional components;
(ii) setting the bicomponent composition by removing or otherwise eliminating the medium (e.g., by drying the composition); and.
(iii) setting the interaction among the first and second components third functional groups of the bicomponent composition by initiating the combination among these groups.

During the setting/drying step, color distribution can be facilitated by concurrently moving and/or stroking the hair with an interdigitating device. Interdigitating devices include a comb or brush. The interdigitating device needs to be pulled substantially along the hair strands from root to tip. It can be pulled through at a rate of 0.1 cm s$^{-1}$ to 50 cm s$^{-1}$ or at a rate between 0.5 cm s$^{-1}$ to 20 cm s$^{-1}$ The bicomponent composition is applied to the mammalian or synthetic keratin fibers in any suitable way including spraying the bicomponent composition, massaging the keratin fibers by hand, after applying the bicomponent composition to the hand or by combing, brushing or otherwise applying the bicomponent composition throughout the mammalian or synthetic keratin fibers.

Unlike current hair coloring approaches that use dyes, the color with the bicomponent compositions described herein occurs on the surface of the hair strands. Current dye based approaches do provide the head of hair with some color variation, as the strands are not identical, and some of these differences are preserved after coloring. There are also differences root to tip which also helps to provide some variation. Using a pigment based surface coloring system such as that of the present invention, the variation of the underlying hair can be substantially removed, leading to a more homogeneous color result. This color result can be a more homogenous application of color. To obtain a somewhat non-homogeneous application of color that tends toward a more natural look, the user can apply the inventive bicomponent composition by any of several techniques.

The methods by which the bicomponent compositions described herein are applied can be modified, such that the user applies the product in one region of the hair, and then can apply a diluted version in another region of the hair. The dilution formula is specially chosen to be compatible with the colorant formulation and reduces the coloring strength, while maintaining the longevity of the color result. This can effectively be a "blank" formulation, which contains broadly the same materials as the coloring formulation, but with lower or no pigments present. When diluted the ratio of the diluent to colorant can be between about 10:1 and about 1:10, about 8:1 and about 1:2 or about 5:1 and about 1:1.

Alternatively, the amount of bicomponent composition applied can be altered in different regions of the hair, for example half the product is applied in the lengths of the hair, leading to a less colorful result. The difference in amounts applied in one region of the hair versus another can be between about 4:1 and about 1:4 or about 2:1 and about 1:2.

Alternatively, a combination of this approaches may be used to deliver the target color variation.

When the foregoing techniques are not possible to be applied, rather than apply a single hair color, it may be possible to apply two or more hair colors to different regions of the hair. When this is done, the different hair colors preferably provide complimentary colors so as to develop an attractive result. The difference in colors that can be used, based on the end result on hair tresses (as described later—natural white hair non pre-bleached) are as follows. As described within the CIELCh system:
Color 1 (LCh) versus Color 2 (LCh)
Color 1 L-15<Color 2 L<Color 1 L+15
0 or Color 1 C-10<Color 2 C<Color 1 C+10
Color 1 h-45<Color 2 h<Color 1 h+45

Those skilled in the art of color measurements will know how to interpret difference in hue angles, h, when they extend from low positive values to those near to 360 degrees due to the periodic circular nature of the hue angle.

The method for use of the bicomponent composition in accordance with the present invention can occur during any suitable period. The period of application can be from about 0 to 30 minutes, but in any event a period that is sufficiently long to permit the coating of pigment microparticles to coat and adhere or bind to each separate keratin fiber, substantially along the entire length of each keratin fiber. The resultant is keratin fibers having a color and permanence that is at least equivalent to the color resulting from oxidative hair color, except under much milder conditions.

The bicomponent compositions described herein can be prepared by the manufacturer as a full shade, e.g., one that is ready to apply to the hair, and then shipped as a discrete unit to the user. The user may need to re-blend the pigment microparticles with the bicomponent composition prior to application to ensure that the bicomponent composition delivers the optimum performance. Such re-blending can require shaking the bicomponent composition for about 1 to about 120 seconds or from about 3 to about 60 seconds. Reblending may also be performed by stirring the bicomponent composition prior to use. This may occur for about 1 to about 120 seconds or from about 3 to about 60 seconds. Although the bicomponent compositions according to the present invention are designed to provide stable suspensions of the pigment particles, the re-blending to agitate the microparticles and resuspend them in a substantially uniform distribution is desirable.

Alternatively, the bicomponent composition can be made on demand from a series of discrete formulations and mixed ready for use. Each bicomponent composition would need to be designed such that the combinations of two or more bicomponent compositions produce readily mixable bicomponent compositions with sufficient stability to be used. For example, at least four bicomponent compositions can be made available for blending, at least 5 bicomponent compositions and even at least 6 bicomponent compositions. Additional composition may also be used to impart other signals into the product, for example modifying the rheology, changing the perfume, altering the shine or hair feel properties.

Multiple compositions comprising different pigments can be blended together prior to application to the keratin fibers. Such blending can be done in a manner so as to apply a plurality of complementary surface colors to the keratin fibers.

The bicomponent compositions can include multiple layers, involving multiple applications of at least the first and second components. It may be beneficial also to periodically reapply the. The techniques for applying multiple layers follow the techniques described above for application of a single bicomponent composition.

The coating of pigment microparticles comprising at least one pigment in a coating of the substantive constituents of the bicomponent composition can be adhered to the treated material such as hair utilizing a coating having a total thickness at any given point along the hair fiber of less than about 5 μm, preferably less than about 2 μm as measured using a scanning electron microscope (SEM). To make such measurements, a coated hair sample can be embedded in a suitable resin, and then sectioned root to tip using techniques known to those skilled in the art of scanning electron microscopy. The thickness of the layer on the surface can then be assessed along the line of cuticles over a length of at least 100 μm. The thickness of layer is determined by averaging 10 points evenly spaced over the section of interest.

As described above, application of the bicomponent composition to sections of treated material such as sections of hair strands can be varied. In addition to varying the concentration of the pigment microparticles and optional coloring agent, different shades and/or colors of bicomponent composition can be applied to different sections of a strand of hair or a group of strands of hair. For example, the hair roots, mid sections and tips sometimes or often have different shades of color in their natural condition. This variation can be mimicked, altered or covered through use of differing shades or colors of the bicomponent composition. Roots, for example can be covered with a lighter shade and the tips can be covered with a darker shade to produce a two tone variation of the hair. Application to the hair of a first portion of bicomponent composition followed by stripping the composition from the hair mid sections and ends followed by setting the remaining composition on the hair roots will provide a first hair color coating on the roots. The mid-sections and tips can be dipped or brush applied with a second portion of bicomponent composition to complete the two color or two tone treatment. The use of multiple bicomponent compositions to produce multiple coatings on the hair can provide overlapping, sequential or coterminous coatings on the hair according to typical and routine techniques for applying multiple versions of hair color practiced by professional hair salons.

Post Treatment

An optional post treatment composition can be applied after treating the treated material such as hair with the bicomponent compositions described herein. This can be applied either directly after completion of coloring with the bicomponent composition. The post treatment can be either single application or multiple application across time. The post treatment can be used to improve one or more of: feel, resistance to shampoo/conditioner/water washing treatments, and shine of the hair. Nonlimiting examples of materials used to improve the feel are those which impart lubricity to the treated material such as hair strands and/or help the hair strands separate during the drying steps, These materials include, for example silicone conditioners, silicone polyethers, silicone polyglucose, polyisobutene, copolymers of ethylene and propylene oxide, and commonly used cosmetic oils and waxes. Nonlimiting examples of materials used to improve shampoo wash resistance are materials which act as a 'sacrificial layer' for example polymeric silicones and their copolymers, silicone resins, cosmetics oils and waxes. Nonlimiting examples of materials used to improve the shine of hair (meaning a decrease of the full width at half maximum parameter of the specular reflection curve as measured by a goniophotometer) are those materials which form a smooth film above the previously applied pigment polymer composite on the hair. In general, any cosmetically known film forming material can be used, but preferred are materials such as polymeric silicones and polycationic materials.

Removal of Color Coating

Hair colorants made from surface films consisting essentially of a binding material plus a pigment, and that are very resistant to everyday hair treatments (such as washing with shampoo, conditioner etc) can be removed via use of specifically designed "removal formulations." These are specific chemical mixtures, described herein, and are designed to work via one or both of two broad mechanisms.

First, the mixture can be made to be a solvent for the pigment itself. In this case the mechanism of removal involves first dissolution of the pigment from the binding matrix, followed by removal from the hair via rinsing with water or some other carrier. In this case it is believed, whilst not being bound by theory, that the chemical nature of the pigment, even when in dissolved form, is such that there is minimal attraction/solubility in the hair matrix itself, thus allowing removal of the color.

Second, the "removal formulation" can be made such that it dissolves, weakens or chemically breaks down the binder material holding the pigment on the hair. In this case it is believed, whilst not being bound by theory, that the pigments embedded in the binder matrix are released due to weakening or dissolution of the binder itself and, because the coloring material is a pigment, it has minimal attraction for the hair surface and is too big to penetrate the hair, and in consequence this facilitates removal of the color.

The combination of the above mechanisms will also provide the desired result of removal of the color.

Changing the pH can have a dramatic impact on the properties of the coating which is adhered to the surface. A soluble base acting as a trigger agent to neutralize acid groups and enable the conjugate base to be readily soluble in a mixture of water and organic solvent will facilely remove the coating. Such bases include amino alcohols such as dimethylaminoethanol (dimethylethanolamine, DMEA), dimethylaminopropanol, and similar amino alkanol agents such as monoethanolamine, diethanolamine and triethanolamine and ammonia. Other bases such as NaOH and $Ca(OH)_2$ can also be used. The concentration of the trigger agent in aqueous solution optionally with an alcohol or ketone organic solvent such as methanol, ethanol, methyl ethyl ketone and the like may range from about 0.1% to about 15% by weight, preferably about 0.5% to about 10% by weight, more preferably about 1% to about 7.5% by weight relative to the total weight of the removal solution.

When the multicomponent composition is applied to the hair, the multi-application process physically distributes the components to cover all of the hair. The spraying, massaging, combing and/or hand manipulating the pretreatment and the first and second components produces the full coverage and at the same time leaves thin spots in the otherwise substantially uniform coating. This activity also will aid in the removal process.

Remanence and Treated Material Inspection

Damage caused to the hair by application of the bicomponent composition and removal of the resulting coating can be assessed by FT-IR (Fourier Transform Infrared) method, which has been established to be suitable for studying the effects of keratin surface damage. Strassburger, J., J. Soc. Cosmet Chem., 36, 61-74 (1985); Joy, M. & Lewis, D.M., Int. J. Cosmet. Sci., 13, 249-261 (1991); Signori, V. and Lewis, D.M., Int. J. Cosmet. Sci., 19, 1-13 (1997)). In particular, these authors have shown that the method is suitable for quantifying the amount of cysteic acid. In general, the oxidation of cystine is thought to be a suitable marker by which to monitor the overall oxidation of the keratinous part of the fiber. Net, the measurement of cysteic acid units by FT-IR is commonly used.

Signori and Lewis (D.M., Int. J. Cosmet. Sci., 19, 1-13 (1997)) have shown that FT-IR using a diamond Attenuated Total Internal Reflection (ATR) cell is a sensitive and reproducible way of measuring the cysteic acid content of single fibers and bundles. Hence, the method that we have employed to measure the cysteic acid content of multiple fiber bundles and full hair switches, is based upon the FTIR diamond cell ATR method employed by Signori and Lewis (1997). The detailed description of the method used for testing the different damage inhibitors follows thereafter:

A Perkin Elmer Spectrum® 1 Fourier Transform Infrared (FTIR) system equipped with a diamond Attenuated Total Internal Reflection (ATR) cell was used to measure the cysteic acid concentration in mammalian or synthetic hair. In this method, hairswitches of various sizes and colors can be used. The switches were platted (−1 plait per cm) in order to minimize variations in surface area of contact between readings. The Oxidative hair Treatment Protocol described above was repeated for 5 cycles to mimic the behavior of hair after repeated bleaching cycles. Following this treatment, four readings per switch were taken (⅓ and ⅔s down the switch on both sides), and an average calculated. Backgrounds were collected every 4 readings, and an ATR cell pressure of 1 N/m was employed. The cell was cleaned with ethanol between each reading, and a contamination check performed using the monitor ratio mode of the instrument. As prescribed by Signori & Lewis in 1997, a normalized double derivative analysis routine was used. The original spectra were initially converted to absorbance, before being normalized to the 1450 $cm^{-1}$ band (the characteristic and invariant protein CH$_2$ stretch). This normalized absorbance was then twice derivatised using a 13 point averaging. The value of the 1450 cm$^{-1}$ normalized 2nd derivative of the absorbance at 1040 cm$^{-1}$ was taken as the relative concentration of cysteic acid. This figure was multiplied by $-1 \times 10^{-4}$ to recast it into suitable units. It was found that virgin mammalian or synthetic hair produced a value of around 20 cysteic acid units, and heavily oxidized hair produced values of around 170. The following instrumental conditions were employed:

Spectral Resolution—4 cm$^{-1}$
Data Interval—0.7 cm$^{-1}$
Mirror Scan Speed—0.2 cm s$^{-1}$
Number of Background Scans—20
Number of Sample Scans—20
Scan Range—4000 cm$^{-1}$ to 600 cm$^{-1}$ When the compositions of the current invention can be applied to the hair and then removed there can be a non-significant change to the level of damage to the hair, whereas with conventional oxidative colorants there can be a large increase in the measured damage.

The instant disclosure is not limited in scope by the specific compositions and methods described herein, since these embodiments are intended as illustration of several aspects of the disclosure. Any equivalents are intended to be within the scope of this disclosure. Indeed, various modifications in addition to those shown and described herein can be within the grasp of those with ordinary skill in the art. Such modifications are also intended to fall within the scope of the appended claims.

Color Selection

Also contemplated herein are bicomponent compositions having a given color area (gamut principle described above) defined by color coordinates (a*, b*) in the color space represented by the L*a*b* color system, which can be divided into a plurality of color areas. Each of the plurality of colors obtained from the area surrounding a given set of hair fibers is judged to belong to which color area of the colored area of a certain color. The number of colors judged for each color area is counted, and the color of the color area with the largest number of colors is selected as a representative color of the area surrounding a given set of hair fibers. The compositions are capable of delivering colors on hair (test method herein for fade) such that the results colors lie within the range of about 18<L<about 81, about −2<a<about 45, and about −13<b<about 70.

Also contemplated herein are bicomponent compositions that do not change the hair color, but instead change some other feature of the hair including shine (e.g., making it shinier or matte), the thickness of the hair and/or the feel of the hair.

When the color is removed from the treated material such as hair, the waste water/composition can be treated to remove the pigments from the waste water effluent system. This can be achieved by filtration, or through cyclone technology, where the density differences are used to force the pigments to the settle, and the water to pass through.

EXAMPLES

General

The coloring compositions described herein within the example are generally applied to a hair tress, 1 gram of composition per gram of hair, on a flat plate and brushed in to the hair to ensure that all of the strands look visibly coated with the composition. The hair tress is then dried by heating with a hair dryer, while combing until it is dry to the touch and the strands are individualized.

Pretreatment Example

Experiments were carried out to evaluate the contribution of the pretreatment on color uptake and removability using a color composition.

Natural white hair tresses were used. The lower half of the length of the hair tresses were bleached according to a bleach protocol A. The bleached part of the hair tresses show a brightening or color lift.

The prepared hair tresses were subjected to a pretreatment according to a pretreatment protocol given below. After pretreatment, the hair tresses were colored according to a coloring treatment protocol given below. Finally, the colored hair tresses were subjected to an OFF treatment protocol given below.

Pretreatment Protocol

Pretreatment compositions with water as solvent were prepared at given concentrations according to the table below and applied to the hair at a level of 1 ml to each hair tress (about 1 ml per 0.8 g hair). The pretreatment composition was left on the hair tresses for about 5 min before the hair was dried for 30 min in an oven at about 70° C.

Color Treatment

A color composition comprising 5% of film-forming styrene-acrylic resin copolymer (RE-1075 (PMC/SEIKO)) and pigments in a ratio 1:5 of pigment. The color composition is applied to the hair tress, 1 g of composition per g of hair, on a flat plate and brushed in to the hair to ensure that all of the strands look visibly coated with the composition. The hair tress is then dried, while combing with a hair dry until it is dry to the touch and the strands are individualized.

Wash Treatment

The hair tresses were washed for 30 sec with 0.1 g Wella Brillance Shampoo per hair tress and then rinsed for 30 sec. This was repeated 4 times.

Results of Pretreatment Examples

The test results are summarized and discussed below. The influence of the pretreatment were evaluated by assessing the color uptake after coloring without any subsequent washing (column marked with (1)), assessing of the remanence after 5 times washing (column marked with (2)), assessing the removal of unwashed colored hair (column marked with (3)), and assessing the removal of washed colored hair (column marked with (4)). A means very good results, B means acceptable results, C means not acceptable result.

|   | Tested cationic polymers | Conc. wt.% | (1) Color uptake without washing Even perform | (2) Washfastness Wash | (3) OFF relative to (1) Without | (4) OFF relative to (2) | Amino functional group$_{(a)}$ |
|---|---|---|---|---|---|---|---|
| 1 | PEI — 600Da | 0.5% | A | C | B | A | P/S /T |
|   |   | 2.0% | A | C | B | A |   |
| 2 | PEI — 1200Da | 0.5% | A | C | A | B | P/S /T |
|   |   | 2.0% | B | C | A | B |   |

-continued

| | Tested cationic polymers | Conc. wt.% | (1) Color uptake without washing Even perform | (2) Washfastness Wash | (3) OFF relative to (1) Without | (4) OFF relative to (2) | Amino functional group[a] |
|---|---|---|---|---|---|---|---|
| 3 | PEI — 25kDa | | | | | | P/S/T |
| | | 0.1% | A | B | B | B | |
| | | 0.3% | A | A | A | B | |
| | | 0.5% | A | A | B | B | |
| | | 1.0% | A | A | B | B | |
| | | 2.0% | A | | B | B | |
| 4 | PEI — 70kDa | 0.1% | B | B | B | B | P/S /T |
| | | 0.3% | A | A | B | B | |
| | | 0.5% | A | A | B | B | |
| | | 1.0% | A | A | A | B | |
| | | 2.0% | A | | A | B | |
| 5 | P-3000 PEI — 450kDa | 0.1% | B | B | B | B | P/S/T |
| | | 0.3% | A | A | B | C | |
| | | 0.5% | A | A | B | C | |
| | | 1.0% | A | B | B | B | |
| | | 2.0% | A | B | B | B | |
| 6 | PQ-6 Flocare DB 45 VHM Polyquat-6 2 MDa | 0.5% | B | B | C | C | Q |
| | | 2.0% | B | C | C | C | |
| 7 | Flocare C 106 MV Polyquat-6 (40%) 150 kDa | 0.5% | A | C | C | C | Q |
| | | 2.0% | B | C | C | C | |
| 8 | PQ-7 (Flocare DP/C 107 CS PF) about 10 kDa | 0.5% | B | C | C | C | Q |
| | | 2.0% | A | B | C | C | |
| 9 | PQ 7 high Flocare C 107 LM PF— (9.5%) 1.6 MDa | 0.5% | A | C | C | C | Q |
| | | 2.0% | A | C | C | C | |
| 10 | PQ 10 | 0.5% | B | B | C | C | Terminal Q |
| | | 2.0% | B | C | C | C | |
| 11 | Salcare SC 96 (PQ37) | 2% | B | C | C | C | Terminal Q |
| | | 0.5% | A | B | B | B | |
| 12 | Chitosan | 2% | A | B | B | B | P |
| | | 0.5% | A | C | B | B | |
| 13 | PQ4 | 2% | A | C | B | B | Q |
| | | 0.5% | B | C | B | B | |
| 14 | Amsi Aminosilicon fluid | 2% | A | C | B | B | T |
| | | 0.5% | | A | C | B | A |
| 15 | Abil - Abil Quat 3272 | 2% | C | C | A | A | T |
| | | 0.5% | A | B | A | B | |
| 16 | PQM PQ 11 | 2% | A | B | A | A | T |
| | | 0.5% | B | C | A | B | |
| 17 | Polyvinylpyridine 60kD | 0.5% | A | C | B | B | A |
| | | 2.0% | A | A | | | |
| 18 | Poly[(2-ethyldimethylammonioethyl methacrylate ethyl sulfate)-co-(1-inylpyrrolidone)] | 0.5% | A | C | A | A | Terminal Q |
| | | 2.0% | A | C | A | A | |
| 19 | Polyallylamine MW 17KD | 0.5% | A | B | C | C | P |
| | | 2.0% | B | B | C | C | |
| 20 | Polyallylamine MW 40kD | 0.5% | A | A | C | B | P |
| | | 2.0% | A | B | C | B | |

[a] Functional groups of the cationic polymer: A =aromatic amino functional group,
P =primary amino functional group; S =secondary amino functional group;
T =tertiary amino functional group; Q =quaternary amino functional group.

The polyethyleneimine (PEI) pretreatment increases the remanence and shows somewhat satisfactory results for PEI having a weight average molecular weight in the range of about 4 kDa to about 450 kDa, particularly in the range of about 25 kDa and 450 kDa. Even low PEI concentrations are sufficient as the impact on coloring performance remains stable. The hair feeling increase with washing and decreasing molecular weight of the PEI, with low molecular weight PEI of about 25 kDa produces a more natural feeling than PEI having a molecular weight of about 450 kDa. In addition, a hydroxyl functional acrylic polymer combined with PEI was studied for remanence. The coating did not survive five wash cycles. The color removal appears to be better on non-bleached hair. Other suitable cationic polymers are polyallylamine and polyvinylpyridine.

EMBODIMENT STATEMENTS

1. A multicomponent composition for coloring keratin material comprising a first component of at least one organic polymer with functional groups, at least one pigment, at least one volatile solvent, and a second component comprising a base compound having functional groups capable of forming dipolar or electrostatic interactions with the organic polymer.
2. A multicomponent composition of statement 1 wherein the first and second components are separate.
3. A multicomponent composition of statement 1 or 2 wherein the organic polymer is chosen from polymers and co-polymers based on polyurethane, polyacrylate, silicone resins, polyureas/polyurethane silicones, and copolymers based on silicone resin and on dimethiconol.
4. A multicomponent composition of statements 1, 2 or 3 wherein the base compound comprises an aminosilane, aminosiloxane, aminosilicone, mercaptosilane or a linear or branched polymer comprising linear polyethyleneimine, branched polyethylene imine, a copolymer of aminoethyl (meth)acrylate and ethyl (meth)acrylate, polyallylamine hydrochloride, polydiallyldimethyl ammonium chloride, polyvinylamine, (vinylamine-styrene) copolymer, poly (omega-aminoalkyl(meth)acrylate), polyvinylpyrrolidone poly (2-vinyloxazoline) and random or block copolymers thereof and mixtures thereof.
5. A multicomponent composition of any of statements 1-4 wherein the weight average molecular weight of the base compound is in a range of about 400 Da to about 1 MDa.
6. A multicomponent composition of any of statements 1-5 wherein the organic copolymer comprises repeating units of at least one hydrophobic olefinic carboxylate ester monomer, at least one hydrophilic olefinic monomer and optionally at least one olefin monomer, wherein:
the hydrophobic olefinic carboxylate ester monomer is an ester of (meth)acrylic acid or crotonic acid or a combination thereof and a linear or branched alkanol of 1 to 30 carbons or a combination thereof;
the hydrophilic olefinic monomer is a hydroxy alkyl ester of an olefinic carboxylic acid and a linear or branched alkyl diol of 2 to 24 carbons, or is an aminoalkyl ester of an olefinic carboxylic acid and a linear or branched amino alkyl alcohol of 2 to 24 carbons or is an olefinic acid, or is a combination of any two or more of the hydroxyl alkyl ester, the amino alkyl ester and the olefinic acid; and
the olefinic acid is selected from (meth)acrylic acid, crotonic acid, maleic acid, fumaric acid, itaconic acid or gluconic acid or a combination of any two or more of the olefinic acids;
the olefin monomer has the formula

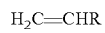

wherein R is selected from linear or branched alkyl of one to six carbons, unsubstituted phenyl or phenyl substituted by a linear or branched alkyl of 1 to six carbons, carboxylic acid, methyl or ethyl carboxylate, carboxamide or hydroxyl.
7. A multicomponent composition of statement 6 wherein the organic copolymer has little or no water solubility.
8. A multicomponent composition of statement 6 wherein the organic copolymer displays water solubility or dispersibility when an opaque mixture of one gram of the organic copolymer in 100 grams of water becomes turbid to cloudy to clear as the pH is increased.
9. A multicomponent composition of statement 6, 7 or 8 wherein the organic copolymer has at least one acid group per molecule.
10. A multicomponent composition of any of statements 6-9 wherein the hydrophilic monomer is a combination of the hydroxyalkyl olefinic ester and the olefinic acid.
11. A multicomponent composition of any of statements 6-10 wherein the organic copolymer comprises the hydrophobic ester monomer and the olefin monomer.
12. A multicomponent composition of any of statements 6-10 wherein the organic copolymer is free of olefinic monomer.
13. A multicomponent composition according to any of the preceding statements wherein the olefinic acid is (meth) acrylic acid or crotonic acid.
14. A multicomponent composition of statement 13 wherein the olefinic acid is (meth)acrylic acid.
15. A multicomponent composition of any of statements 6-11, 13, 14 wherein the olefin monomer is styrene or carboxystrene methyl or ethyl ester.
16. A multicomponent composition of any of statements 6-11, 13, 14 wherein the olefin monomer is hydroxystyene, carboxystyrene or carboxamidostyrene.
17. A multicomponent composition of any of the preceding statements wherein the base compound is an organic polymer, oligomer or compound with pendant and/or terminal and/or in-chain amine groups or any combination thereof or is a polysilicone having pendant amine groups, or an amino silane or a mercapto silane.
18. A composition according to statement 17 wherein the base compound is linear or branched polyethylene imine or a copolymer of aminoethyl (meth)acrylate and ethyl (meth) acrylate polyallylamine hydrochloride or polydiallyldimethyl ammonium chloride.
19. A composition of the preceding statements wherein the weight percent of the base compound is 0.1-5 wt. % relative to the total composition.
20. A multicomponent composition of the preceding statements wherein
the organic polymer has an acid value of from about zero to about 250;
the organic polymer has a glass transition temperature of from about −120° C. to about −40° C.;
the organic polymer has a weight average molecular weight in the range of about 2 KDa to about 10 MDa; and
the composition has a pH of from about 3 to about 12.
21 A kit comprising separate compartments in which the first component and the second component of any of the preceding statements are separately contained.
22. A method for coloring keratin material comprising applying first to the keratin material the second component of statement 21 to form a pretreated keratin material, then applying the first component of statement 21 to the pretreated keratin material and drying the coated keratin material with optional heat to form a colored coating on the keratin material.

23. A method of statement 22 wherein the first and second components are applied as foams to portions of the keratin material.

24. A method of statement 22 or 23 wherein the keratin material is hair, eyebrows, eyelashes, skin, nails, textile, leather or a product derived from a commercial animal which product contains or is derived from keratin material of the animal.

25. The composition of the preceding statements, wherein at least one portion of the pigment microparticles is an organic pigment.

26. The composition of the preceding statements, wherein the composition has a pigment solids content of about 0.1 wt % to about 30 wt % preferably about 0.2 wt % to about 10 wt % relative to the total weight of the composition.

27. The composition of the preceding statements, wherein the pigment selected has a hair color gamut of greater than about 250.

28. The composition of the preceding statements, wherein the pigment microparticles have a D50[vol] particle diameter between 0.001 microns and 0.5 microns, preferably between 0.01 microns and 0.5 microns.

29. The composition of the preceding statements, wherein the composition comprises at least one pigment microparticle that has a flake morphology 30. The composition of the preceding statements and any combination thereof further comprising metallic microplatelets or microparticles which impart reflection to the colored human hair strands.

31. A composition of the preceding statements wherein the flake factor is greater than 10.

32. A composition of any of the preceding statements any combination thereof further comprising one or more of a plasticizer, a dispersant, wetting agent, anti-agglomeration agent, preservative, fragrance, an organic dye compound, a feel modification agent or a thickening agent; the dispersant, anti-agglomeration agent capable of providing dispersion of the pigment particles, the plasticizer and thickener capable of providing viscosity parameters to enable flow and hold of the composition on the keratin fibers.

33. A composition of the preceding statements wherein the pigment microparticles comprise organic pigment microparticles, which imparts color to the hair, having a given D50[vol], and pigment microparticles, for providing light scattering properties to the colored hair, having a D50[vol] which is larger than the D50[vol] value of the organic pigment microparticles.

34. A composition of any of the preceding statements and any combination thereof, wherein the composition has a viscosity of from about 0.001 to about 2000 Pa s$^{-1}$.

35. A composition of the preceding statements, wherein the composition has a viscosity of from about 10 to about 75 Pa s$^{-1}$.

36. A composition of the preceding statements wherein the composition has the physical character of a foam.

37. A composition the preceding composition statements wherein the medium for at least one of the components comprises at least one liquid selected from the group consisting of water, protic organic medium, protic organic non-aqueous medium, an aprotic, non-aqueous organic medium and any compatible combination thereof.

38. A composition of statement 37 wherein the medium is water or a non-aqueous organic medium.

39. A composition of statement 37 wherein the medium is an aprotic non-aqueous organic medium that has a boiling point at standard pressure at a temperature of from ambient to about 200° C.

40. A composition of statement 37 wherein the medium is a protic organic medium.

41. A composition of statement 37 wherein the medium is a nonpolar, aprotic organic medium selected from decane, isodecane, isododecane, a liquid silicone, cyclomethicone, glyme or decamethyl cyclopentasiloxane.

42. A composition of the preceding statements wherein the combined concentration of the organic polymer and the pretreatment base compound compared with the concentration of the pigment particles varies according to the relationship of the larger the average submicron size of the pigment, the higher the concentration of combined polymers relative to the concentration of pigment particle, and the minimum baseline concentration relation of pigment to combined polymers is 1:0.3 weight to weight relative to the total weight of the composition.

43. A composition according to the preceding statements, further comprising an excipient selected from a dispersing agent, a preservative, a fragrance, a surfactant, a tactile modification agent and a thickening agent or a combination thereof.

44. A composition of statement 43 wherein the excipient includes at least a dispersing agent and the concentration of the dispersing agent is in an amount able to generate a positive or negative zeta potential in the composition.

45. A composition of statement 108 wherein the dispersing agent is a nonionic surfactant selected from ethoxylated aliphatic alcohol, polyoxyethylene glycol, esters of fatty acids and glycerol, polyethylene glycol esters of fatty acids, anhydrosorbitol esters, polyethoxylated sorbitol esters, polysorbates, poloxamer, nonoxynol, fatty alcohol, tritan, tween, alkoxylated, hydrogenated castor oil.

46. A composition of statement 43-45 wherein the excipient includes at least a thickening agent and the concentration of the thickening agent is sufficient to maintain a suspension of metallic flakes or pigments in the composition.

47. A method for preparing the bicomponent composition the preceding statements comprising dispersing dry pigment microparticles in a portion of a medium to form a slurry, adding additional medium to the slurry and applying a high energy dispersing procedure to prepare a premix of the pigment particles in the medium.

48. A method of statement 47 wherein the pigment particles are dispersed in one of the first and second components.

49. A method of statement 47 wherein the pigment particles are dispersed in the first and second components.

50. A method of statement 49 wherein the pigment particles with the first component differ from the pigment particles with the second component.

51. A method of any of the preceding method statements wherein the organic liquid is an ethoxylated alcohol.

52. A method of any of the preceding method statements wherein the organic liquid includes a dispersing agent of statement 109.

53. A method of any of the preceding statements wherein the high energy dispersing technique includes ultra-high speed, high energy mixing.

54. A kit comprising a multicompartment container, each container comprising one of the first and second components of the bicomponent composition of statement 1 or 2.

55. A composition according to the preceding composition statements including the wherein the first component is maintained in a first compartment, the second component is maintained in a second compartment.

56. A method for coloring keratin material comprising applying first to the keratin material the second component of statement 54 or 55 to form pretreated keratin material.

57. A method of statement 56 further comprising optionally or at least partially drying the on the keratin material.

57. A method of statement 57 further comprising applying the first component to the pretreated keratin material and causing the combined mixture to form a colored coating on the keratin material.

58. A method of statement 57 further comprising drying the colored coating on the keratin material.

59. A colored coating for hair strands produced according to the method of statement 58.

60. A colored coating for hair strands according to statement 59 wherein the composition forms a solid, flexible elastic film on each individualized hair fibre in which are embedded the pigment particles.

61. A colored coating for hair strands according to statement 60 wherein the film has the microscopic appearance of a semicontinuous or continuous coating 62. A colored coating for hair strands according to statements 59-61 which are resistant to color fading by repeated washings according to a standard wash procedure.

63. A colored coating for hair strands according to statement 62 wherein the repeated washings number 5 to 15.

64. A colored coating for hair strands according to statement 63 wherein the repeated washing number 15 or more.

65. A color removal composition for applying to color coated hair strands comprising applying one or more of surfactant, solvent, acid, base, polymer, polyelectrolyte, salt sources of fluorine, ionic liquids to remove the color coating.

SUMMARY STATEMENTS

The inventions, examples and results described and claimed herein may have attributes and embodiments include, but not limited to, those set forth or described or referenced in this application.

All patents, publications, scientific articles, web sites and other documents and ministerial references or mentioned herein are indicative of the levels of skill of those skilled in the art to which the invention pertains, and each such referenced document and material is hereby incorporated by reference to the same extent as if it had been incorporated verbatim and set forth in its entirety herein. The right is reserved to physically incorporate into this specification any and all materials and information from any such patent, publication, scientific article, web site, electronically available information, text book or other referenced material or document.

The written description of this patent application includes all claims. All claims including all original claims are hereby incorporated by reference in their entirety into the written description portion of the specification and the right is reserved to physically incorporated into the written description or any other portion of the application any and all such claims. Thus, for example, under no circumstances may the patent be interpreted as allegedly not providing a written description for a claim on the assertion that the precise wording of the claim is not set forth in haec verba in written description portion of the patent.

While the invention has been described in conjunction with the detailed description thereof, the foregoing description is intended to illustrate and not limit the scope of the invention, which is defined by the scope of the appended claims. Thus, from the foregoing, it will be appreciated that, although specific nonlimiting embodiments of the invention have been described herein for the purpose of illustration, various modifications may be made without deviating from the scope of the invention. Other aspects, advantages, and modifications are within the scope of the following claims and the present invention is not limited except as by the appended claims.

What is claimed is:

1. A bicomponent composition for coloring keratin material comprising a first component of at least one organic copolymer with functional groups, at least one pigment and a second component comprising a base compound having functional groups capable of forming dipolar or electrostatic interactions with the organic copolymer,
wherein:
the organic copolymer comprises repeating units of at least one hydrophobic olefinic carboxylate ester monomer and at least one hydrophilic olefinic monomer;
the hydrophobic olefinic carboxylate ester monomer comprises an ester of (meth)acrylic acid or crotonic acid, or a combination thereof and a linear or branched alkanol of 1 to 30 carbons or a combination thereof;
the hydrophilic olefinic monomer comprises a hydroxy alkyl ester of an olefinic carboxylic acid and a linear or branched alkyl diol of 2 to 24 carbons, or an aminoalkyl ester of an olefinic carboxylic acid and a linear or branched amino alkyl alcohol of 2 to 24 carbons, or an olefinic acid, or a combination of any two or more of the hydroxyl alkyl ester, the amino alkyl ester and the olefinic acid; and
the olefinic acid comprises (meth)acrylic acid, crotonic acid, maleic acid, fumaric acid, itaconic acid or gluconic acid or a combination of any two or more of the olefinic acids; and,
the base compound comprises an aminosilane, aminosiloxane, or mixture thereof.

2. A bicomponent composition of claim 1 wherein the first and second components are separate and one or both of the components further comprises a medium.

3. A bicomponent composition of claim 1 wherein the weight average molecular weight of the base compound is in a range of about 150 Da to 2 kDa.

4. A bicomponent composition of claim 1 wherein the organic copolymer further comprises at least one olefin monomer, wherein:
the olefin monomer has the formula

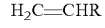

wherein R is selected from linear or branched alkyl of one to six carbons, unsubstituted phenyl or phenyl substituted by a linear or branched alkyl of 1 to six carbons, carboxylic acid, methyl or ethyl carboxylate, carboxamide or hydroxyl.

5. A bicomponent composition of claim 4 wherein the olefinic acid is (meth)acrylic acid or crotonic acid.

6. A bicomponent composition of claim 5 wherein the olefinic acid is (meth)acrylic acid.

7. A bicomponent composition according to claim 1 wherein the olefinic acid is (meth)acrylic acid or crotonic acid.

8. A bicomponent composition of claim 7 wherein the olefinic acid is (meth)acrylic acid.

9. A bicomponent composition of claim 4 wherein the olefin monomer is styrene or carboxystrene methyl or ethyl ester.

10. A bicomponent composition of claim 4 wherein the olefin monomer is hydroxystyene, carboxystyrene or carboxamidostyrene.

11. A bicomponent composition according to claim 4 wherein the weight percent of the base compound is 0.1-5 wt. % relative to the total composition.

12. A bicomponent composition of claim 1 wherein the weight percent of the base compound is 0.1-5 wt. % relative to the total composition.

13. A bicomponent composition of claim 1 wherein
the organic polymer has an acid value of from about zero to about 250;
the organic polymer has a glass transition temperature of from about −120° C. to about −40° C.;
the organic polymer has a weight average molecular weight in the range of about 2 KDa to about 10 MDa; and
the composition has a pH of from about 3 to about 12.

14. A bicomponent composition of claim 4 wherein
the organic polymer has an acid value of from about zero to about 250;
the organic polymer has a glass transition temperature of from about −120° C. to about −40° C.;
the organic polymer has a weight average molecular weight in the range of about 2 KDa to about 10 MDa; and
the composition has a pH of from about 3 to about 12.

15. A kit comprising separate compartments in which the first component and the second component of claim 1 are separately contained, wherein the first component, the second component, or both comprise pigment microparticles.

16. A method for coloring keratin material comprising applying first to the keratin material the second component of claim 15 to form a pretreated keratin material, then applying the first component of claim 15 to the pretreated keratin material and drying the coated keratin material with optional heat to form a colored coating on the keratin material.

17. A method of claim 16 wherein the first and second components are applied as foams to portions of the keratin material.

18. A kit comprising separate compartments in which the first component and the second component of claim 4 are separately contained, wherein the first component, the second component, or both comprise pigment microparticles.

19. A method for coloring keratin material comprising applying first to the keratin material the second component of claim 18 to form a pretreated keratin material, then applying the first component of claim 18 to the pretreated keratin material and drying the coated keratin material with optional heat to form a colored coating on the keratin material.

20. A method of claim 19 wherein the first and second components are applied as foams to portions of the keratin material.

* * * * *